US011708601B2

(12) United States Patent
Taylor et al.

(10) Patent No.: US 11,708,601 B2
(45) Date of Patent: Jul. 25, 2023

(54) MICROMECHANICAL DNA ORIGAMI FORCE SENSOR

(71) Applicant: Carnegie Mellon University, Pittsburgh, PA (US)

(72) Inventors: Rebecca Taylor, Pittsburgh, PA (US); Charlotte Andreasen, Sheboygan, WI (US); Ying Liu, Pittsburgh, PA (US); Yishun Daphne Zhou, Baltimore, MD (US)

(73) Assignee: Carnegie Mellon University, Pittsburgh, PA (US)

( * ) Notice: Subject to any disclaimer, the term of this patent is extended or adjusted under 35 U.S.C. 154(b) by 357 days.

(21) Appl. No.: 17/012,280

(22) Filed: Sep. 4, 2020

(65) Prior Publication Data

US 2021/0071237 A1    Mar. 11, 2021

Related U.S. Application Data

(60) Provisional application No. 62/922,963, filed on Sep. 6, 2019.

(51) Int. Cl.
*C12Q 1/6818* (2018.01)
*C12Q 1/6806* (2018.01)
*B82Y 15/00* (2011.01)

(52) U.S. Cl.
CPC ............ *C12Q 1/6818* (2013.01); *B82Y 15/00* (2013.01); *C12Q 1/6806* (2013.01); *C12Q 2523/305* (2013.01)

(58) Field of Classification Search
CPC ............. C12Q 2523/305; C12Q 2523/303
See application file for complete search history.

(56) References Cited

U.S. PATENT DOCUMENTS

2017/0058325 A1    3/2017  Ly et al.
2017/0108517 A1*   4/2017  Mao ..................... B82Y 5/00

OTHER PUBLICATIONS

Hudoba, M. & C. Castro. Development of a Nanoscale DNA Based Force Transducer. [online] [retrieved on Oct. 22, 2022] Retrieved from https://core.ac.uk/download/pdf/159573811.pdf (Year: 2013).*
Bae et al. Programmed folding of DNA origami structures through single-molecule force control. Nature Communications 5:5654 DOI:10/1038/ncomms6654 (8 pages) (Year: 2014).*
Selnihhin et al. Multifluorophore DNA Origami Beacon as a Biosensing Platform. ACS Nano 12:5699-5708. (Year: 2018).*
Nickels et al. Molecular force spectroscopy with a DNA origami-based nanoscopic force clamp. Science 354(6310):305-307. (Year: 2016).*
Hudoba et al. Dynamic DNA Origami Device for Measuring Compressive Depletion Forces. ACS Nano 11:6566-6573. (Year: 2017).*
Endo et al. Single-molecule imaging of dynamic motions of biomolecules in DNA origami nanostructures using high-speed atomic force microscopy. Acc. Chem. Res. 47:1645-1653. (Year: 2014).*
Choi et al. DNA origami-based Forster resonance energy-transfer nanoarrays and their application as ratiometric sensors. ACS Appl. Mater. Interfaces 10:23295-23302. (Year: 2018).*
Bajar et al., "A Guide to Fluorescent Protein FRET Pairs", Sensors, 2016, pp. 1-24, vol. 16.
Banjo et al., "Haemodynamically dependent valvulogenesis of zebrafish heart is mediated by flow-dependent expression of miR-21", Nature Communications, 2013, pp. 1-11, vol. 4:1978.
Beltran et al., "Extending the Capabilities of Molecular Force Sensors via DNA Nanotechnology", Critical Reviews in Biomedical Engineering, 2020, pp. 1-16, vol. 48:1.
Douglas et al., "Rapid prototyping of 3D DNA-origami shapes with caDNAno", Nucleic Acids Research, 2009, pp. 5001-5006, vol. 37:15.
Finger et al., "Absolute brightness of fluorescent microspheres", Lab Chip, 2009, pp. 476-478, vol. 9:3.
Hoffman et al., "Prevalence of congenital heart disease", American Heart Journal, 2004, pp. 425-439, vol. 147.
Hove et al., "Intracardiac fluid forces are an essential epigenetic factor for embryonic cardiogenesis", Nature, 2003, pp. 172-177, vol. 421.
Hunter, "Nucleic acid-based nanotechnology", EMBO Reports, 2018, pp. 13-17, vol. 19:1.
Ijas et al., "Dynamic DNA Origami Devices: from Strand-Displacement Reactions to External-Stimuli Responsive Systems", Int J Mol Sci, 2018, pp. 1-17, vol. 19:7.
Kahler et al., "Wall-shear-stress and near-wall turbulence measurements up to single pixel resolution by means of long-distance micro-PIV", Experiments in Fluids, 2006, pp. 327-341, vol. 41.
Kearney et al., "DNA Origami: Folded DNA-Nanodevices That Can Direct and Interpret Cell Behavior," Adv Mater., 2016, pp. 5509-5524, vol. 28:27.
Lee et al., "Polymorphic design of DNA origami structures through mechanical control of modular components", Nature Communications, 2018, pp. 1-8, vol. 8:2067.
Lindsey et al., "Mechanical regulation of cardiac development", Frontiers in Physiology, 2014, pp. 1-15, vol. 5:318.
Nelson, "Antibody fragments: Hope and Hype", mAbs, 2010, pp. 77-83, vol. 2:1.
Roy et al., "A Practical Guide to Single Molecule FRET", Nat Methods., 2008, pp. 507-516, vol. 5:6.
Taber, "Mechanical aspects of cardiac development", Progress in Biophysics & Molecular Biology, 1998, pp. 237-255, vol. 69.
Taylor, "DNA Nanotechnology and Microstructures for Biomimetic Sensors and Actuators," Presentation to BEMA Roundtable on Jun. 28, 2018, 48 pages.
Vedula et al., "A method to quantify mechanobiologic forces during zebrafish cardiac development using 4-D light sheet imaging and computational modeling", PLOS Computational Biology, 2017, pp. 1-24, vol. 13:10.
Vedula et al., "Correction: A method to quantify mechanobiologic forces during zebrafish cardiac development using 4-D light sheet imaging and computational modeling", PLOS Computational Biology, 2018, pp. 1, vol. 14:9.

* cited by examiner

*Primary Examiner* — Samuel C Woolwine
(74) *Attorney, Agent, or Firm* — The Webb Law Firm

(57) ABSTRACT

A micromechanical sensor comprising a nucleic acid or nucleic acid analog nanostructure, such as a DNA origami or tiled structure, sensor spring and fluorophores arranged in FRET pairs in the sensor spring is provided, as well as methods of using the micromechanical sensor.

20 Claims, 19 Drawing Sheets

Specification includes a Sequence Listing.

Table A: Unmodified sequences

| Name (SEQ ID NO:) | Sequences |
|---|---|
| ss_1_1 (1) | GAACGGAAGCGAAAACGTGGCGAGAAAGG |
| ss_1_2 (2) | AATCATACAGGCAAGGCAAAGCTTGCGTACCGAG |
| ss_2_1 (3) | CACTAAACATTTGTCACGTTAAAAAAGGCCGGCGAGGAGCG |
| ss_2_2 (4) | TATCTATTAGACTGAATTGCTTTAATATTTAGAGGCAAGT |
| ss_2_3 (5) | TAGTTGCGGACTCCGGGCGCGT |
| ss_2_4 (6) | CAACCATGAGTCCAGTTAAAT |
| ss_2_18 (7) | TGATAAAAATTGCGCAACTGT |
| ss_2_19 (8) | GCGACCTATGAGTGGGTGCGG |
| ss_2_20 (9) | AGCCGGAGTGTAAAACGCCAG |
| ss_2_21 (10) | GTCAATCCATACGAATGTGCT |
| ss_2_22 (11) | CTGACCATCCGCTCTTGGCTA |
| ss_2_23 (12) | CAATAGAATATATTGCCTTGCAGATGAGTTTCCTGCAGTCA |
| ss_2_24 (13) | GATTAATTGCTTCAATAAGTAGGCGCATTCGTAAGACGGCC |
| ss_2_25 (14) | TCTAGAGGATCCCCGGATGCCTGCAGGTCGAC |
| ss_3_1 (15) | AAGGGAAGATACGCCAGAATC |
| ss_3_2 (16) | TCATGGTCAGTGATTAGACAG |
| ss_3_3 (17) | CCATTGAGAGTCTAGGAGGCC |
| ss_3_4 (18) | CCAGAATTAACCGGAATCAGA |
| ss_3_5 (19) | TATCGGCTTTGATTATAACGT |
| ss_3_6 (20) | AACATCACTTGCGCATGGTTGC |
| ss_3_7 (21) | ATTCATAAAACGAAATATTTT |
| ss_3_8 (22) | TACTGCCAAAAATAATATTTA |
| ss_3_9 (23) | TTTAGAGACTATTAACAGGAA |
| ss_3_10 (24) | AGAGGGAGCGGATGATAATCA |
| ss_3_11 (25) | TTTTGCTAAGAGGTCAATCAT |
| ss_3_12 (26) | AAAACCTCAAATAGGTAATCG |
| ss_3_13 (27) | CTCGTTGAGCTTCCAAACAAG |
| ss_3_14 (28) | AAGAGCCGGAAGCTCATTGCC |
| ss_3_16 (29) | TAATGCATTGCTCGAGAGGGT |
| ss_3_17 (30) | TTTAGGTCATTTTCTAGCTGA |
| ss_3_18 (31) | AGAAAGAGCTTAATCAATATG |
| ss_3_19 (32) | CGGAACGCTGTAGCCGGAGAC |
| ss_3_20 (33) | TACGTTAATATGCGATTCAAA |
| ss_3_21 (34) | AGGACGGTCTGGACCTGAGTA |
| ss_3_22 (35) | AACTGGTAACAGTTCATATAT |
| ss_3_23 (36) | ATTACCGCGAACGGGATAAAA |

Fig. 5A

| | |
|---|---|
| ss_3_24 (37) | TTTCAAGACCATTGAAGCCTT |
| ss_3_25 (38) | ATTGGGAATGGTCCCCTGTAA |
| ss_3_26 (39) | AAACACCTATATTGTTGTACC |
| ss_3_27 (40) | AATAAGGAGCTGATCAGAGCA |
| ss_3_28 (41) | AACAAATTCTACTGCAAAATT |
| ss_4_1 (42) | GGCGCTAAGGGATTGGCCACC |
| ss_4_2 (43) | AGCTTGCGAACCCTGCGCGTAACCACCACTCGTTATTGTAGC |
| ss_4_3 (44) | TCTTAAAAAAACCCGCGCTTAATGCGCGAGCACGTAGTAAT |
| ss_4_4 (45) | CGATATATGTTGTTACCAATAGGAACGCATAAGCACAGGTCT |
| ss_4_5 (46) | ACGCCAGTAAATCGTTCATTT |
| ss_4_6 (47) | CGACGTTTAAAGCCAAAGGTG |
| ss_4_7 (48) | AGTGCCAAGAATTAAATAGTA |
| ss_4_8 (49) | ACAAGAACGGATATTCATTAACATCCAATA |
| ss_5_1 (50) | CTGAGAAGTGTTTTTATAAAAATACCTACAT |
| ss_5_2 (51) | GATTAAGGGCGCTGCTTGACGGGGAAAGCTCCAAAAAAACGC |
| ss_5_3 (52) | GCGGGATCACGCTAAAGGGAGCCCCCGTGTATCGACCGCCAG |
| ss_5_4 (53) | GCTTTCCACCCGCGTCTATCAAAATCGTTTCGAGGGTAATAT |
| ss_5_5 (54) | TTTGACCGCTACAAACGTCAAAGGGCGCAGCTTGACTCAAAC |
| ss_5_6 (55) | ACATTAAATTTTTCTATTAAAGAACGTGCCGACACCCTCAAA |
| ss_5_7 (56) | AATTGTTTTTTTACCAGTTTGGAACAACGCCCACTCATAAAT |
| ss_5_8 (57) | GATTGTCATCAAAGAGATAGGGTTGAGTTCGGTCGCGTCCAA |
| ss_5_9 (58) | GAAAAGGGCCTTCTATAAATCAAAAGAGGAGTTAGTAAAATG |
| ss_5_10 (59) | ATGTACCATCAACTCCGAAATCGGCAAGGGATCGGTTTTGCC |
| ss_5_11 (60) | TAAAACAGTAACAAAAATCCTGTTTGAGAAAGACCGAGAGGC |
| ss_5_12 (61) | AGAATCCCGTGGGGCTGGTTTGCCCCAGGTAGCACGACGATA |
| ss_5_13 (62) | TGAGAGTGACCGTGAGTTGCAGCAAGCTTTGAGGTCATAACC |
| ss_5_14 (63) | AAAGGCCGTTGGTCTTCACCGCCTGGCCATGAGGGGCATAGT |
| ss_5_15 (64) | AGCTATCGTAACCGACGGGCAACAGCTCGGGTAATAACGCCA |
| ss_5_16 (65) | TAAATTTTGAGGGGGTTTTTCTTTTCACTACGAACATTCAAC |
| ss_5_17 (66) | ATATTCCGGCCTCTTGCGTATTGGGCGACGAAAGAGTTGAGA |
| ss_5_18 (67) | AGTCAACCAGCCACAACGCGCGGGGAGACTAAAATTACAGGT |
| ss_5_19 (68) | AGGGTGCTTCTGGCAGCTGCATTAATGCCCCAGCCGAACTAA |
| ss_5_20 (69) | ATGTGTCAAAGCGCAGTCGGGAAACCTCGAAACAGAAAAATC |
| ss_5_21 (70) | TTTAAAGGCTGCGTTGCGCTCACTGCCTTTGTATTACCAGTC |
| ss_5_22 (71) | ATTTTTGGCGATCAGCTAACTCACATTTTGTGTCATTTTAAG |
| ss_5_23 (72) | TATTCCGCTATTGCCTGGGGTGCCTAGCTCCATCATTGTGA |
| ss_5_24 (73) | TACTTTAAGGGGGGCCGGAAGCATAAAACGAGGCTGGTTTAA |
| ss_5_25 (74) | AAAAACGATTAAGACAATTCCACACAAATAAGGGAGTAGTAA |

Fig. 5B

| | |
|---|---|
| ss_5_26 (75) | TAAAGCGGTTTTCGTGTGAAATTGTTAACTTTGACTGACGAG |
| ss_5_27 (76) | AAGCAAGTAAAACTCATGGTCATAGCTACGGTGTATTCAGTG |
| ss_5_28 (77) | CTCGAATAGGCTGATCAACGT |
| ss_6_1 (78) | GTAGCGGGCTAAACGTCCATCACGCAAACAATATTGTTTATC |
| ss_6_2 (79) | AATACTTCCTTGCTGTGAATT |
| ss_6_3 (80) | TCTGAGTAGAAGAATACCGA |
| ss_6_4 (81) | GTTAAAATTCGCTTTTAAACAGTTCAGTGAATCCATGACAA |
| ss_6_5 (82) | CAGCTCAAAACGTTGAATGACCATAAATGGAATCGGCATAAC |
| ss_6_6 (83) | TTACCCTCTGGATAGCTGAGG |
| ss_6_7 (84) | CGCGTCTCCCCAAAATAGTCAGAAGCAAGGTAATAAAGGCCG |
| ss_6_8 (85) | CAGCTTTCCCGGTTTGCATCAAAAAGATAAAAGAATCACCCT |
| ss_6_9 (86) | GTGAGCGTAGCATGAAGCCCGAAAGACTAAAATAGAGCATCG |
| ss_6_10 (87) | GGATTCTGATGAACTCGCGTTTTAATTCTACCAGAACGGCTA |
| ss_6_11 (88) | GGCGGATTCTGGAGAAAGCGAACCAGACAACACTAACTAAAG |
| ss_6_12 (89) | TAGGTCATATCAGGAAACTCCAACAGGTATTACGAAAGTTTC |
| ss_6_13 (90) | GGCGCATTTTTGAGAGAGAGTACCTTTAAGATACAAATACGT |
| ss_6_14 (91) | TGCCAGTAATGCCGCTTTTGATAAGAGGAATACCAGGCACCA |
| ss_6_15 (92) | ACAGTATAACCGTTTGCGGATGGCTTAGATTCATCAGGCAAA |
| ss_6_16 (93) | TCGCACTATCACCATTGCTGAATATAATAACATTACACTCAT |
| ss_6_17 (94) | GGCACCGAGAAAGGCTCAACATGTTTTAAATAAAAGATTATA |
| ss_6_18 (95) | AACCAGGAGGTAAAAACTAAAGTACGGTTTGGGAAAAGTACA |
| ss_6_19 (96) | CCATTCATGCAATGAGTTTCATTCCATACTCATTACATCGCC |
| ss_6_20 (97) | TGGGAAGAGAACCCTGATTCCCAATTCTTTATGCGGAAATCC |
| ss_6_21 (98) | GCCTCTTAACGCAAAGTAGATTTAGTTTCTTTAATGTTACTT |
| ss_6_22 (99) | CTGGCGATGCGGGAAGATACATTTCGCACTTGAGAGCAGACG |
| ss_6_23 (100) | GCAAGGCATTATGAAATAACCTGTTTAGCAGAACGAACCGAA |
| ss_6_24 (101) | ACATGGCTTTGATGATACTTCATCAAGAGTAATCTTG |
| ss_7_1 (102) | TTTGACCTCCAAGAAAATGCTCAA |
| ss_7_2 (103) | TTGAAAACAACTCAATAGAA |
| ss_7_3 (104) | TGGTCAGGCCCGAACAACAGT |
| ss_7_4 (105) | TCAAACAAAGTTTGGGATTT |
| ss_7_5 (106) | TAATTCTTTTGCGTAGTAAA |
| ss_7_6 (107) | AAAGACATTTATCAAGAATATAAAGTACCCAGAAGTTTTGTC |
| ss_7_7 (108) | TTCATATCTGAACACATTTTCGAGCCAGTCATATTAGTTAGC |
| ss_7_8 (109) | TTTGTCACCATCCTAACATGTAATTTAGGATGGCACATTCCA |
| ss_7_9 (110) | GACACCATAGAAACATCGCCATATTTAATCCTGATTACAAAC |
| ss_7_10 (111) | AACATATCTGTCTTAACAGTAGGGCTTATTCTGAAAACACTG |
| ss_7_11 (112) | AAATACAAGAACGGACCAGTATAAAGCCGAACCTACAATAGG |

Fig. 5C

| | |
|---|---|
| ss_7_12 (113) | CAGTATGACCGCACATATGCGTTATACATTTGCACCATTTTC |
| ss_7_13 (114) | TGATTAACAAGCCGAGAAAAGCCTGTTAAGAAATCACCCTC |
| ss_7_14 (115) | GAATACCGTAGGAAAACACCGGAATCATGGTTTAAAACCGCC |
| ss_7_15 (116) | CGAGGAAAATAGCAATAAGGCGTTAAATACAGTAAGTTTAGT |
| ss_7_16 (117) | ACAAAGTAGAAGGCGAAATACCGACCGTTCGGGAGGTGTATC |
| ss_7_17 (118) | GAAAAGTAAGAACGCTGACCTAAATTTATCGCCTGTATAAGT |
| ss_7_18 (119) | TCTTACCGAACCTCTATTTTAGTTAATTCAAGTTAAAGTGCC |
| ss_7_19 (120) | ACTTTTGGCGAATTTTGCTC |
| ss_7_20 (121) | CAAGACACCTGAGAAGGATT |
| ss_7_21 (122) | ATGCTGGAAACAAGAGGCTG |
| ss_7_22 (123) | GGGTTAAAATTAATCTGAAA |
| ss_7_23 (124) | TTTTAATTCATTTGCCTATT |
| ss_7_24 (125) | GGAGAATAGTTACAATCAAAATCATAGGAATGGAATATAAAC |
| ss_8_1 (126) | AAAATGAAAATACCGTTCCAGTAAGCGTCAT |
| ss_9_1 (127) | TCGTCTGAAATGAATACCGAACGAACCACCA |
| ss_9_2 (128) | GAGTAAACAACAGGAAGGAGCGAATAATGCAGATTCCCTAAA |
| ss_9_16 (129) | GGGCGCGCTTGCCAAGACGAAGTAACAAAATAAATTAGACG |
| ss_9_17 (130) | GCATCAAGCTGCTCACAGACCTTTAACGAGAATGGACATAAA |
| ss_9_18 (131) | GTAGCATTACCCAAGCTGACCAGGAGTGGAATTTAGCAGCCT |
| ss_10_1 (132) | GCCGTCAATAGATAATCAACTAAACAGAGG |
| ss_10_2 (133) | AGAAGTAAAATATCTTAACAC |
| ss_10_3 (134) | CAATTCGGGAATTGCCACGCT |
| ss_10_4 (135) | ATCCTTTTTGGCAAAATGAAA |
| ss_10_5 (136) | AATTTTACCTCAATCCTTGCT |
| ss_10_6 (137) | TGAATTTATTCATTGGGAAGGTAAATATAAGACAATAAACAA |
| ss_10_7 (138) | GAAACCACGACAAAGCAGAAC |
| ss_10_8 (139) | ATTATCATAATAAGACAATAG |
| ss_10_9 (140) | ATCAGATGCAGAGGAGAAAAA |
| ss_10_10 (141) | AATATAACAACGCCAATTTAC |
| ss_10_11 (142) | ATTATACATTGAGACAATCAA |
| ss_10_12 (143) | AGGGTTAAACGCTCTCCTTAT |
| ss_10_13 (144) | AAAATTAAATTCTTGTATTAA |
| ss_10_15 (145) | ATTTTCAAATTACTTTTTTAT |
| ss_10_16 (146) | TGAATATAAGAATATCATTAC |
| ss_10_17 (147) | TTTTACAGTGATAAAGCAAAT |
| ss_10_18 (148) | AACGGATATGGTTTTTATCCG |
| ss_10_19 (149) | TGAATACTCATCTTCGAGGCG |
| ss_10_20 (150) | GCGCAGATCAAATACCGACTT |

Fig. 5D

| | |
|---|---|
| ss_10_21 (151) | TTCAATTAAAGAACAGCCTTA |
| ss_10_22 (152) | AGATGATATGCAAAGCTATTT |
| ss_10_23 (153) | GAAAACATATAACTATTTTAT |
| ss_10_24 (154) | TAACAATCCTCCGGACGCTAA |
| ss_10_25 (155) | CTTTTTTTCTGAGAGAGCCTA |
| ss_10_26 (156) | ATAAATCTGAATTTAAATAAA |
| ss_10_27 (157) | AATAACCGACGCTGATCCCAA |
| ss_10_28 (158) | CGTCGCTCATAGCGGATTTTTTGTTTAACGTCA |
| ss_11_1 (159) | GCAGAAGATAAATAGATTAGA |
| ss_11_2 (160) | ACATCGCGTCAGTATTTAGGAG |
| ss_11_3 (161) | AGGAACACCAGTAACTTTAATGCGCGAAAACAGTGAGGAAGGT |
| ss_11_4 (162) | TTCAGCGTGGCCAATATTTTTGAATGGCAGCAGCAATCAACAG |
| ss_11_5 (163) | GAACCTCTGAGCGTAAGAATACGTGGCAAGCATCACAATATC |
| ss_11_6 (164) | ATTATCATGTCCAGACGACATA |
| ss_11_7 (165) | GTCTTTCACCGTCAGACATTCAACCGATAGCTAATAGGTAAAG |
| ss_11_8 (166) | AGGATTAAGAGCCAGCAAGAAACAATGAGTTTTGAGCGAGAAA |
| ss_11_9 (167) | AGACTCCGCCACCAGAGTTAAGCCCAATATTAGTTTCCAATCG |
| ss_11_10 (168) | CATGAAAGCCGCCGGAGAGATAACCCACAGCTACAATATGTAA |
| ss_11_11 (169) | TCGGAACAGGTTGAGGTAATTGAGCGCTCTTACCACTTAGGTT |
| ss_11_12 (170) | AGTTAATTTGGCCTACACCCTGAACAAACTTTCCAGACTACCT |
| ss_11_13 (171) | AACAGGGATTATTTAGAAGAGT |
| ss_11_14 (172) | TTACAGAAAGAAACATAGCTTA |
| ss_12_1 (173) | TGAGGCGCATTAAAGATTATTTACATTGAATTTTTAGGATTT |
| ss_12_2 (174) | CGCCTGCCTGATAGCACCAGTCACACGAACTAAAGTTACAAA |
| ss_12_3 (175) | GAGAGCCTATTAGTTAAAGGGACATTCGAGTGAGGTATTAA |
| ss_12_4 (176) | AATCTAACAGACAACAGAGATAGAACCCCAACTTTCGTTATT |
| ss_12_5 (177) | TGCTAAATTCTGACCTGAAACGGAAATTTCTGTATGAGTAAC |
| ss_12_6 (178) | CATGTTCTGAGGGAAAAGGTGAATTATCCAGACGTGAACAAA |
| ss_12_7 (179) | GCGCCTGAAAGGGCCCGACTTGAGCCATTCTAAAGGAGCGGA |
| ss_12_8 (180) | ATAAGTCGGTTTACTTAGAGCCAGCAAACCCTCATCCTGATT |
| ss_12_9 (181) | TAATATCCAATCAAGTAGCACCATTACCCCTGTAGATTCATC |
| ss_12_10 (182) | GAGCATGCGGAATAAGGCCGGAAACGTCTCACCAGTGTTTGG |
| ss_12_11 (183) | TAATCGGAAAAGAAAAACCATCGATAGCGTACCGTTAATGGA |
| ss_12_12 (184) | CATTCCATACATAATAATCAGTAGCGACGCAAGCCCCATATC |
| ss_12_13 (185) | ACCAAGTTTAGCAAAGTTTGCCTTTAGCCCACCCTGTAAAAC |
| ss_12_14 (186) | GAACAAGGACTCCTTGTAGCGCGTTTTCGAACCGCTGCGTAG |
| ss_12_15 (187) | TTTCATCCAAAAGATTTTCGGTCATAGCCCCTCAGCGTCAGA |
| ss_12_16 (188) | CGCGCCCACGCAATTTAGCGTTTGCCATTCAGGAGCAGTACC |

Fig. 5E

| ss_12_17 (189) | CAGATATTACCAGATAATCAAAATCACCGGAATAGAAACAAT |
|---|---|
| ss_12_18 (190) | GTATTCTAAGCAGAGAGCCACCACCGGAGGGTTGAATTGCTT |
| ss_12_19 (191) | TTTTAGCGAAGCCCCCTCAGAGCCGCCGGCGGATCAAAATC |
| ss_12_20 (192) | GCGGGAGAATAGCAGAACCGCCACCCTCGCGGGGTTATTCAT |
| ss_12_21 (193) | AATCAAGAATAAGACCACCCTCAGAGCCTCAAGAGCAAAAGA |
| ss_12_22 (194) | TGCACCCAAGAATTGAACCACCACCAGAGTATTAAACATCAA |
| ss_12_23 (195) | CCTGAATAATATCACCAGCATTGACAGGCTATTATTTACATT |
| ss_12_24 (196) | CGAGCGTGTCAGAGGGCAGGTCAGACGAGCCCCCTGAATTAC |
| ss_12_25 (197) | ATTTGCCTAACTGATGATATTCACAAACGTGCCCGACAGTAC |
| ss_12_26 (198) | CAGCCATAAGCGCATCCTCATTAAAGCCGGGTCAGGTGAGTG |
| ss_12_27 (199) | TCCAAATGAGAATAAAAGCGCAGTCTCTTACTGGTTGTAAAT |
| ss_12_28 (200) | TTAGAATCCTTGAAAAATTAATTAATTTTCCC |

Fig. 5F

Table B: Staple sequences modified with different species of overhangs

| Name (SEQ ID NO:) | Sequences |
|---|---|
| Stalk1-ss_2_5 (201) | GAGAGCAGACCTGGAACTCG TT CTTGCAGATAGCCCAATAATT |
| Stalk1-ss_2_6 (202) | GAGAGCAGACCTGGAACTCG TT CTTTTGCAATCCCTCTGTAGC |
| Stalk1-ss_2_7 (203) | GAGAGCAGACCTGGAACTCG TT CAGCAGCTGGTGGTATTAAAT |
| Stalk1-ss_2_8 (204) | GAGAGCAGACCTGGAACTCG TT GAACGAGGCAGGCGACCCGTC |
| Stalk1-ss_2_9 (205) | GAGAGCAGACCTGGAACTCG TT CAGAGGCGGTCCACAACAAAC |
| Stalk1-ss_2_10 (206) | GAGAGCAGACCTGGAACTCG TT ACTTTTCCTGAGAAATGGGA |
| Stalk1-ss_2_11 (207) | GAGAGCAGACCTGGAACTCG TT CATTAAAGATTGCCGTAGATG |
| Stalk1-ss_2_12 (208) | GAGAGCAGACCTGGAACTCG TT AATGCCACCAGTGAGTGCATC |
| Stalk1-ss_2_13 (209) | GAGAGCAGACCTGGAACTCG TT ACCTAAACCAGGGTGACGACG |
| Stalk1-ss_2_14 (210) | GAGAGCAGACCTGGAACTCG TT AGAATACAGGCGGTAGGAAGA |
| Stalk1-ss_2_15 (211) | GAGAGCAGACCTGGAACTCG TT CTTTGACAATCGGCGCTTTCC |
| Stalk1-ss_2_16 (212) | GAGAGCAGACCTGGAACTCG TT CCAAGCGGTCGTGCTGCCGGA |
| Stalk1-ss_2_17 (213) | GAGAGCAGACCTGGAACTCG TT ACGGAGACGCTTTCCCATTCG |
| Stalk3-ss_9_3 (214) | GTCTCGTCGTCTACCGCAAT TT GTAACGATTGGGAACAGCGCC |
| Stalk3-ss_9_4 (215) | GTCTCGTCGTCTACCGCAAT TT CAGACAGATCACCATAGAAAA |
| Stalk3-ss_9_5 (216) | GTCTCGTCGTCTACCGCAAT TT TACAACGATTAGCAAGTTTAT |
| Stalk3-ss_9_6 (217) | GTCTCGTCGTCTACCGCAAT TT AGTTTCGACCAATGACGCAAA |
| Stalk3-ss_9_7 (218) | GTCTCGTCGTCTACCGCAAT TT AACCCATAGCACCGAGGTGGC |
| Stalk3-ss_9_8 (219) | GTCTCGTCGTCTACCGCAAT TT AGGGATAAGAATCAACGTAGA |
| Stalk3-ss_9_9 (220) | GTCTCGTCGTCTACCGCAAT TT AGAGCCAGTCAGACTATTACG |
| Stalk3-ss_9_10 (221) | GTCTCGTCGTCTACCGCAAT TT ACCCTCAATCGGCAACTGGCA |
| Stalk3-ss_9_11 (222) | GTCTCGTCGTCTACCGCAAT TT ACGGCCACCCCTTAAATAACG |
| Stalk3-ss_9_12 (223) | GTCTCGTCGTCTACCGCAAT TT ACCGTACCTTTTCAAGGAAAC |
| Stalk3-ss_9_13 (224) | GTCTCGTCGTCTACCGCAAT TT ATAGCCCGGAACCATAGCCGA |
| Stalk3-ss_9_14 (225) | GTCTCGTCGTCTACCGCAAT TT GTCGAGAACCGCCTTTTTTAA |
| Stalk3-ss_9_15 (226) | GTCTCGTCGTCTACCGCAAT TT AGTACCAACCCTCAATAGCTA |
| ss_3_15-Stalk4 (227) | AAAGGACAGGATTAGATCTAC TT GTCCTTACACAGAGGCTTGA |
| ss_10_14-Stalk5 (228) | AGAAATATAGTATCTCATCGA TT CCGAATGGCATCTGACAGTT |

Table C: Sequences with dye/biotin modifications

| Name (SEQ ID NO:) | Sequences |
|---|---|
| Cy5-Stalk1 comp (229) | /5Cy5/CGAGTTCCAGGTCTGCTCTC |
| Cy3-Stalk 3 comp (230) | /5Cy3/ATTGCGGTAGACGACGAGAC |
| bio-Stalk 4 comp (231) | /biotin/TCAAGCCTCTGTGTAAGGAC |
| bio-Stalk 5 comp (232) | /biotin/AACTGTCAGATGCCATTCGG |

Fig. 5G

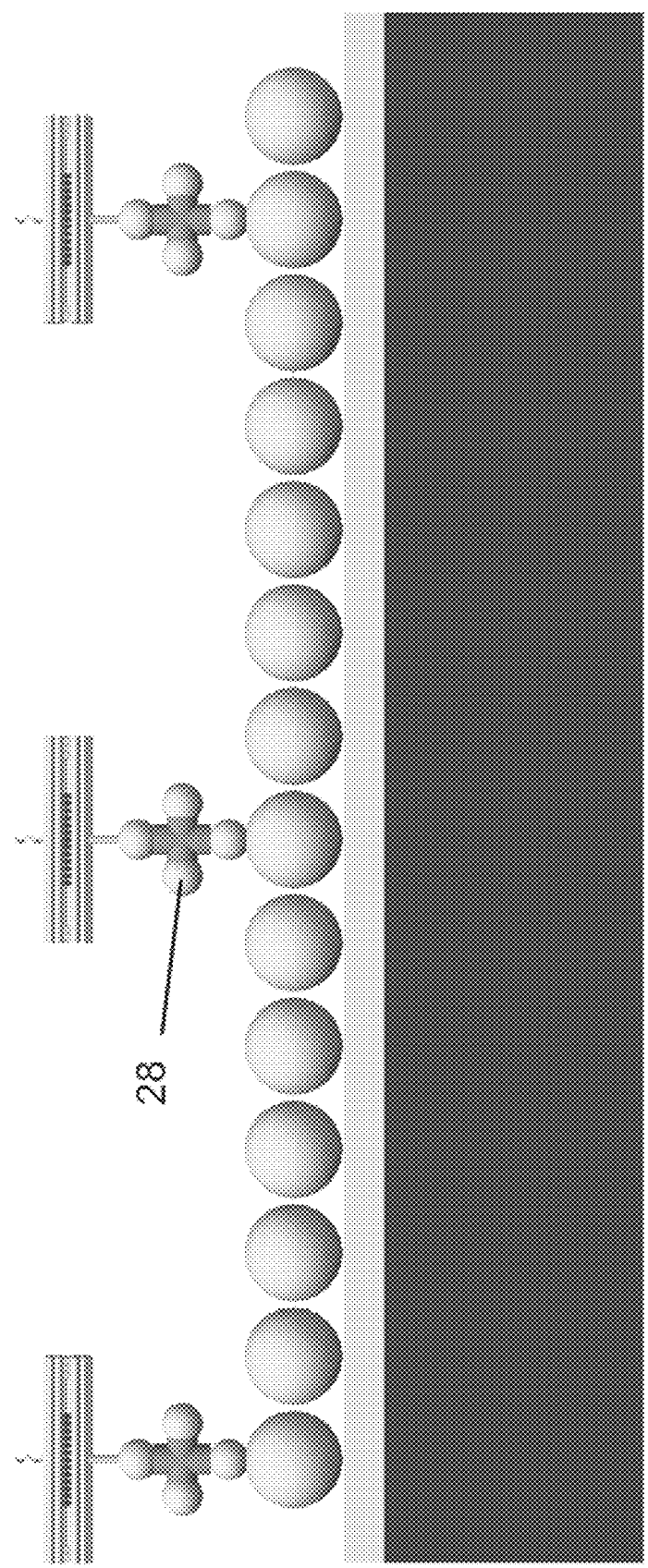

```
AATGCTACTACTATTAGTAGAATTGATGCCACCTTTTCAGCTCGCGCCCCAAATGAAAATATAGCTAAACAGGTTAT
TGACCATTTGCGAAATGTATCTAATGGTCAAACTAAATCTACTCGTTCGCAGAATTGGGAATCAACTGTTATATGGA
ATGAAACTTCCAGACACCGTACTTTAGTTGCATATTTAAAACATGTTGAGCTACAGCATTATATTCAGCAATTAAGC
TCTAAGCCATCCGCAAAAATGACCTCTTATCAAAAGGAGCAATTAAAGGTACTCTCTAATCCTGACCTGTTGGAGTT
TGCTTCCGGTCTGGTTCGCTTTGAAGCTCGAATTAAAACGCGATATTTGAAGTCTTTCGGGCTTCCTCTTAATCTTT
TTGATGCAATCCGCTTTGCTTCTGACTATAATAGTCAGGGTAAAGACCTGATTTTTGATTTATGGTCATTCTCGTTT
TCTGAACTGTTTAAAGCATTTGAGGGGGATTCAATGAATATTTATGACGATTCCGCAGTATTGGACGCTATCCAGTC
TAAACATTTTACTATTACCCCCTCTGGCAAAACTTCTTTTGCAAAAGCCTCTCGCTATTTTGGTTTTTATCGTCGTC
TGGTAAACGAGGGTTATGATAGTGTTGCTCTTACTATGCCTCGTAATTCCTTTTGGCGTTATGTATCTGCATTAGTT
GAATGTGGTATTCCTAAATCTCAACTGATGAATCTTTCTACCTGTAATAATGTTGTTCCGTTAGTTCGTTTTATTAA
CGTAGATTTTTCTTCCCAACGTCCTGACTGGTATAATGAGCCAGTTCTTAAAATCGCATAAGGTAATTCACAATGAT
TAAAGTTGAAATTAAACCATCTCAAGCCCAATTTACTACTCGTTCTGGTGTTTCTCGTCAGGGCAAGCCTTATTCAC
TGAATGAGCAGCTTTGTTACGTTGATTTGGGTAATGAATATCCGGTTCTTGTCAAGATTACTCTTGATGAAGGTCAG
CCAGCCTATGCGCCTGGTCTGTACACCGTTCATCTGTCCTCTTTCAAAGTTGGTCAGTTCGGTTCCCTTATGATTGA
CCGTCTGCGCCTCGTTCCGGCTAAGTAACATGGAGCAGGTCGCGGATTTCGACACAATTTATCAGGCGATGATACAA
ATCTCCGTTGTACTTTGTTTCGCGCTTGGTATAATCGCTGGGGGTCAAAGATGAGTGTTTTAGTGTATTCTTTTGCC
TCTTTCGTTTTAGGTTGGTGCCTTCGTAGTGGCATTACGTATTTTACCCGTTTAATGGAAACTTCCTCATGAAAAAG
TCTTTAGTCCTCAAAGCCTCTGTAGCCGTTGCTACCCTCGTTCCGATGCTGTCTTTCGCTGCTGAGGGTGACGATCC
CGCAAAAGCGGCCTTTAACTCCCTGCAAGCCTCAGCGACCGAATATATCGGTTATGCGTGGGCGATGGTTGTTGTCA
TTGTCGGCGCAACTATCGGTATCAAGCTGTTTAAGAAATTCACCTCGAAAGCAAGCTGATAAACCGATACAATTAAA
GGCTCCTTTTGGAGCCTTTTTTTTGGAGATTTTCAACGTGAAAAAATTATTATTCGCAATTCCTTTAGTTGTTCCTT
TCTATTCTCACTCCGCTGAAACTGTTGAAAGTTGTTTAGCAAAATCCCATACAGAAAATTCATTTACTAACGTCTGG
AAAGACGACAAAACTTTAGATCGTTACGCTAACTATGAGGGCTGTCTGTGGAATGCTACAGGCGTTGTAGTTTGTAC
TGGTGACGAAACTCAGTGTTACGGTACATGGGTTCCTATTGGGCTTGCTATCCCTGAAAATGAGGGTGGTGGCTCTG
AGGGTGGCGGTTCTGAGGGTGGCGGTTCTGAGGGTGGCGGTACTAAACCTCCTGAGTACGGTGATACACCTATTCCG
GGCTATACTTATATCAACCCTCTCGACGGCACTTATCCGCCTGGTACTGAGCAAAACCCCGCTAATCCTAATCCTTC
TCTTGAGGAGTCTCAGCCTCTTAATACTTTCATGTTTCAGAATAATAGGTTCCGAAATAGGCAGGGGGCATTAACTG
TTTATACGGGCACTGTTACTCAAGGCACTGACCCCGTTAAAACTTATTACCAGTACACTCCTGTATCATCAAAAGCC
ATGTATGACGCTTACTGGAACGGTAAATTCAGAGACTGCGCTTTCCATTCTGGCTTTAATGAGGATTTATTTGTTTG
TGAATATCAAGGCCAATCGTCTGACCTGCCTCAACCTCCTGTCAATGCTGGCGGCGGCTCTGGTGGTGGTTCTGGTG
GCGGCTCTGAGGGTGGTGGCTCTGAGGGTGGCGGTTCTGAGGGTGGCGGCTCTGAGGGAGGCGGTTCCGGTGGTGGC
TCTGGTTCCGGTGATTTTGATTATGAAAAGATGGCAAACGCTAATAAGGGGGCTATGACCGAAAATGCCGATGAAAA
CGCGCTACAGTCTGACGCTAAAGGCAAACTTGATTCTGTCGCTACTGATTACGGTGCTGCTATCGATGGTTTCATTG
GTGACGTTTCCGGCCTTGCTAATGGTAATGGTGCTACTGGTGATTTTGCTGGCTCTAATTCCCAAATGGCTCAAGTC
GGTGACGGTGATAATTCACCTTTAATGAATAATTTCCGTCAATATTTACCTTCCCTCCCTCAATCGGTTGAATGTCG
CCCTTTTGTCTTTGGCGCTGGTAAACCATATGAATTTTCTATTGATTGTGACAAAATAAACTTATTCCGTGGTGTCT
TTGCGTTTCTTTTATATGTTGCCACCTTTATGTATGTATTTTCTACGTTTGCTAACATACTGCGTAATAAGGAGTCT
TAATCATGCCAGTTCTTTTGGGTATTCCGTTATTATTGCGTTTCCTCGGTTTCCTTCTGGTAACTTTGTTCGGCTAT
CTGCTTACTTTTCTTAAAAGGGCTTCGGTAAGATAGCTATTGCTATTTCATTGTTTCTTGCTCTTATTATTGGGCT
TAACTCAATTCTTGTGGGTTATCTCTCTGATATTAGCGCTCAATTACCCTCTGACTTTGTTCAGGGTGTTCAGTTAA
TTCTCCCGTCTAATGCGCTTCCCTGTTTTATGTTATTCTCTCTGTAAAGGCTGCTATTTTCATTTTGACGTTAAA
CAAAAAATCGTTTCTTATTTGGATTGGGATAAATAATATGGCTGTTTATTTTGTAACTGGCAAATTAGGCTCTGGAA
AGACGCTCGTTAGCGTTGGTAAGATTCAGGATAAAATTGTAGCTGGGTGCAAAATAGCAACTAATCTTGATTTAAGG
CTTCAAAACCTCCCGCAAGTCGGGAGGTTCGCTAAAACGCCTCGCGTTCTTAGAATACCGGATAAGCCTTCTATATC
TGATTTGCTTGCTATTGGGCGCGGTAATGATTCCTACGATGAAAATAAAAACGGCTTGCTTGTTCTCGATGAGTGCG
GTACTTGGTTTAATACCCGTTCTTGGAATGATAAGGAAAGACAGCCGATTATTGATTGGTTTCTACATGCTCGTAAA
TTAGGATGGGATATTATTTTTCTTGTTCAGGACTTATCTATTGTTGATAAACAGGCGCGTTCTGCATTAGCTGAACA
TGTTGTTTATTGTCGTCGTCTGGACAGAATTACTTTACCTTTTGTCGGTACTTTATATTCTCTTATTACTGGCTCGA
AAATGCCTCTGCCTAAATTACATGTTGGCGTTGTTAAATATGGCGATTCTCAATTAAGCCCTACTGTTGAGCGTTGG
CTTTATACTGGTAAGAATTTGTATAACGCATATGATACTAAACAGGCTTTTTCTAGTAATTATGATTCCGGTGTTTA
TTCTTATTTAACGCCTTATTTATCACACGGTCGGTATTTCAAACCATTAAATTTAGGTCAGAAGATGAAATTAACTA
AAATATATTTGAAAAAGTTTTCTCGCGTTCTTTGTCTTGCGATTGGATTTGCATCAGCATTTACATATAGTTATATA
ACCCAACCTAAGCCGGAGGTTAAAAAGGTAGTCTCTCAGACCTATGATTTTGATAAATTCACTATTGACTCTTCTCA
GCGTCTTAATCTAAGCTATCGCTATGTTTTCAAGGATTCTAAGGGAAAATTAATTAATAGCGACGATTTACAGAAGC
```

Fig. 8A

```
AAGGTTATTCACTCACATATATTGATTTATGTACTGTTTCCATTAAAAAAGGTAATTCAAATGAAATTGTTAAATGT
AATTAATTTTGTTTTCTTGATGTTTGTTTCATCATCTTCTTTTGCTCAGGTAATTGAAATGAATAATTCGCCTCTGC
GCGATTTTGTAACTTGGTATTCAAAGCAATCAGGCGAATCCGTTATTGTTTCTCCCGATGTAAAAGGTACTGTTACT
GTATATTCATCTGACGTTAAACCTGAAAATCTACGCAATTTCTTTATTTCTGTTTTACGTGCAAATAATTTTGATAT
GGTAGGTTCTAACCCTTCCATTATTCAGAAGTATAATCCAAACAATCAGGATTATATTGATGAATTGCCATCATCTG
ATAATCAGGAATATGATGATAATTCCGCTCCTTCTGGTGGTTTCTTTGTTCCGCAAAATGATAATGTTACTCAAACT
TTTAAAATTAATAACGTTCGGGCAAAGGATTTAATACGAGTTGTCGAATTGTTTGTAAAGTCTAATACTTCTAAATC
CTCAAATGTATTATCTATTGACGGCTCTAATCTATTAGTTGTTAGTGCTCCTAAAGATATTTTAGATAACCTTCCTC
AATTCCTTTCAACTGTTGATTTGCCAACTGACCAGATATTGATTGAGGGTTTGATATTTGAGGTTCAGCAAGGTGAT
GCTTTAGATTTTCATTTGCTGCTGGCTCTCAGCGTGGCACTGTTGCAGGCGGTGTTAATACTGACCGCCTCACCTC
TGTTTTATCTTCTGCTGGTGGTTCGTTCGGTATTTTTAATGGCGATGTTTTAGGGCTATCAGTTCGCGCATTAAAGA
CTAATAGCCATTCAAAAATATTGTCTGTGCCACGTATTCTTACGCTTTCAGGTCAGAAGGGTTCTATCTCTGTTGGC
CAGAATGTCCCTTTTATTACTGGTCGTGTGACTGGTGAATCTGCCAATGTAAATAATCCATTTCAGACGATTGAGCG
TCAAAATGTAGGTATTTCCATGAGCGTTTTCCTGTTGCAATGGCTGGCGGTAATATTGTTCTGGATATTACCAGCA
AGGCCGATAGTTTGAGTTCTTCTACTCAGGCAAGTGATGTTATTACTAATCAAAGAAGTATTGCTACAACGGTTAAT
TTGCGTGATGGACAGACTCTTTTACTCGGTGGCCTCACTGATTATAAAAACACTTCTCAGGATTCTGGCGTACCGTT
CCTGTCTAAAATCCCTTTAATCGGCCTCCTGTTTAGCTCCCGCTCTGATTCTAACGAGGAAAGCACGTTATACGTGC
TCGTCAAAGCAACCATAGTACGCGCCCTGTAGCGGCGCATTAAGCGCGGCGGGTGTGGTGGTTACGCGCAGCGTGAC
CGCTACACTTGCCAGCGCCCTAGCGCCCGCTCCTTTCGCTTTCTTCCCTTCCTTTCTCGCCACGTTCGCCGGCTTTC
CCCGTCAAGCTCTAAATCGGGGGCTCCCTTTAGGGTTCCGATTTAGTGCTTTACGGCACCTCGACCCCAAAAAACTT
GATTTGGGTGATGGTTCACGTAGTGGGCCATCGCCCTGATAGACGGTTTTTCGCCCTTTGACGTTGGAGTCCACGTT
CTTTAATAGTGGACTCTTGTTCCAAACTGGAACAACACTCAACCCTATCTCGGGCTATTCTTTTGATTTATAAGGGA
TTTTGCCGATTTCGGAACCACCATCAAACAGGATTTTCGCCTGCTGGGGCAAACCAGCGTGGACCGCTTGCTGCAAC
TCTCTCAGGGCCAGGCGGTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAGGTTTCCCGACTGGAAAG
CGGGCAGTGAGCGCAACGCAATTAATGTGAGTTAGCTCACTCATTAGGCACCCCAGGCTTTACACTTTATGCTTCCG
GCTCGTATGTTGTGTGGAATTGTGAGCGGATAACAATTTCACACAGGAAACAGCTATGACCATGATTACGAATTCGA
GCTCGGTACCCGGGGATCCTCTAGAGTCGACCTGCAGGCATGCAAGCTTGGCACTGGCCGTCGTTTTACAACGTCGT
GACTGGGAAAACCCTGGCGTTACCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATGGCGCTTTGCCTGGTTTCCGGCAC
CAGAAGCGGTGCCGGAAAGCTGGCTGGAGTGCGATCTTCCTGAGGCCGATACTGTCGTCGTCCCCTCAAACTGGCAG
ATGCACGGTTACGATGCGCCCATCTACACCAACGTGACCTATCCCATTACGGTCAATCCGCCGTTTGTTCCCACGGA
GAATCCGACGGGTTGTTACTCGCTCACATTTAATGTTGATGAAAGCTGGCTACAGGAAGGCCAGACGCGAATTATTT
TTGATGGCGTTCCTATTGGTTAAAAAATGAGCTGATTTAACAAAAATTTAATGCGAATTTTAACAAAATATTAACGT
TTACAATTTAAATATTTGCTTATACAATCTTCCTGTTTTTGGGGCTTTTCTGATTATCAACCGGGGTACATATGATT
GACATGCTAGTTTTACGATTACCGTTCATCGATTCTCTTGTTTGCTCCAGACTCTCAGGCAATGACCTGATAGCCTT
TGTAGATCTCTCAAAAATAGCTACCCTCTCCGGCATTAATTTATCAGCTAGAACGGTTGAATATCATATTGATGGTG
ATTTGACTGTCTCCGGCCTTTCTCACCCTTTTGAATCTTTACCTACACATTACTCAGGCATTGCATTTAAAATATAT
GAGGGTTCTAAAAATTTTTATCCTTGCGTTGAAATAAAGGCTTCTCCCGCAAAAGTATTACAGGGTCATAATGTTTT
TGGTACAACCGATTTAGCTTTATGCTCTGAGGCTTTATTGCTTAATTTTGCTAATTCTTTGCCTTGCCTGTATGATT
TATTGGATGTT
```

Fig. 8B

MICROMECHANICAL DNA ORIGAMI FORCE SENSOR

CROSS REFERENCE TO RELATED APPLICATIONS

This application claims the benefit of U.S. Provisional Patent Application No. 62/922,963 filed Sep. 6, 2019, which is incorporated herein by reference in its entirety.

STATEMENT REGARDING FEDERAL FUNDING

This invention was made with Government support under Grant No. FA9550-18-1-0199 awarded by the U.S. Air Force, Air Force Research Laboratory. The Government has certain rights in this invention.

REFERENCE TO A SEQUENCE LISTING SUBMITTED VIA EFS-WEB

The content of the ASCII text file of the sequence listing named "6526_2004904_ST25" which is 54,500 bytes in size was created on Aug. 28, 2020 and electronically submitted via EFS-Web herewith the application is incorporated herein by reference in its entirety.

Provided herein are nanoscale, fluorescent force sensors and uses for the force sensors.

Despite the prevalence of congenital heart disease, mechanical forces during development, particularly during valvulogenesis, cannot be directly measured and are not well understood. One-percent of live births are affected by some form of congenital heart disease (CHD) making it the most common human birth defect, and biomechanical forces like wall shear stress (WSS) have been shown to be critical morphogens during embryonic cardiac development. To date, in vivo direct studies of WSS have not been possible. Instead, the most promising existing techniques rely on indirect methods, like micron resolution particle image velocimetry, (pPIV), for assessing flow velocity profiles coupled with high-speed, high-resolution geometric imaging to estimate WSS. Further, while zebrafish provide powerful cardiac disease models, the mechanisms by which early heart structures give rise to valve leaflets and regulate their development are unknown. Due to the rapid deformations, small size, and dynamic fluid environment, it is not possible to gather the detailed time-resolved structural and flow information required to estimate WSS throughout embryonic valvulogensis using existing flow-based techniques like pPIV.

In medical clinics, direct measurement of WSS would provide a groundbreaking tool for the planning of surgical interventions. This process, particularly in children, is challenging because physicians have no reference by which to predict valve disease progression based on early valve function. No baseline "maps" of developmental WSS currently exist for hearts with healthy and diseased valves. Such maps could offer surgeons powerful insight into the current severity of a malformation and predict outcomes for malformations based on patients with similarly disrupted WSS distributions. Nanosensors effective for quantifying piconewton– (pN–) scale forces are needed to effectively evaluate forces in Biosystems at the cellular level.

SUMMARY

In one aspect or embodiment, a micromechanical spring sensor is provided. The sensor comprises:

a spring element comprising a nucleic acid and/or nucleic acid analog nanostructure beam pair comprising one or more single-stranded scaffold nucleic acids or nucleic acid analogs, and nucleic acids or nucleic acid analog staples, comprising:
  a flexible first beam and a flexible second beam pinned together at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;
  a first tether attached to the first beam at the unpinned section; and
  a second tether attached to the second beam at the unpinned section;
wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties for at least one pair of corresponding donor and acceptor moieties, such that the sensor produces a detectably different emission spectra when the beams are in the closed position as compared to when the beams are in the open position; and
  a drag element attached to a tether of one of the beam pairs.

In another aspect or embodiment, a micromechanical spring sensor is provided. The sensor comprises:

a spring element comprising a nucleic acid and/or nucleic acid origami beam pair comprising one or more single-stranded scaffold nucleic acids or nucleic acid analogs, and nucleic acids or nucleic acid analog staples, comprising:
  a flexible first beam and a flexible second beam pinned together by pinning staples at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;
  a first tether attached to the first beam at the unpinned section; and
  a second tether attached to the second beam at the unpinned section;
wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties for at least one pair of corresponding donor and acceptor moieties, such that the sensor produces a detectably different emission spectra when the beams are in the closed position as compared to when the beams are in the open position; and a drag element attached to a tether of one of the beam pairs.

In another aspect or embodiment, a method of measuring a force is provided. The method comprises:

exposing a sensor as described in the preceding paragraphs to an environment in which a force is to be measured;

illuminating the sensor with electromagnetic radiation within the absorption spectrum of the donor: and;

determining, by measuring emission from the sensor in the emission spectrum of the donor or acceptor, either if a force acts on the sensor in the environment sufficient to flex the beams of the sensor into an open position, and/or the extent of flexing of the beams of the sensor to quantify the force acting on the sensor in the environment.

The following numbered clauses provide various aspects, embodiments, and/or examples of the present invention:

Clause 1. A micromechanical spring sensor, comprising:

a spring element comprising a nucleic acid and/or nucleic acid analog nanostructure beam pair comprising one or more single-stranded scaffold nucleic acids or nucleic acid analogs, and nucleic acids or nucleic acid analog staples, comprising:

a flexible first beam and a flexible second beam pinned together at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;

a first tether attached to the first beam at the unpinned section; and a second tether attached to the second beam at the unpinned section;

wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties for at least one pair of corresponding donor and acceptor moieties, such that the sensor produces a detectably different emission spectra when the beams are in the closed position as compared to when the beams are in the open position; and a drag element attached to a tether of one of the beam pairs.

Clause 2. A micromechanical spring sensor, comprising:

a spring element comprising a nucleic acid and/or nucleic acid origami beam pair comprising one or more single-stranded scaffold nucleic acids or nucleic acid analogs, and nucleic acids or nucleic acid analog staples, comprising:

a flexible first beam and a flexible second beam pinned together by pinning staples at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;

a first tether attached to the first beam at the unpinned section; and a second tether attached to the second beam at the unpinned section;

wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties for at least one pair of corresponding donor and acceptor moieties, such that the sensor produces a detectably different emission spectra when the beams are in the closed position as compared to when the beams are in the open position; and a drag element attached to a tether of one of the beam pairs.

Clause 3. The sensor of clause 1 or 2, wherein the resting gap distance between the fluorescent donor moieties and the quenching acceptor moieties is less than a Förster critical distance for the donors and acceptors, and the tensioned gap distance between the fluorescent donor moieties and the quenching acceptor moieties is greater than the Förster critical distance for at least one pair of corresponding donor and acceptor moieties, such that the sensor produces a detectably different emission spectra when the beams are in the closed position as compared to when the beams are in the open position.

Clause 4. The sensor of any one of clauses 1-3, wherein one or both of the beams are bundles of 2 or more double-stranded nucleic acid and/or nucleic acid analog helices.

Clause 5. The sensor of any one of clauses 1-4, wherein at least two sets of the corresponding donor and acceptor moieties are arranged in the unpinned section such that different tensional forces applied to the tethers results in different tensioned gap distances for at least two of the corresponding donor and acceptor moieties, such that different positive tensions applied to the tethers produce different emission spectra.

Clause 6. The sensor of clause 5, wherein the at least two pairs of the corresponding donor and acceptor moieties are arranged in the unpinned section to produce a regular change in the emission of the sensor with a regular increase in tension applied to the tethers.

Clause 7. The sensor of any one of clauses 1-6, comprising at least five pairs of the corresponding donor and acceptor moieties arranged in the unpinned section.

Clause 8. The sensor of any one of clauses 1-7, further comprising a ligand indirectly or directly attached to the first tether or the second tether.

Clause 9. The sensor of clause 8, wherein the ligand is an antibody, an antibody fragment, or a lectin.

Clause 10. The sensor of any one of clauses 1-7, further comprising biotin linked to the first tether or the second tether.

Clause 11. The sensor of any one of clauses 1-7, wherein the first tether or the second tether comprise an aptamer.

Clause 12. The sensor of any one of clauses 1-11, wherein the drag element is a DNA origami or single-strand tile structure.

Clause 13. The sensor of clause 12, wherein the drag element is a plate.

Clause 14. The sensor of any one of clauses 1-11, wherein the drag element comprises a bead or particle.

Clause 15. The sensor of any one of clauses 1-14, wherein the drag element is a particle that renders the sensor neutrally buoyant or buoyant.

Clause 16. The sensor of any one of clauses 1-14, wherein the drag element is attached to the spring element by a biotin/streptavidin linkage.

Clause 17. The sensor of any one of clauses 1-16, wherein the first tether or the second tether anchors the sensor to a surface of a substrate.

Clause 18. The sensor of any one of clauses 1-16, wherein the first tether or the second tether anchors the sensor to a cell or tissue.

Clause 19. The sensor of clause 18, wherein the cell or tissue is located in an organism.

Clause 20. The sensor of clause 19, wherein the cell or tissue is located in a microfluidic chamber.

Clause 21. The sensor of any one of clauses 1-20, wherein the fluorescent donor moieties and/or acceptor moieties are a fluorescent protein.

Clause 22. A method of measuring a force, comprising:
exposing the sensor of any one of clauses 1-21 to an environment in which a force is to be measured;
illuminating the sensor with electromagnetic radiation within the absorption spectrum of the donor: and;
determining, by measuring emission from the sensor in the emission spectrum of the donor or acceptor, either if a force acts on the sensor in the environment sufficient to flex the beams of the sensor into an open position, and/or the extent of flexing of the beams of the sensor to quantify the force acting on the sensor in the environment.

Clause 23. The method of clause 22, wherein the sensor is calibrated to correlate the extent of flexing of the beams of the sensor with force acting on the sensor in an environment.

Clause 24. The method of clause 22, wherein the sensor is anchored by the first tether or the second tether to a cell or tissue.

Clause 25. The method of clause 22, wherein the sensor comprises a lipophilic anchor attached to the first tether or the second tether.

Clause 26. The method of clause 22, wherein the sensor comprises a lectin, antibody, or antibody fragment attached to the first tether or the second tether for targeting the sensor to a target cell or tissue.

Clause 27. The method of any one of clauses 20-26, wherein the environment is in vivo.

Clause 28. The method of any one of clauses 20-26 wherein the sensor is attached to a cell or tissue of a zebrafish embryo.

Clause 29. The method of any one of clauses 20-26, wherein the sensor is attached to a surface or a substrate.

Clause 30. The method of any one of clauses 20-26, wherein the environment is a cell culture vessel comprising a cell or tissue, and the sensor is attached by the first tether or second tether to the cell or tissue.

Clause 31. The method of any one of clauses 20-30, comprising imaging the cell or tissue at a wavelength within the emission spectrum of the donor or acceptor to evaluate forces acting on the sensors.

Clause 32. The method of clause 22, wherein the environment is a liquid, and liquid movement in the liquid is quantified or imaged at a wavelength within the emission spectrum of the donor or acceptor.

BRIEF DESCRIPTION OF THE DRAWINGS

FIGS. 5A-5G provide Tables A-C, listing DNA origami staples used to produce the sensor described in Example 3. Pinning staples are highlighted.

FIGS. 6A-6E provide schematic diagrams demonstrating the assembly of the shear sensor to a flow channel.

FIGS. 8A-8B, taken continuously, provide an exemplary nucleotide sequence for M13mp18 (SEQ ID NO: 233, Bayou Biolabs).

DETAILED DESCRIPTION

Figure 1:
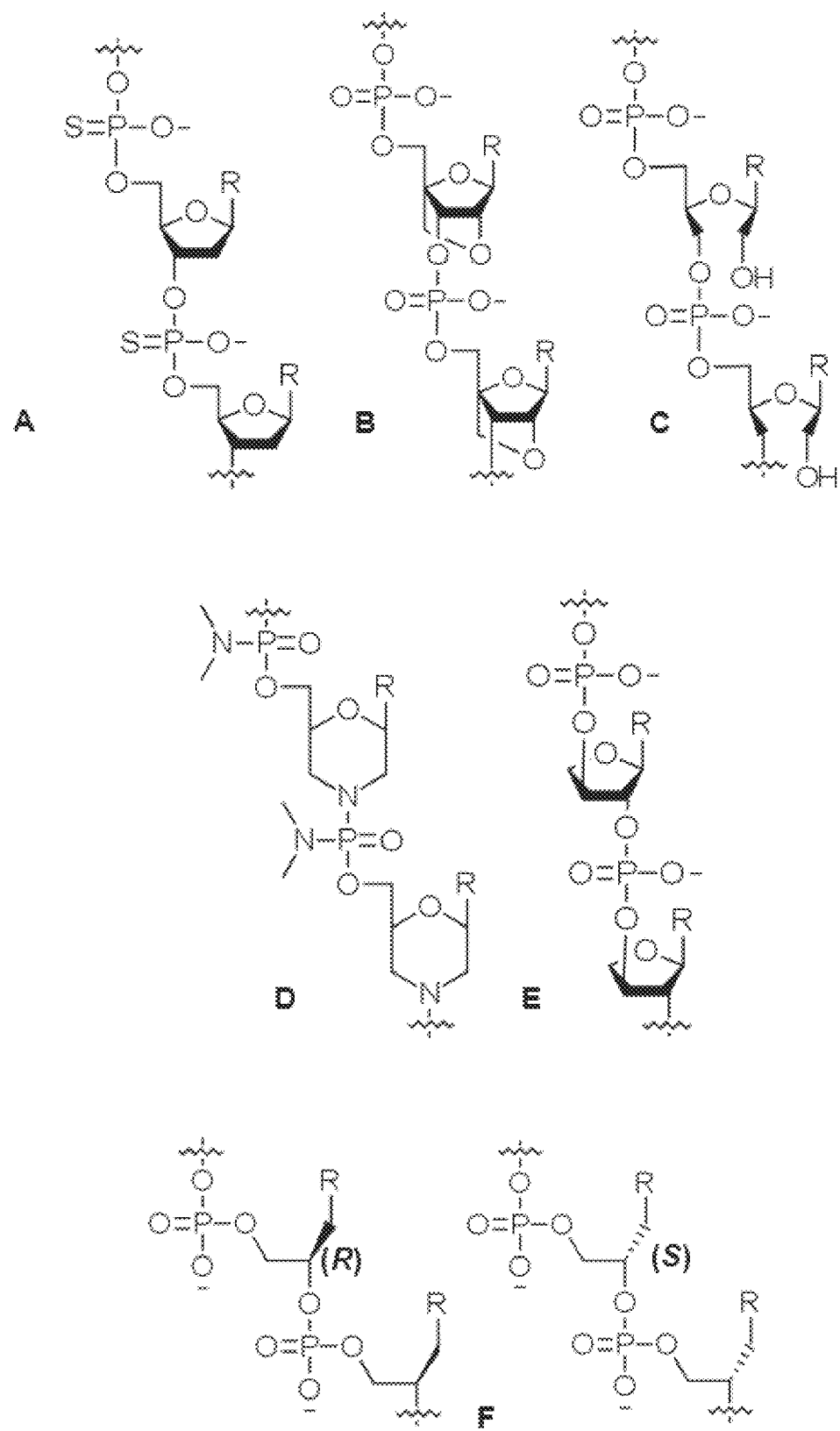
FIG. 1 provides various examples of nucleic acid modifications.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more. A "plurality" is two or more.

As used herein, the term "comprising" is open-ended and may be synonymous with "including", "containing", or "characterized by". The term "consisting essentially of" limits the scope of a claim to the specified materials or steps and those that do not materially affect basic and novel characteristic(s). The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

As used herein, the term "nucleic acid" refers to deoxyribonucleic acids (DNA) and ribonucleic acids (RNA). Nucleic acids may comprise modified bases, such as, for example and without limitation: 2'-O-methyl-substituted RNA, locked nucleic acids, unlocked nucleic acids, triazole-linked DNA, peptide nucleic acids including γPNA, morpholino oligomers, dideoxynucleotide oligomers, glycol nucleic acids, threose nucleic acids and combinations thereof including, but not limited to, ribonucleotide or deoxyribonucleotide residue(s). Herein, "nucleic acid" and "oligonucleotide," in reference to nucleic acids, are used interchangeably, and can refer to a short, single-stranded structure made of up nucleotides. An oligonucleotide may be referred to by the length (i.e. number of nucleotides) of the strand, through the nomenclature "-mer". For example, an oligonucleotide of 22 nucleotides would be referred to as a 22-mer. All nucleotide sequences are provided in a 5' to 3' direction, left to right, unless indicated otherwise.

A "nucleic acid analog" can be a composition comprising a sequence of nucleobases arranged on a substrate, such as a polymeric backbone, and can bind DNA and/or RNA by hybridization by Watson-Crick, or Watson-Crick-like hydrogen bond base pairing. Non-limiting examples of common nucleic acid analogs include peptide nucleic acids (PNAs), such as γPNA, morpholino nucleic acids, phosphorothioates, locked nucleic acid (2'-O-4'-C-methylene bridge, including, but not limited to, oxy, thio or amino versions thereof), unlocked nucleic acid (the C2'-C3' bond is cleaved), 2'-O-methyl-substituted RNA, threose nucleic acid, glycol nucleic acid, etc.

A conformationally preorganized nucleic acid analog can be a nucleic acid analog that has a backbone (a preorganized backbone) that forms either a right-handed helix or a left-handed helix, depending on the structure of the nucleic acid backbone. One example of a conformationally preorganized nucleic acid analog is γPNA, which has a chiral center at the γ carbon, and, depending on, and due to, the chirality of the groups at the γ carbon, forms a right-handed helix or a left-handed helix. Likewise, locked nucleic acids can comprise a ribose with a bridge between the 2' oxygen and the 4' carbon, which "locks" the ribose into a 3'-endo (North) conformation.

In the context of the present disclosure, a "nucleotide" may refer to a monomer comprising at least one nucleobase and a backbone element (backbone moiety), which in a nucleic acid, such as RNA or DNA, is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked or protected amines. A "nucleotide residue" may refer to a single nucleotide that is incorporated into an oligonucleotide or polynucleotide. A nucleic acid or a nucleic acid analog may comprise a sequence of nucleobases, referred to herein as a binding domain, that is able to hybridize to (e.g., bind to) a complementary nucleic acid or nucleic acid analog sequence, e.g., a complementary binding domain or binding partner, on a nucleic acid by cooperative base pairing, e.g., Watson-Crick base pairing or Watson-Crick-like base pairing. Complementary binding domains may be referred to individually as binding partners, and together as a binding pair.

In further detail, nucleotides, for either RNA, DNA, or nucleic acid analogs, can have the structure A-B wherein A is a backbone monomer moiety and B is a nucleobase as described herein. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). In one example the backbone monomer is a ribose mono-, di-, or tri-phosphate or a deoxyribose mono-, di-, or tri-phosphate, such as a 5' monophosphate, diphosphate, or triphosphate of ribose or deoxyribose. The backbone monomer can include both the structural "residue" component, such as the ribose in RNA, and any active groups that are modified in linking monomers together, such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl)glycine backbone monomer can be condensed during polymerization to leave a peptide (amide) bond. The active groups can be phosphoramidite groups useful for phosphoramidite oligomer synthesis. The nucleotide also optionally may comprise one or more protecting groups, such as 4,4'-dimethoxytrityl (DMT). A number of additional methods of preparing synthetic nucleic acids or nucleic acid analogs depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the field of nucleic acid and nucleic acid analog oligomer synthesis.

Non-limiting examples of common nucleic acid modifications for production of modified nucleic acids, e.g. nucleic acid analogs, include peptide nucleic acids, such as γPNA, phosphorothioate (e.g., FIG. 1 (A)), locked nucleic acid (2'-O-4'-C-methylene bridge, including, but not limited to, oxy, thio or amino versions thereof, (e.g., FIG. 1 (B)), unlocked nucleic acid (the C2'-C3' bond is cleaved, e.g., FIG. 1 (C)), 2'-O-methyl-substituted RNA, morpholino nucleic acid (e.g., FIG. 1 (D)), threose nucleic acid (e.g., FIG. 1 (E)), glycol nucleic acid (e.g., FIG. 1 (F), showing R and S Forms), phosphorodiamidate morpholino oligomer (PMO). FIG. 1 (A-F) shows monomer structures for various examples of nucleic acid analogs. FIG. 1 (A-F) each show two monomer residues incorporated into a longer chain as indicated by the wavy lines. Incorporated monomers are referred to herein as "residues" and the part of the nucleic acid or nucleic acid analog excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and, thus, the backbone monomer is ribose triphosphate prior to incorporation and a ribose monophosphate residue after incorporation. Like γPNA, Locked Nucleic Acid (e.g., FIG. 1 (B)) is conformationally preorganized. A modified nucleic acid include natural residues, e.g. natural RNA or DNA nucleosides or nucleotides, with one or more modified nucleoside or nucleotide residues. A nucleic acid analog may be a modified nucleic acid, but also includes compounds that do not contain natural RNA or DNA nucleosides, such as PNAs.

A "moiety" is a part of a molecule, and can include as a class "residues", which are the portion of a compound or monomer that remains in a larger molecule, such as a polymer chain, after incorporation of that compound or monomer into the larger molecule, such as a nucleotide as-incorporated into a nucleic acid or an amino acid as-incorporated into a polypeptide or protein. Fluorescent moieties include chromophores and fluorescent proteins covalently linked to a stated molecule, such as a pendant portion or tether of a staple nucleic acid used to form a DNA origami structure.

The term "polymer composition" may be a composition comprising one or more polymers. As a class, "polymers" can include, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" can be a polymer that comprises a small number of monomers, such as, for example, from 3 to 100 monomer residues. As such, the term "polymer" can include oligomers. The terms "nucleic acid" and "nucleic acid analog" can include nucleic acid and nucleic acid polymers and oligomers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or certain groups are removed in the polymerization process. A polymer is said to comprise a specific type of linkage if that linkage is present in the polymer. An incorporated monomer can be a "residue". A typical monomer for a nucleic acid or nucleic acid analog is referred to as a nucleotide.

Complementary refers to the ability of polynucleotides (nucleic acids and nucleic acid analogs) to hybridize (anneal) to one another, forming inter-strand base pairs. Annealing is temperature-dependent, and complementary strands anneal at a temperature below the melting temperature (Tm) for the strands, which depends on, for example, the respective nucleobase sequences of the strands, the length of the complementary sequences, the solvent in which the strands are dissolved, and the backbone structure of the strands. Base pairs are formed by hydrogen bonding between nucleotide units in polynucleotide or polynucleotide analog strands that are typically in antiparallel orientation. Complementary polynucleotide strands can base pair (hybridize) in the Watson-Crick manner (e.g., A to T, A to U, C to G), or in any other manner that allows for the formation of duplexes. In RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline, in a polar aprotic solvent or polar aprotic organic solvent, such as DMSO and/or DMF, optionally in the presence of an anionic surfactant, as described herein, or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be "fully complementary", though one sequence (e.g., a target sequence in an mRNA) may be longer than the other.

A moiety in a compound, such as a fluorophore or ligand such as biotin, can be covalently attached to the nucleic acid or nucleic acid analog backbone, and, thus, is said to be "linked" to the backbone. Depending on the chemistry used to prepare the compound, the linkage may be direct, or through a "linker" which is a moiety that covalently attaches two other moieties or groups. The linkers are non-bulky in that they do not sterically hinder or otherwise interfere to any substantial extent with the formation of a DNA origami structure. The linker, when incorporated into a compound is the remaining moiety or residue resulting from the linking.

A linker or linking group may be an organic moiety that connects two parts of a compound, e.g., covalently attaches two parts of a compound, such as, for example and without limitation, connection of a ligand or fluorophore to the backbone of the nucleic acid or nucleic acid analog. Linkers typically comprise a direct bond or an atom such as oxygen, nitrogen, phosphorus, or sulfur, a unit such as, C(O), C(O) NH, SO, $SO_2$, $SO_2NH$, or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (CH=) is optionally interrupted or terminated by a hetero atom, such as O, S, or N, substituted or unsubstituted aryl, substituted or unsubstituted heteroaryl, substituted or unsubstituted heterocyclic. In one aspect, the linker may comprise or consist of between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., 0, P, N, or S atoms. The linker may have a molecular weight, based on the atomic mass of its constituent atoms, of less than 500 Daltons (Da) or less than 400 Da.

The linker may be a non-reactive moiety that links the group to the backbone, and can include from 1-10 carbon atoms ($C_1$-$C_{10}$), optionally substituted with a hetero-atom, such as a N, S, or O, or a non-reactive linkage, such as an amide linkage (peptide bond) formed by reacting an amine with a carboxyl group. Examples of $C_1$-$C_{10}$ alkylenes include linear or branched, alkylene (bivalent) moieties such as a methylene, ethylene, trimethylene, tetramethylene, pentamethylene, hexamethylene, hepamethylene, octamethylene, nonamethylene, or decamethylene moieties (e.g., $CH_2$—$[CH_2]_n$—, where n ranges from 1 to 9). The linkers may comprise from one to four ethylene oxide (e.g., —O—$CH_2$—$CH_2$— or —$CH_2$—$CH_2$—O—) moieties.

Provided herein are nucleic acid based nanostructures that are useful in the measurement of pN-scale (picoNewton-scale) forces, or sub-pN-scale forces. The DNA nanostructures can be DNA origami structures (DNA origami) or single-stranded tile (SST, e.g., scaffold-free) structures. In one aspect or embodiment, a micromechanical spring sensor is provided. The sensor comprises:

a spring element comprising a DNA origami beam pair comprising one or more single-stranded scaffold nucleic acids or nucleic acid analogs, and nucleic acids or nucleic acid analog staples, comprising:

a flexible first beam and a flexible second beam pinned together by pinning staples at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;

a first tether attached to the first beam at the unpinned section; and a second tether attached to the second beam at the unpinned section;

wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties for at least one pair of corresponding donor and acceptor moieties, such that the sensor produces a detectably different emission spectra when the beams are in the closed position as compared to when the beams are in the open position, for example where the resting gap distance and/or the tensioned gap distance are close to, e.g. within 5 nm, within 4 nm, within 3 nm, within 2 nm, or within 1 nm of a Förster critical distance for the donors and acceptors, and/or where the resting gap distance between the fluorescent donor moieties and the quenching acceptor moieties is less than a Förster critical distance for the donors and acceptors, and the tensioned gap distance between the fluorescent donor moieties and the quenching acceptor moieties is greater than the Förster critical distance for at least one pair of corresponding donor and acceptor moieties, such that the sensor produces a detectably different emission spectra when the beams are in the closed position as compared to when the beams are in the open position; and a drag element attached to a tether of one of the beam pairs.

In another aspect or embodiment, a method of measuring a force is provided. The method comprises: exposing the sensor described above to an environment in which a force is to be measured; illuminating the sensor with electromagnetic radiation within the absorption spectrum of the donor: and; determining, by measuring emission from the sensor in the emission spectrum of the donor or acceptor, either if a force acts on the sensor in the environment sufficient to flex the beams of the sensor into an open position, and/or the extent of flexing of the beams of the sensor to quantify the force acting on the sensor in the environment. By "environment", it is meant any physical location in which a force is to be measured by the sensor, such as in vivo, in vitro, on a surface, or in a fluid or liquid.

"Regular" in the context of a change in emission spectra in relation to tension applied to the spring, refers to a constant or definite pattern, such as a linear, exponential, or logarithmic correlation. This may be achieved, for example and without limitation, by even spacing of the sets of corresponding donor and acceptor moieties in the unpinned section, or patterned spacing within the unpinned section. The correlation of deflection of the members of a FRET pair in the spring structures described herein can be calibrated to a force applied to the structure, such as a shear force, for example and without limitation in a microfluidics chamber.

The spring sensor is an ordered nucleic acid or nucleic acid analog structure, e.g., a nucleic acid and/or nucleic acid analog nanostructure (e.g. DNA nanostructure), produced from nucleic acids (including modified nucleic acids) and/or nucleic acid analogs. Nucleic acid and/or nucleic acid analog nanostructures may be nucleic acid and/or nucleic acid analog origami (e.g., DNA origami) structures or tiled (e.g. single-stranded tiled (SST)) structures.

"DNA origami" and "nucleic acid and/or nucleic acid analog origami" generally refers to the folding of a large, single-stranded nucleic acid (the "scaffold") by annealing with smaller "staple" nucleic acids to form a designated structure. Staples may be fully incorporated within the nucleic acid and/or nucleic acid analog origami structure, or may comprise a pendant portion that does not bind to the scaffold or to a staple and which extends (pends) from the structure. The pendant portions may be labelled with a tag, such as a fluorophore, a fluorescent protein, or a quenching acceptor moiety. The pendent portions may be used as a "tether" to attach other structures or compounds to the structure either by annealing of complementary nucleic acid strands present on the other structure or an intermediate linking compound or structure, or by covalent linkage of a member of a binding pair to the tether. For example, a tether may be biotinylated to bind with avidin/streptavidin. A tether may include an aptamer sequence for specific binding to a target molecule. A tether may be linked to an antibody or a fragment thereof, e.g., a paratope, for specific binding to a target antigen or epitope. A pinning staple is a type of staple used to connect two larger nucleic acid and/or nucleic acid analog origami structures, such as the beams described herein, and may comprise a pendant portion used to anneal with a pendant portion of another structural element, such as another beam or a drag element such as a plate structure, as described herein.

In the context of this disclosure, although the terms "DNA nanostructure" and "DNA origami" refer to structures made from single-stranded deoxyribonucleic acids (DNAs), DNA nanostructures and DNA origami structures may comprise or consist entirely of ribonucleic acid (RNA), DNA, or nucleic acid analog strands unless specified. As such "DNA nanostructures" can include nanostructures comprising single-stranded DNA, single-stranded RNA, single stranded DNA analogs, single-stranded RNA analogs, modified single-stranded DNA or DNA analogs, and/or modified single-stranded RNA or RNA analogs, including combinations of any of the preceding and can be alternatively referred to as "nucleic acid or nucleic acid analog nanostructures". As such "DNA origami" and "DNA origami structures" can include structures comprising single-stranded DNA, single-stranded RNA, single stranded DNA analogs, single-stranded RNA analogs, modified single-stranded DNA or DNA analogs, and/or modified single-stranded RNA or RNA analogs, including combinations of any of the preceding and can be alternatively referred to as "nucleic acid or nucleic acid analog origami" or "nucleic acid or nucleic acid analog origami structures".

Nucleic acids may comprise partially- or completely-modified backbones. Nucleic acid analogs include peptide nucleic acid (PNA), which includes chiral PNAs, such as gamma-PNA (γPNA, see, e.g., US Patent Application Publication No. 2017/0058325 A1, incorporated herein by reference in its entirety for its description of PNA, and particularly γPNA compositions). DNA origami has been used to prepare a large number of micromechanical structures, and choice of nucleic acids and/or nucleic acid analogs to produce a specified structure typically is well within the skill of one of ordinary skill in the art (see, e.g., Beltran S M, et al. Extending the Capabilities of Molecular Force Sensors via DNA Nanotechnology. Crit Rev Biomed Eng. 2020; 48(1):1-16; Ijäs H, et al. Dynamic DNA Origami Devices: from Strand-Displacement Reactions to External-Stimuli Responsive Systems. Int J Mol Sci. 2018; 19(7):2114. Published 2018 Jul. 20; Lee C, et al. Polymorphic design of DNA origami structures through mechanical control of modular components [published correction appears in Nat Commun. 2018 Feb. 7; 9(1):626]. Nat Commun. 2017; 8(1):2067. Published 2017 Dec. 12; Hunter, Philip. "Nucleic acid-based nanotechnology: The ability of DNA and RNA to fold into precise and complex shapes can be exploited for applications both in biology and electronics." EMBO reports vol. 19, 1 (2018): 13-17; and Kearney C J, et al. DNA Origami: Folded DNA-Nanodevices That Can Direct and Interpret Cell Behavior. Adv Mater. 2016; 28(27):5509-5524). DNA origami nanostructures may be modeled using available software, such as cadnano software (see, also, Douglas, Shawn M et al. "Rapid prototyping of 3D DNA-origami shapes with caDNAno." *Nucleic acids research* vol. 37, 15 (2009): 5001-6.doi:10.1093/nar/gkp436). Further, a specified structure is independent of the particular nucleic acid sequences used, but is dictated by the arrangement of complementary sequences. Although the M13 bacteriophage genome often is used as the long strand to be folded into a designated shape by the staples, any suitably long nucleotide may be utilized, provided it contains sufficient unique nucleotide sequences to permit folding into a desired shape.

Nucleic acid and/or nucleic acid analog origami structures are formed by annealing of the scaffold and staples. The individual scaffold and staples are mixed together in a suitable solvent, typically an aqueous solvent, optionally with suitable salts (e.g., $MgCl_2$) and buffers (e.g., Tris-acetate), and any other useful ingredients, such as chelating agents (e.g., ethylenediaminetetraacetic acid, EDTA). First, the mixture is heated, e.g. above the Tm for all ssDNA species, e.g., to 80° C., 85° C., 90° C., or 95° C., to dissociate the scaffold and staples, and then slowly cooling the mixture, e.g., to room temperature. Then the mixture is cooled, typically slowly, to anneal the complex structure. Typical cooling rates are less than 1° C. per minute, and rates may be varied within certain temperature ranges, for example in a range between 60° C. and 24° C., the rate of cooling may be slower than at higher or lower temperatures, such as less than 0.2° C. min$^{-1}$, less than 0.1° C. min$^{-1}$, less than 0.05° C. min$^{-1}$, less than 0.04° C. min$^{-1}$, less than 0.03° C. min$^{-1}$, less than 0.02° C. min$^{-1}$, or less than 0.01° C. min$^{-1}$. The mixture may be cooled in a typical thermal cycler apparatus that can be configured for such slow-cooling.

Tile-based, e.g., single-stranded tile (SST) structures, in contrast to DNA origami, utilize only short sequences of ssDNA that are specifically designed to assemble into complex nanostructures. Unlike DNA origami, tile-based DNA nanostructures do not contain a long scaffold strand. However, like DNA origami, tile-based approaches such as single-stranded tiles (SSTs) and DNA "bricks" can be used to form 2D and 3D structures with either a multilayer or wireframe architecture. As such, the spring sensor can be formed from the hybridization of nucleic acid or nucleic acid analog species as a tile structure comprising binding domains that interconnect the single-stranded nucleic acid or nucleic acid analog molecules into a defined or ordered structure, such as a structure having a periodic structure comprising two or more repeats of a specific structural motif formed from the binding of one or more single-stranded nucleic acid or nucleic acid analog molecules in a particular arrangement, optionally in combination with one or more nucleic acids or nucleic acid analogs in addition to the single-stranded nucleic acid or nucleic acid analog molecules. By SST, it is meant, without limitation, a repeated organization of nucleic acid or nucleic acid analog strands, and should not be construed as limiting to any particular structure or structure design or organization. The arrangement of the single-stranded nucleic acid or nucleic acid analog molecules may be dictated by one or more nucleobase sequences each forming a binding domain on the single-stranded nucleic acid or nucleic acid analog molecule that binds or hybridizes as a member of a binding pair with a complementary nucleobase sequence forming a binding domain on a different single-stranded nucleic acid or nucleic acid analog molecule. Complementary binding domains form a binding pair. Although they may be longer, each single-stranded nucleic acid or nucleic acid analog binding domain may be from 3 to 9, e.g., 3, 4, 5, 6, 7, 8, or 9 bases in length, typically having 100% sequence identity with its complementary binding partner. "Species" in the context of single-stranded nucleic acid or nucleic acid analog used to produce an SST refers to identical nucleic acids and nucleic acid analogs, such as single-stranded nucleic acid or nucleic acid analog molecules having the same sequence and structure. As such, more than one nucleic acid species may be used to produce SST structures.

The binding partners may be on a single single-stranded nucleic acid or nucleic acid analog strand, allowing the same strand to concatenate to form a linear, double-stranded nanostructure. More typically, and to facilitate more complex SST structures, members of binding domain pairs are located on different nucleic acid or nucleic acid analog species that form an SST structure. Each species of nucleic acid or nucleic acid analog, such as single-stranded nucleic acid or nucleic acid analog, used to produce the SST structure may include one, two, three, four, or more binding domains, dependent on the desired SST structure to be formed. For example, two or more different species, such as single-stranded nucleic acid or nucleic acid analog species, may be configured with suitable binding domains to form a nanotube of those species. Ss γPNA species, and more broadly, nucleic acid and nucleic acid analog species, that form the body of a contiguous structure, such as a linear, sheet, or tube structure, may be referred to as contiguous strands. Nucleic acid and nucleic acid analog species, that link two or more contiguous structures, such as a linear, sheet, or tube structure, may be referred to as cross-linking strands or pinning strands. Binding domains may be included in a contiguous strand, with its binding partners included in a crosslinking strand to direct specific arrangement of multiple contiguous structures, such as, for example to form an ordered bundle of tubes The SST may be formed from a combination of single-stranded nucleic acid or nucleic acid analog species and one or more nucleic acid species or nucleic acid analog species, which confer different properties to the SST structure.

The SST structures may be prepared in any suitable solvent. A surfactant, such as an anionic surfactant, may be added to the solvent, which may improve structural uniformity and stability. The SST structures are prepared by mixing the precursors, that is the nucleic acid or nucleic acid analog species in appropriate stoichiometric ratios with the solvent, and complexing the precursors to form the SST structure. Addition of the precursors to the solvent may be enough to form a desired the SST structure. It may be that each precursor is already stored in a suitable solvent prior to mixing and complexing, such as a solvent used to produce the precursor. The precursors may be added in an organized, step-wise manner to first form intermediate structures, and later to form higher-complexity structures. The precursors may be mixed together and maintained at any temperature or series of temperatures useful to make an SST structure therefrom. The precursors may be maintained at a single temperature to form the SST structure. The solvent containing the precursors may be heated to a temperature above which the precursors do not bind, such as a temperature above the Tm of one or more, or all, binding domain pairs in the mixture, followed by cooling the mixture to a temperature at which the precursors bind, such as a temperature below the Tm of one or more, or all, binding domain pairs in the mixture. The temperature may be lowered in a step-wise fashion to allow for partial binding of certain precursors before binding of other precursors. Certain precursors may be added at one time point, and others at a second time point, optionally combined with manipulation of the temperature as described to order the assembly of the SST structure. Additional reagents, such as solvents, surfactants, emulsifiers, lipids, water and salts, etc. may be included in the mixture, or added to the mixture to further manipulate and facilitate a desired SST structure assembly scheme.

Solvents useful in assembly of the SST structures described herein are solvents that permit assembly of the structures by hybridization of the recognition domains of the single-stranded nucleic acid or nucleic acid analog strands. As such, useful solvents may include a solvent that does not interfere with hydrogen-bonding donor/acceptor activity to the extent that it interferes with assembly and/or stability of the SST structure. Such solvents may be a polar aprotic solvent or a polar aprotic organic solvent. Polar aprotic solvents are solvents that lack an acidic hydrogen and therefore are not hydrogen bond donors, examples of which include, without limitation: dimethylsulfoxide (DMSO), dimethylformamide (DMF), hexamethylphosphoramide (HMPA, which not organic), dichloromethane, N-methylpyrrolidone, tetrahydrofuran, acetonitrile, propylene carbonate, pyridine, and ethyl acetate, including combinations of two or more of any of the preceding. Other useful solvents may include: dimethylacetamide, valerolactone, 2,5-dimethyltetrahydrofuran.

Fluorescent or fluorescence refers to the ability of a fluorophore to absorb electromagnetic radiation, for example ultraviolet radiation or light, to reach an excited state, and release a photon upon relaxation to a lower energy state, (e.g., a ground state). The excited state may be metastable, resulting in phosphorescence. Transfer of the energy of the fluorophore to another molecule is referred to as quenching, examples of which include Förster Resonance Energy Transfer (FRET), along with other mechanisms.

A FRET pair is a pair of chromophores, e.g., fluorophores, that, when placed within a sufficiently small radius from each-other, undergo resonance energy transfer from a first member of the FRET pair (donor) to the second member of the FRET pair (acceptor or quenching acceptor). The process of resonance energy transfer takes place when a donor fluorophore in an electronically excited state transfers its excitation energy to a nearby chromophore, the acceptor, such that the acceptor quenches the donor. The emission spectrum for the donor may overlap with the excitation spectrum for the acceptor. When the donor and acceptor in a FRET pair are sufficiently close together, excitation of the donor results in the transfer of the excitation energy to the acceptor (quenching of the donor by the acceptor), resulting in fluorescence at the emission wavelength of the acceptor. As the distance between the donor and acceptor in a FRET pair increases, excitation of the donor results in increasingly lesser transfer of the excitation energy to the acceptor, resulting in lower fluorescence, or no fluorescence at the emission wavelength of the acceptor, and typically increased emission at the emission wavelength of the donor.

Primary criteria for FRET to occur can be as follows: donor and acceptor molecules are in close proximity (typically 10-100 Å); the absorption spectrum of the acceptor overlaps the fluorescence emission spectrum of the donor; and donor and acceptor transition dipole orientations are approximately parallel.

The Förster critical distance (R(0)) is the acceptor-donor separation distance for which the transfer rate equals the rate of donor decay (de-excitation) in the absence of acceptor. In other words, when the donor and acceptor radius (r) equals the Förster critical distance, then the transfer efficiency is 50 percent. At this separation radius, half of the donor excitation energy is transferred to the acceptor via resonance energy transfer, while the other half is dissipated through a combination of all the other available processes, including fluorescence emission of the donor. The Förster critical distance value typically falls within a range of 2 to 6 nanometers. Roy et al. (Roy et al. "A practical guide to single-molecule FRET." *Nature methods* vol. 5(6) (2008): 507-16. doi:10.1038/nmeth.1208) among many other resources describe the FRET process and options for FRET pairs.

A large variety of small molecule fluorophores (e.g., 2000 Da or less, or 1000 Da or less, such as cyanine, xanthine, squaraine, among many other dyes, see, e.g., FPbase (fpbase.org) and fluorophores.tugraz.at) or protein fluorophores (typically 10 kDa or larger) are known and are shown to be effective in FRET pairs, and can be arranged on the beams of the spring sensor described herein to produce FRET activity when the beam is in its closed configuration, and to produced progressively less FRET activity on application of tensional force and flexing the beams of the sensor to an open configuration. Selection of FRET pairs may be made by determining the presence of overlap in the emission spectra of the donor and excitation spectrum of the acceptor (see, e.g., Roy et al., providing non-limiting examples of certain small molecule FRET donors, such as Cy3, ATTO550, and Alexa555, and certain small molecule FRET acceptors, such as Cy5, ATTO647N, and Alexa647, and describing methods of conjugating the dyes or biotin to nucleic acids (see, Table 2 of Roy et al.).

Example of protein FRET pairs include, without limitation: ECFP-EYFP; mTurquoise2-sEYFP; mTurquoise2-mVenus; EGFP-mCherry; Clover-m Ruby2; mClover3-mRuby3; mNeonGreen-mRuby3; eqFP650-iRFP; mAmetrine-tdTomato; LSSmOrange-mKate2; EGFP-sREACh; EGFP-ShadowG; EGFP-activated PA-GFP; EGFP-Phanta; mTagBFP-sfGFP; mVenus-mKOK; and CyOFP1-mCardinal (See, e.g., Bajar B T, et al. A Guide to Fluorescent Protein FRET Pairs. Sensors (Basel). 2016; 16(9):1488).

The quenching acceptor can be a fluorescent quencher that fluoresces at its emission spectrum upon excitation by the donor. The quenching acceptor can be a dark quencher, which is non-fluorescent, but may dissipate energy received from the donor by non-fluorescent means, such as by heat dissipation (e.g., by molecular vibration). That is, the excited quencher acceptor may return to the ground state through fluorescent emission or nonradiatively (dark quenching). Non-limiting examples of dark quenchers include: Dabsyl (dimethylaminoazobenzenesulfonic acid), BLACK HOLE QUENCHER® Dyes, QXL™ quenchers, IOWA BLACK® FQ, IOWA BLACK® RQ, and IRDye® QC-1, among others.

Ligands may be attached to any sensor described herein to facilitate attachment of the sensor to a target cell, tissue, or other structure, or to assist in assembly of the sensor structure. A ligand can be attached to the described DNA origami spring/sensor structure by any suitable method, either directly by covalent linkage or indirectly using suitable ligands, such as the biotin/streptavidin conjugation, and may be attached, directly or indirectly to a pendant portion or tether of a staple used to prepare the DNA origami spring/sensor structure. The sequence of a nucleic acid-based ligand, such as an aptamer, may be incorporated directly within the pendant portion or tether of a staple used to prepare the DNA origami structure.

The term "ligand" refers to a binding moiety for a specific target, referred to as its binding partner. The molecule can be a cognate receptor, a protein a small molecule, a hapten, or any other relevant molecule. The term "antibody" refers to an immunoglobulin, derivatives thereof which maintain specific binding ability, and proteins having a binding domain which is homologous or largely homologous to an immunoglobulin binding domain. As such, the antibody operates as a ligand for its cognate antigen, which can be virtually any molecule. Natural antibodies comprise two heavy chains and two light chains and are bi-valent. The interaction between the variable regions of heavy and light chain forms a binding site capable of specifically binding an antigen (e.g., a paratope). The term "$V_H$" refers to a heavy chain variable region of an antibody. The term "$V_L$" refers to a light chain variable region of an antibody. Antibodies may be derived from natural sources, or partly or wholly synthetically produced. Many antibodies and fragments thereof are available from commercial sources. An antibody may be monoclonal or polyclonal. The antibody may be a member of any immunoglobulin class, including any of the human classes: IgG, IgM, IgA, IgD, and IgE.

"Lectins" are a group of proteins from non-immune origins that bind carbohydrates and agglutinate animal cells. They exhibit extremely high binding affinities for specific sugars, and can be used to target specific cell types expressing their binding partner, including carbohydrates, polysaccharides, glycoproteins, and glycolipids. They serve a variety of functions in their natural setting, but can be a powerful tool when used to target their binding partner. Lectins can agglutinate cells and/or precipitate complex carbohydrates and, as such, have served as a powerful tool for biomedical research and clinical utility, including, carbohydrate studies, fractionation of cells and other particles, lymphocyte sub-population studies, mitogenic stimulation, blood group typing, and histochemical studies. They are isolated from a wide variety of natural sources, both plant and animal. Concanavalin A (Con A) is a broadly-studied lectin that binds α-D-mannosyl and α-D-glucosyl residues. Peanut agglutinin targets Galβ1-3GalNAcα1-Ser/Thr and, e.g., inhibits T-cell activity and can be used to distinguish lymphocyte subsets. Many other lectins are broadly-known and characterized, and can be obtained from commercial sources.

Ligands, also referred to as binding reagents, having limited cross-reactivity are generally preferred. In certain embodiments, suitable ligands include, for example, polypeptides, such as for example, lectins or antibodies, monoclonal antibodies, or fragments, derivatives, or analogs thereof, including without limitation: Fv fragments, single chain Fv (scFv) fragments, $Fab_1$ fragments, $F(ab')_2$ fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems (($ScFv)_2$ fragments), diabodies, triabodies, tetrabodies, which typically are covalently linked or otherwise stabilized (e.g., leucine zipper or helix stabilized) scFv fragments, di-scFv (dimeric single-chain variable fragment), single-domain antibody (sdAb), or antibody binding domain fragments and other binding reagents including, for example, bi-specific T-cell engagers (BiTEs), aptamers, template imprinted materials, and organic or inorganic binding elements. In exemplary embodiments, a ligand specifically interacts with a single motif or epitope. In other embodiments, a ligand may interact with several structurally-related motifs or epitopes.

The term "antibody fragment" refers to any derivative of an antibody which is less than full-length. In exemplary embodiments, the antibody fragment retains at least a significant portion of the full-length antibody's specific binding ability. Examples of binding reagents, including antibody fragments, but are not limited to, Fab, Fab', $F(ab')_2$, Fv, Fd, dsFv, scFv, diabody, triabody, tetrabody, di-scFv (dimeric single-chain variable fragment), bi-specific T-cell engager (BiTE), single-domain antibody (sdAb), or antibody binding domain fragments. The antibody fragment may be produced by any means. For instance, the antibody fragment may be enzymatically or chemically produced by fragmentation of an intact antibody, or it may be recombinantly or synthetically produced. The antibody fragment may optionally be a single chain antibody fragment. Alternatively, the fragment may comprise multiple chains which are linked together, for instance, by disulfide linkages. The fragment may also optionally be a multi-molecular complex. A functional antibody fragment may consist of at least about 50 amino acids or at least about 200 amino acids. Antibody fragments also include miniaturized antibodies or other engineered binding reagents that exploit the modular nature of antibody structure, comprising, often as a single chain, one or more antigen-binding or epitope-binding (e.g., paratope) sequences and, at a minimum, any other amino acid sequences needed to ensure appropriate specificity, delivery, and stability of the composition (see, e.g., Nelson, A L, "Antibody Fragments Hope and Hype" (2010) MAbs 2(1): 77-83).

Example 1—Shear Sensor Design

Figure 2:
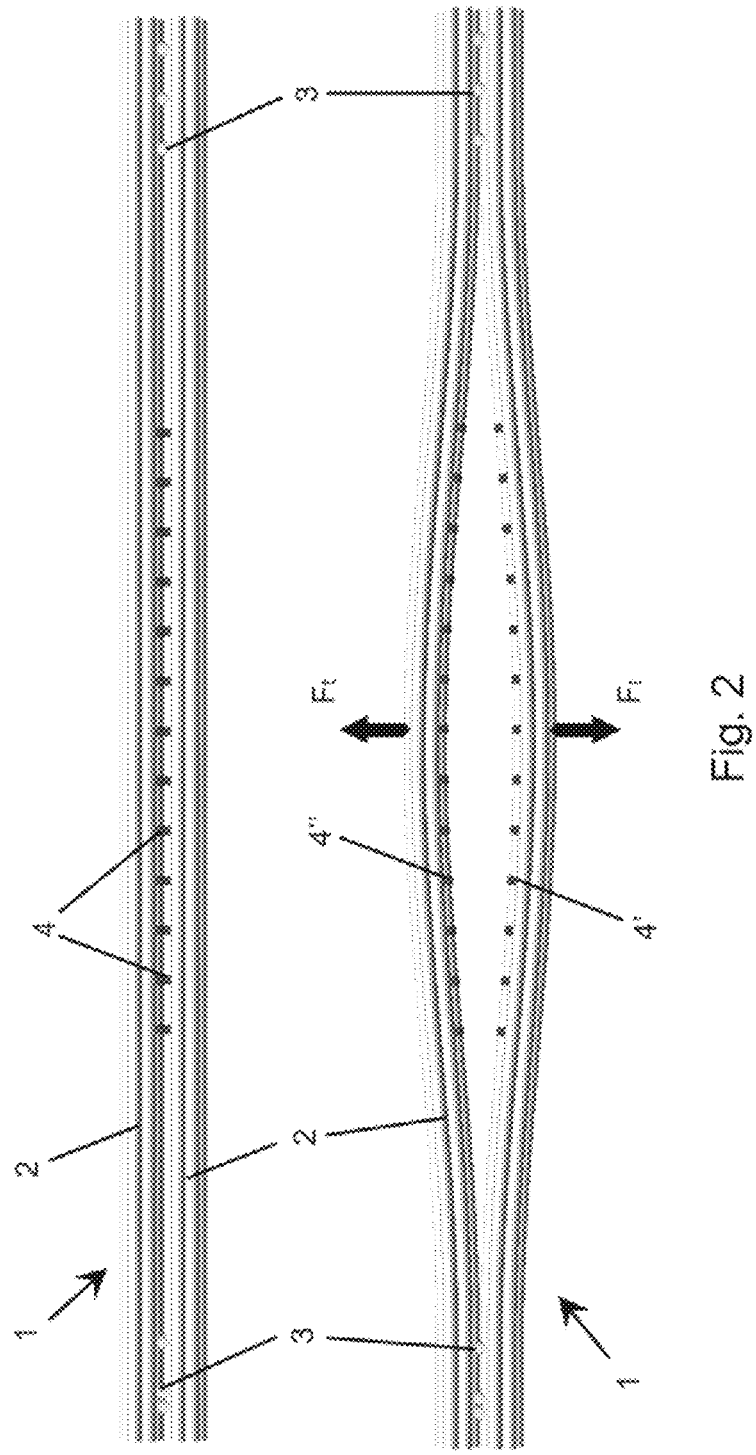
FIG. 2 depicts schematically closed (top) and open (bottom) state of a DNA origami based shear sensor spring element.

We designed a double beam shear sensor out of DNA origami. FIG. 2 shows the close and open state of such a shear sensor spring element 1. As depicted, the spring element 1 includes of two beams 2 of bundles of 6 dsDNA helices, held together by 6 pairs of pinning staples 3 which can be two staples, one originating from a first beam, and the other originating from the other beam, comprising complementary pendant portions that hold the beams 2 together by annealing. Beams may comprise bundles of any number of DNA helixes, such as 1, 2, 3, 4, 5, 6, 7, 8, 9, or 10 substantially parallel DNA helices. Corresponding FRET fluorophore FRET pairs 4 are depicted (top), which each include donor 4' and acceptor 4" fluorophore moieties (omitted for clarity on FIG. 1, top), showing spatial alignment of the fluorophore FRET pairs 4 on the beams 2. The open state of the spring element 1 is shown in FIG. 2, bottom, in which a tensional force $F_t$ is applied to the beams, e.g. via tethers attached at the arrows, thereby separating the FRET donor fluorescent moieties 4' (e.g. a Cy3 fluorophore moiety) from the FRET acceptor fluorescent moieties 4" (e.g. a Cy5 fluorophore moiety). The stronger the tensional force $F_t$ applied to the beams, the larger the distance between corresponding donor 4' and acceptor 4" moieties of each FRET pair, and the lesser the FRET effect. By tuning the position of the pinning staples 3, we can tune the effective length of the beam that is able to deform.

Figure 3:
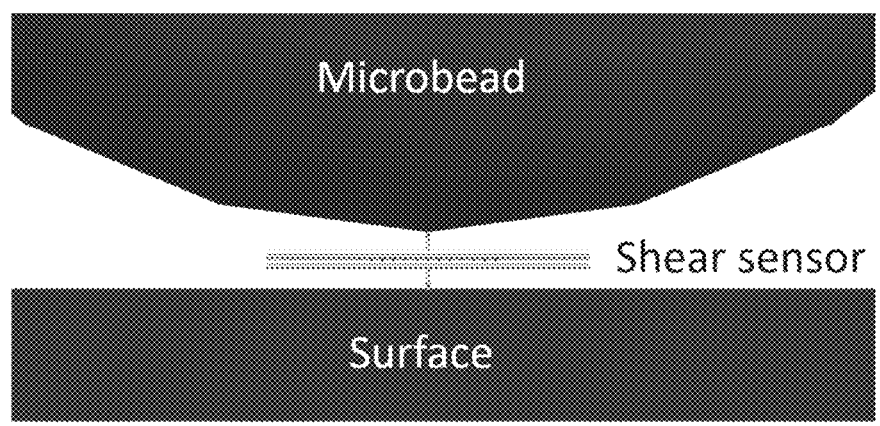
FIG. 3 depicts schematically an example of a structure for use in measuring shear force at a surface of a substrate.

We assemble the setup shown in FIG. 3 to measure the shear force at a surface. The DNA shear sensor is sandwiched in between of the surface and a microbead used as a drag element. Shear force exerted on the microbead will translate to a pulling force (tensional force $F_t$) to the shear sensor and cause the deformation shown in FIG. 2 (bottom).

Example 2—Calculation of the Deformation

Figure 4:
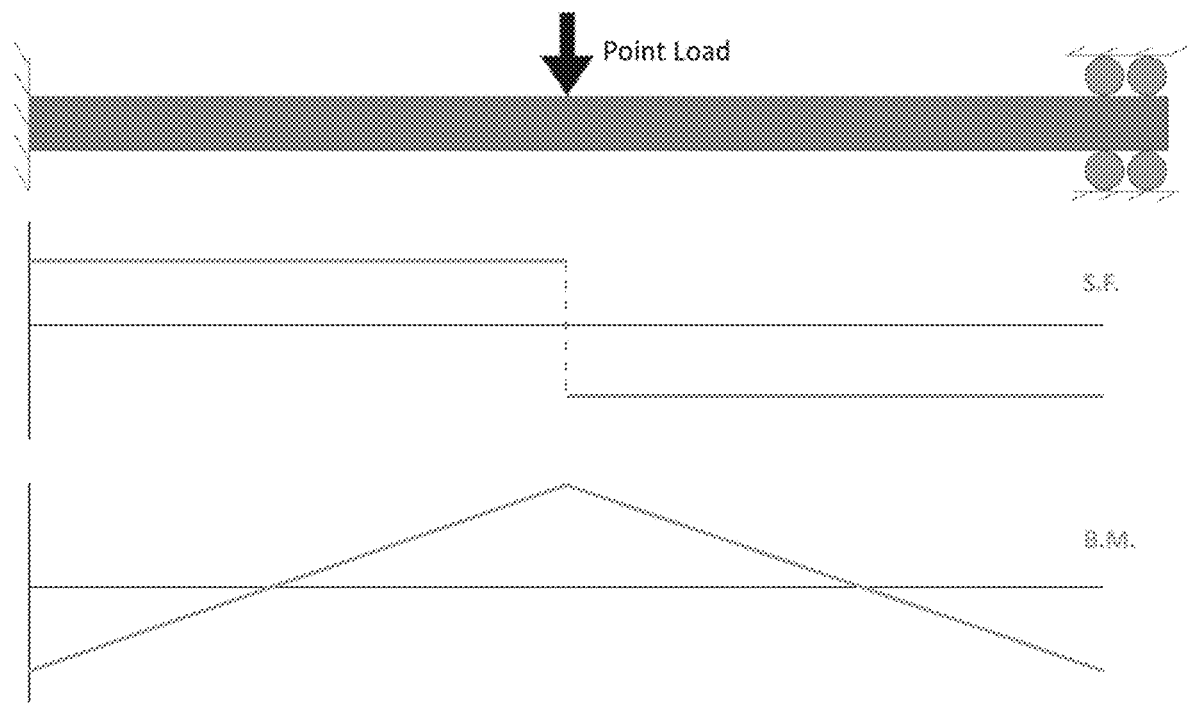
FIG. 4 is a diagram depicting loading condition (top), shear force (middle) and the bending moment diagram (bottom) of one beam of the shear sensor. Because of the symmetry of two beams, we assume the constrain condition is fixed at one end, fixed at transverse direction but able to slide longitudinally.

We plot out the shear force (S.F.) and the bending moment diagram (B.M) to one beam of the double tube structure in FIG. 4. And we calculate the deformation of the shear sensor using beaming bending theory.

Considering we have two beams that are symmetrical. The distance between the two beams at the central point would be as shown in Equation 1.

$$\delta = 2FL^3/(192EI) \tag{1}$$

where F is the external point load, in our case, shear force we want to measure. L is the effective length of the shear sensor. E is the Young's modulus of DNA nanotube. We assume the crossovers don't change the Young's modulus of dsDNA, which is around 1 GPa. I is the second momentum of inertia of the single beam. As calculated from the cross-section, it is 157 $nm^4$. This equation implies that for a given external shear force, we can control the range of deformation by changing the effective length of the beam. We use Förster resonance energy transfer (FRET) between Cy3 and Cy5 to monitor the deformation of the shear sensor. FRET is mostly sensitive to measure deformation when the distance is about 6 nm. Thus, by tuning the position of the pinning staples, we can define the measuring range of the shear force.

Example 3—Synthesis of Exemplary Shear Sensor

An exemplary shear sensor was prepared using a ssDNA M13 scaffold and ssDNA staples. Double tube DNA origamis were prepared by folding a 7249 base long single-stranded DNA scaffold from virus M13mp18 (Bayou Biolabs) with a set of short single-stranded sequences (See FIGS. 5A-5G). The mixture is in 1×TAE with 12.5 mM $MgCl_2$. The concentration of each DNA sequence are:

M13mp18 scaffold: 10 nM
Unmodified short sequence (Table A): 100 nM
Staple sequences modified with different species of overhangs (Table B): 100 nM
Cy5-Stalk1 comp, Cy3-Stalk3 comp (Table C): 5 uM
Bio-Stalk5 comp (Table 3): 400 nM.

Origamis were annealed by a two-day thermal ramp using Bio-Rad c1000 Touch Thermal Cycler. The Thermal ramp is:

80° C.: hold for 5 minutes.
80° C.-65° C.: decrease 0.1° C. every 24 seconds.
65° C.-24° C.: decrease 0.1° C. every 6 minutes and 18 seconds.
24° C.-4° C.: decrease 0.1° C. every 18 seconds.

After folding the origamis were stored at 4° C. The origami can be stored in the refrigerator for a week before usage.

Example 4—Assembly of the Shear Sensor to a Flow Channel

Figure 6A:
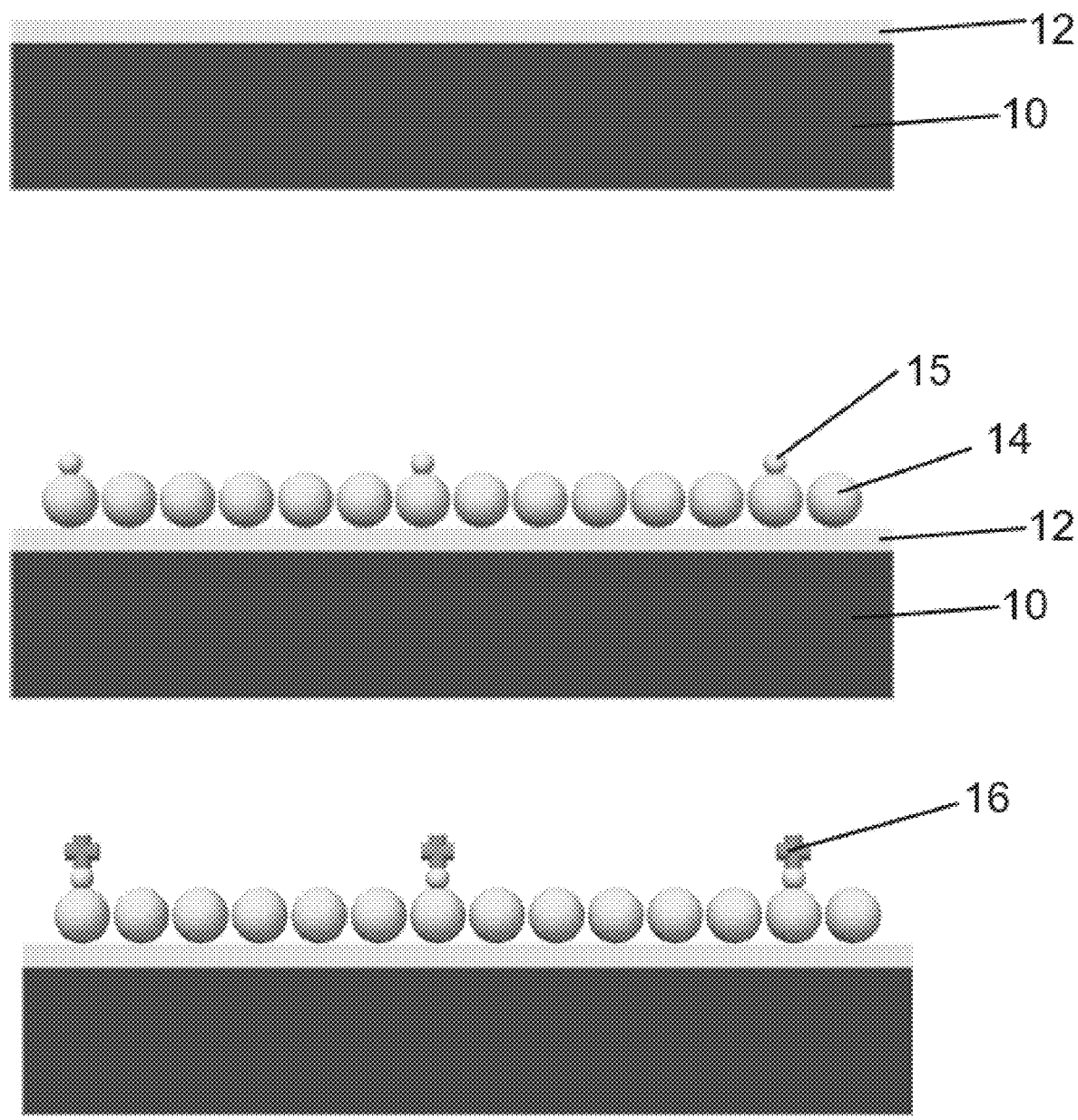
Figure 6B:
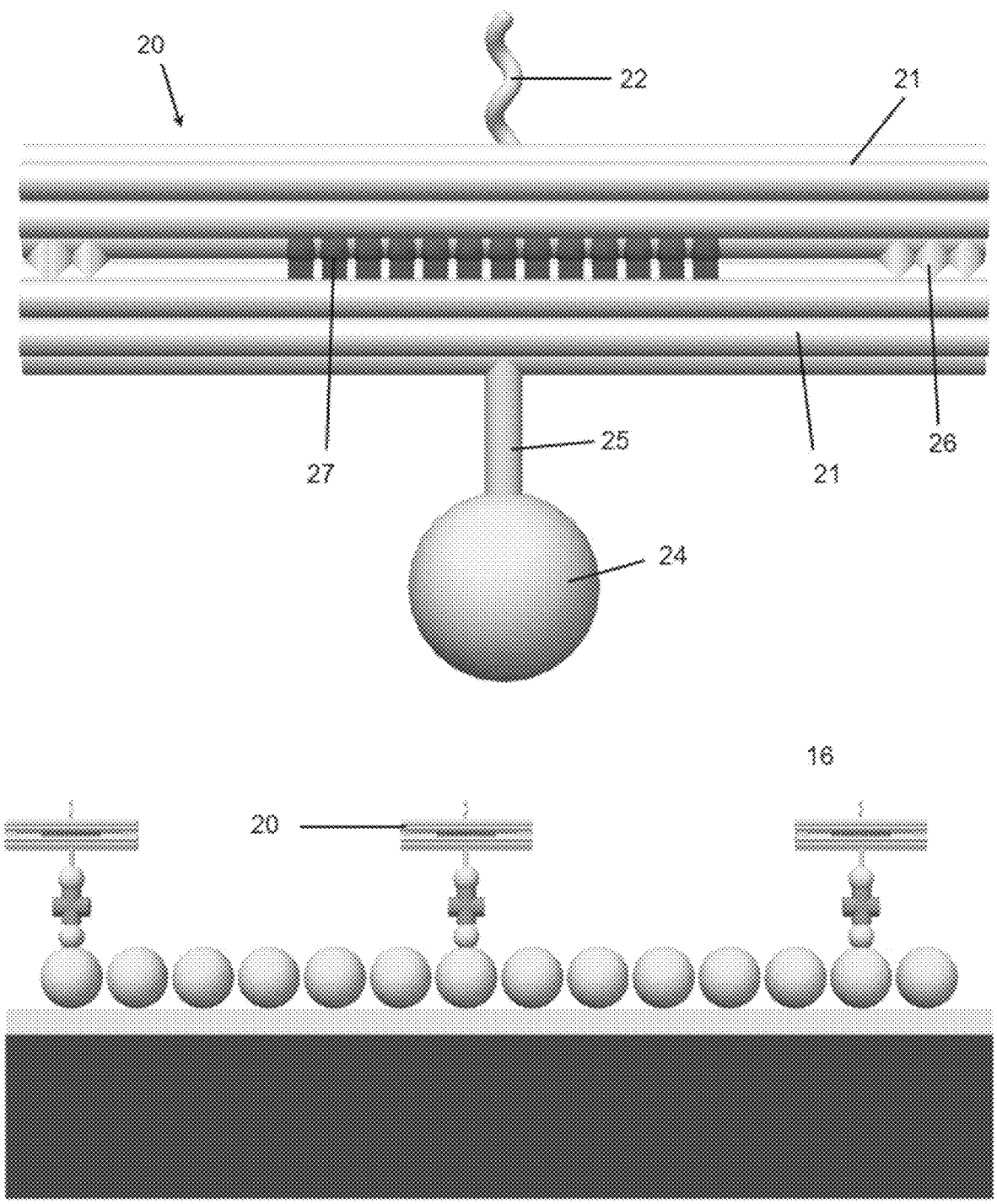
Figure 6D:
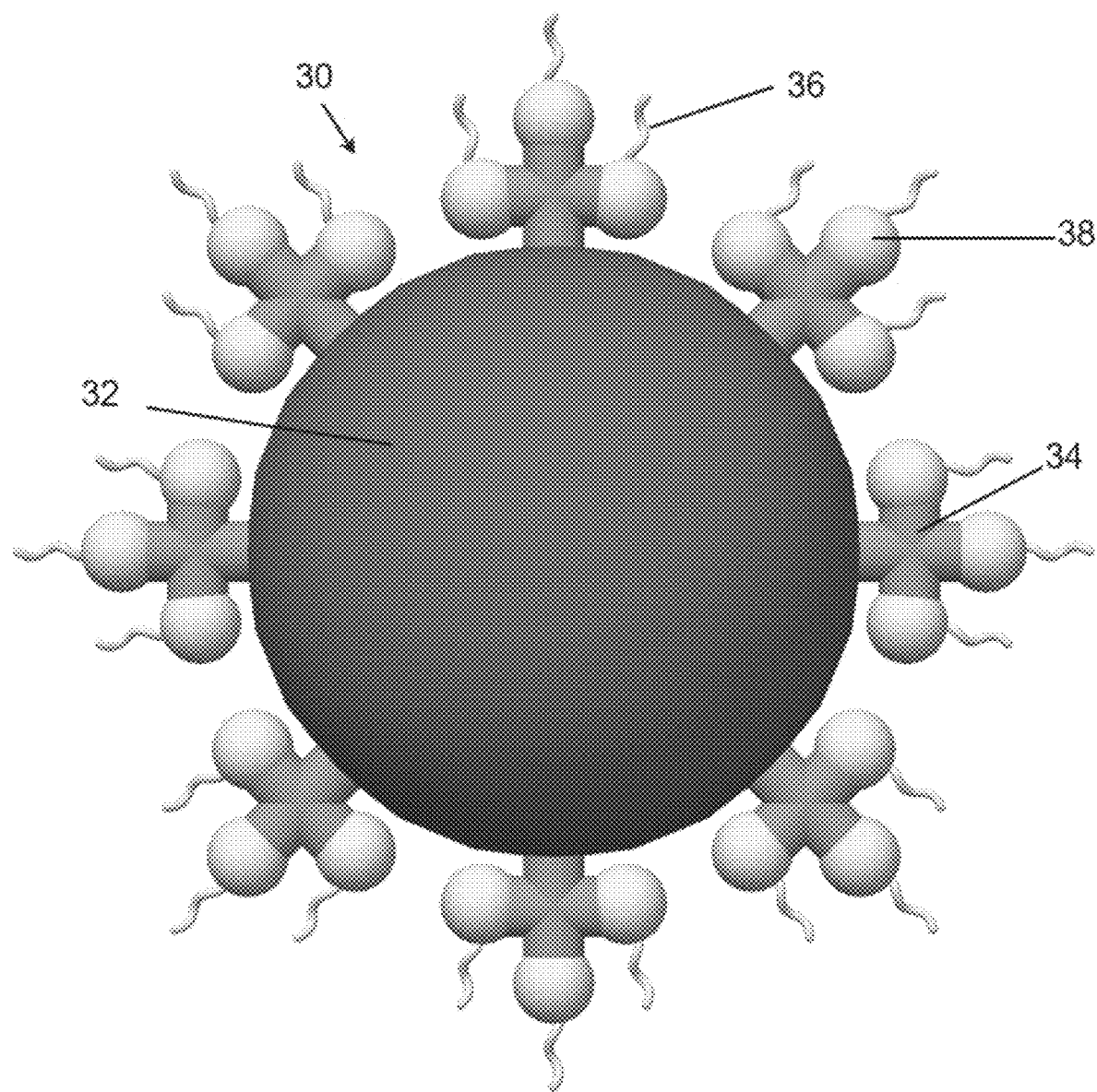
Figure 6E:
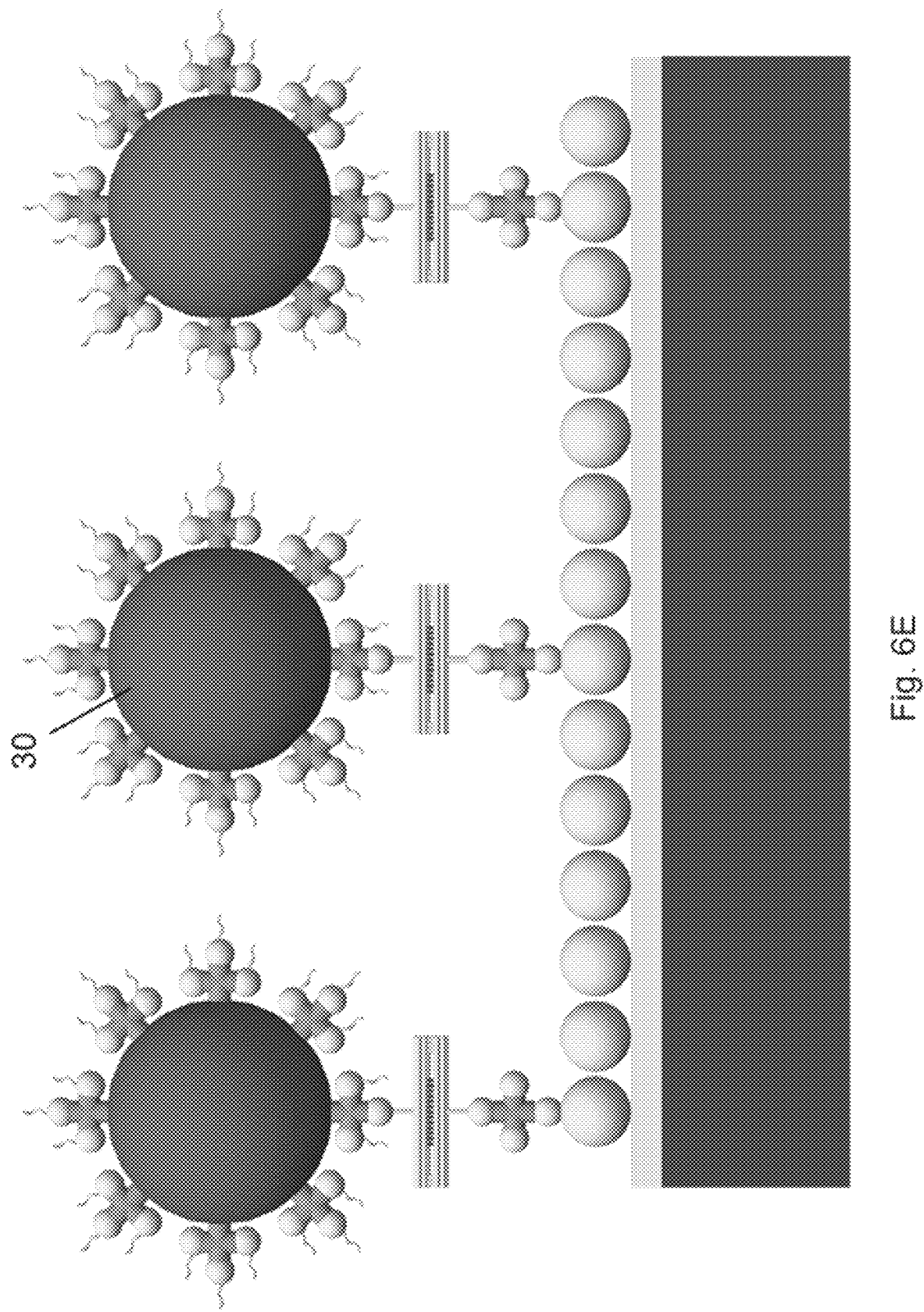

Materials:
Channel: Nitrocellulose-coated microfluid channel
Buffer: 1×TAE with 12.5 mM $MgCl_2$
BSA-bio: 0.1% BSA-biotin (Sigma*8549-10 mg) with 12.5 mM $MgCl_2$ in 1×TAE
BSA: 0.1% BSA (Sigma 05470-1G) with 12.5 mM $MgCl_2$ in 1×TAE
SA: 0.05% streptavidin, 0.05% BSA and 12.5 mM $MgCl_2$ in 1×TAE
Origami: DNA nanostructure from the annealing, e.g., as described in Example 3.
Bead: Dynabeads™ MyOne™ Streptavidin T1 microbead
Bio-DNA: Bio-Stalk4 comp DNA strand in water The step by step protocol is listed below is shown in FIGS. 6A-6C. FIG. 6A depicts the orientation of glass substrate 10 and nitrocellulose coating 12, followed by coating with BSA 14 and biotin 15. FIG. 6B depicts the conjugation of the DNA origami sensor 20 to the structure via streptavidin 16. The sensor 20 includes beams 21, a first ssDNA tether 22, biotin 24 attached to a second tether 25, pinning staples 26 holding the beams 21 together, and FRET pair fluorochrome moieties 27: In FIG. 6C, additional biotin 28 is added to the structure to saturate biotin-binding sites of the streptavidin 16. The structure is then conjugated with biotinylated beads 30, including a bead substrate 32 conjugated with streptavidin 34, and bound to biotinylated ssDNA 36, comprising biotin moieties 38. The biotinylated ssDNA 36 anneals to the first ssDNA tether 22. The procedure for formation of the structure is as follows.

1. Mix the beads with bio-DNA so that there are 500,000,000 beads per ml in 1× TAE with 12.5 mM $MgCl_2$ and the concentration of bio-DNA is 6.67 uM.

2. Incubate the mixture at room temperature (~25° C.) for 30 minutes.
3. Flow 15 uL BSA-biotin through the channel to cover the nitrocellulose coated glass. Incubate in humid chamber for 4 min to allow the conjugation happens.
4. Flow 15 uL BSA through the channel to wash off excess BSA-bio. Incubate in humid chamber for 4 min to allow the conjugation happens.
5. Flow 15 uL SA through the channel to bind with biotin. Incubate in humid chamber for 4 min to allow the conjugation happens.
6. Flow 15 uL BSA through the channel to wash off excess SA. Incubate in humid chamber for 4 min to allow the conjugation happens.
7. Flow 15 uL 0.5 nM origami through the channel to bind with exposed streptavidin. Incubate in humid chamber for 4 min to allow the conjugation happens.
8. Flow 15 uL BSA through the channel to wash off excess origami.
9. Flow 30 uL BSA-bio through the channel to cover all exposed streptavidin. Incubate in humid chamber for 4 min to allow the conjugation happens.
10. Flow 100 uL buffer through the channel to wash off everything floating in the solution.
11. Flow 30 uL bead-DNA from step 1 and step 2 through the channel to link the bead to origami. Incubate in humid chamber for 10 min to allow the conjugation happens.
12. Flow 200 uL buffer through the channel to wash off excess bead.
13. Flow 15 ul TROLOX (6-hydroxy-2,5,7,8-tetramethylchroman-2-carboxylic acid) to protect dye molecules from photobleaching too fast.

Example 5—Design of Sensor for Identifying Cardiac Wall Shear Stress (WSS) Signatures An approach is provided for identifying wall shear stress (WSS) signatures that can predict both healthy and pathophysiological development of cardiac valves by creating a map of cardiac WSS throughout embryonic development. A nanoscale shear sensors can be introduced into an embryonic vasculature system to map WSS throughout early development of an animal or human. The exemplary approach combines multiple advanced techniques in an integrated experimental design that utilizes mechanical design, DNA nanotechnology, coarse grained molecular dynamics simulation, microfluidics, endothelial cell culture, and high-speed light sheet microscopy studies of a human or animal vascular system. The nanoscale shear sensors can be calibrated using computationally-designed microfluidic shear chambers.

Fluorescent mechanosensors may be made of structural DNA nanotechnology so that external light activation can power the sensors, which can provide fluorescent output signals. In some embodiments, described herein includes using the mechanosensors as (1) surface-bound nanosensors for facilitating hydrodynamic characterization of naval vessels by providing a quantitative visualization of the patterns of experience WSS, and (2) sensor-decorated mm-scale beads as a bioinspired shear-sensing tool for monitoring flow disruptions.

Figure 7:
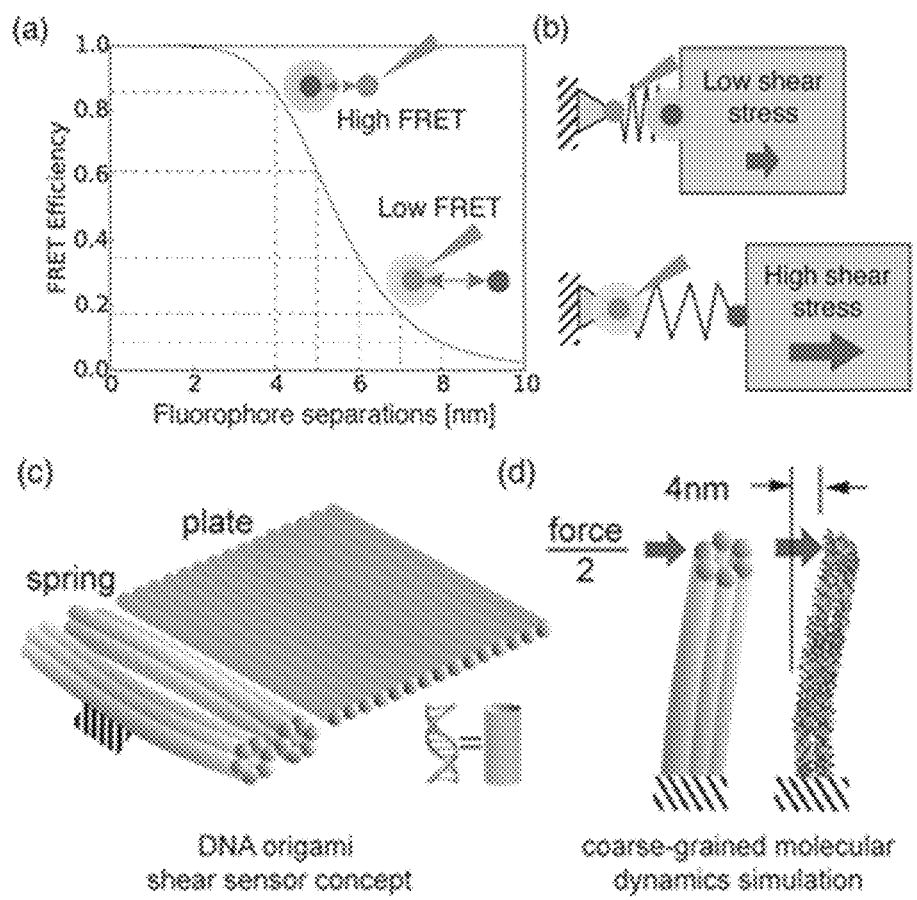
FIG. 7. Mechanical design and transduction mechanism for nanoscale shear sensors. (a) Förster Resonance Energy Transfer (FRET) is nonradiative energy transfer between fluorophores whose emission and excitation spectra overlap. (b) This energy transfer occurs in a displacement-dependent manner than can be used to quantitatively calculate fluorophore displacement. (c) For spring-plate sensors, shear or drag forces acting on the sensor will cause the nanosprings to stretch, and FRET will be used to measure applied forces. (d) Sensor stiffness can be estimated using solid mechanics approaches and more precisely using coarse-grained molecular dynamics simulations.

Shear sensors can comprise of a spring element and a microbead drag element, and parallel plate shear chambers can be used to characterize sensor function as shown in FIG. 7. FIG. 7 (c) depicts an alternate version of the sensor structure described in Example 4, in which the drag element is a DNA origami plate as opposed to a bead or particle.

Sub-micron scale sensors can be designed and produced by utilizing molecular tension sensor (MTS) approaches and molecular "ruler" technology. MTSs can be genetically encoded and synthesized in solid phase or self-assembled using DNA nanotechnology. MTSs can be calibrated using single molecule techniques, and the force resolution of these sensors can be tuned with a typical minimum force resolution of about approximately 1 pN (the approximate force generated by a single myosin motor).

Quantitative, analog sensors can be created from DNA origami with internally and externally tunable sensitivity and Förster Resonance Energy Transfer (FRET) as a molecular "ruler". For FRET pairs like Cy3 and Cy5 (for example and without limitation), if the donor (Cy3) is excited, non-radiative energy transfer occurs in a separation-dependent manner to the acceptor (Cy5). As a result, activation of the donor can lead to fluorescence of the acceptor in the high FRET condition (see FIG. 6 (a)). To move from a high FRET to low FRET state, Cy3 and Cy5 need only be separated by approximately 3.5 to 7.5 nm. Therefore, sensors whose unloaded condition maintains FRET pairs in their close high FRET state can be designed. Using coarse-grained molecular dynamics simulation with oxDNA, the force required to stretch the springs 4 nm can be calculated and this analysis can allow internal tuning of the spring sensitivity. Specifically, the stiffness of the springs such that they deform about approximately 4 nm (the distance required to move to from the resting high FRET state to the low FRET state) under maximum load (e.g., maximum tensional force or $F_t$ as depicted in FIG. 2) can be tuned. Internal tuning of spring stiffness can be done by varying the spring cross-section, length (distance between pinning locations) and edge conditions to adjust the sensitivity of the device to fluid-induced forces.

caDNAno software can be used to design a spring and, optionally, any suitable drag element, such as a plate structure, using DNA origami with, for example and without limitation, the M13mp18 (FIGS. 8A-8B, SEQ ID NO: 233) scaffold. For plate (planar) structures, to minimize structural twist and ensure flatness, a honeycomb lattice or crossover-corrected square lattice for sensor subcomponents can be utilized. In the sensor spring, Cy3 can be incorporated on strands of one beam and Cy5 onto strands of the other. The placement of the fluorophores (e.g., special location of corresponding fluorophores of each FRET pair) (radially and axially) can further enhance sensor output signal for a given loading condition.

A one-pot DNA origami anneal process may be used in which the M13 scaffold DNA can be combined with a 10-fold excess of staple stands in the presence of TAE$^+$Mg$^{2+}$ (Tris, Acetate, EDTA, and Mg$^{2+}$) buffer and a slow ramp to anneal from about approximately 90° C. to room temperature using a C1000 Thermal Cycler. After purification, using 100 kDa molecular weight cutoff filters to remove free staples, and gel electrophoresis to confirm structure formation without undesired aggregation, the shape distribution can be characterized using both atomic force microscopy (AFM) and transmission electron microscopy (TEM), and then iteratively tune the cross section, length and edge connections to adjust the sensor stiffness.

The deformation from oxDNA models can match closely to that predicted by a fixed-fixed beam model with a single point load in the middle, which predicts a maximum deformation, $d_{max}=PL^3/(192EI)$, where P is the load, L is the effective beam length or unstapled beam length, E is the Young's Modulus of dsDNA or about approximately 300 MPa, and I is the second moment of area. If maximum deformation is less than about approximately 4 nm, fluorophores can be located near the middle of the beams. Otherwise, placing fluorophores near the edges of the beams will allow reduced signal even when maximum deformation exceeds about approximately 4 nm. Nonetheless, the staple strands that connect the beams and pinch together the two ends may allow more compliance than expected, causing a hinge-like boundary condition with spring deformation resembling more of a pinned-pinned beam. In this case the effective stiffness can be one quarter of the fixed-fixed stiffness with deformations four times larger than predicted. Further, unforeseen kinking of the dsDNA may cause further divergence from models. Regardless, overall stiffness ($P/d_{max}$) can still be approximately proportional to the length cubed and inversely proportional to the second moment of area, which can determined by the beam cross section. Finally, since the magnitude of the hydrodynamic forces experienced by the sensors can be proportional to sensor plate area, if needed, sensor plates that are about approximately 4-10× larger than originally proposed can be created, increasing force sensitivity while maintaining spring stiffness.

Figure 9:
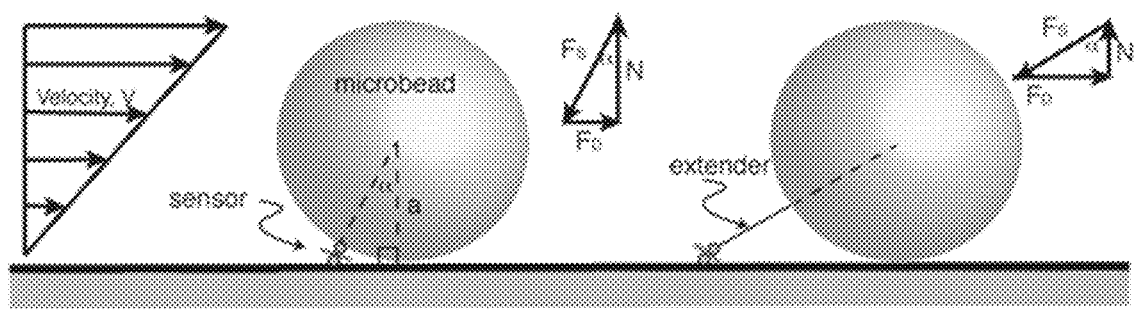
FIG. 9. (left) If drag caused by higher velocity at top of bead is neglected, tethered spring plus microbead sensor systems will experience Stokes drag, $F_D$, a normal reaction force, N, and the sum of those forces will be equal and opposite to the force on the spring. (right) The addition of an extender will increase angle α, allowing $F_S \sim = F_D$.

Before an all-DNA nanosensor can be built, the fluorescence signal resulting as a function of applied load can first be characterized. Given the expense and complexity of prototyping numerous plate geometries, assembling nanosensors comprised of nanospring elements connected with microbeads can first be achieved. As larger particles, microbeads will experience Stokes drag, $F_d=6\pi a\eta V$, where η is the fluid viscosity, a is the microbead radius, and V is the fluid velocity. Using a parallel plate shear chamber, known flow profiles with calibrated levels of wall shear stress can be generated. Near the wall, the parabolic flow profile of fully developed flow can be approximated as a linear ramp, with the average fluid velocity occurring at a height equal to the bead radius. By ignoring the torque applied by higher drag at the top of the bead, this system can be modelled with a simple force balance as shown in FIG. 9. To create a surface decoration strategy, whose sensitivity can be externally tuned by means of an attached drag-inducing microbead, decoration approaches for assembling microbead-on-spring constructs can be performed. Flow testing in microfluidic shear chambers can be used to characterize spring stiffness as well as sensor rupture forces. For this work, a molecular biology toolkit to utilize the hybridization of DNA alongside the use of molecular adhesives like biotin and streptavidin can be accomplished to assemble these devices. As shown in FIGS. 6A-6E, Nitrocellulose can be used to coat cover slips. Therefore, biotinylated bovine serum albumin (biotin-BSA) can be introduced at a low concentration to ensure sparse decoration with spacing between biotins on the order of about approximately 10 microns. Backfilling with BSA can passivate the remainder of the surface and prevent nonspecific binding. Tetravalent streptavidin can be introduced, followed by biotinylated DNA origami spring constructs. A low concentration of springs to prevent multiple springs from binding a single streptavidin can be introduced. Further, the relatively large size of the spring (200 nm) compared to the size of streptavidin (4-5 nm) can further reduce the likelihood of multiple springs binding a single streptavidin. Thereafter, DNA-labeled microbeads can be introduced, and given the sparse decorations, it is likely that only one microbead can adhere to any one surface-bound spring. For constructs with "extenders," 400-nm-long DNA origami nanotubes will be introduced between the spring and microbead using DNA hybridization for specific attachment.

Given that biotin and streptavidin form the strongest non-covalent bond capable of withstanding about approximately 3.6-5.4 pN of force before rupture, failure can come from the unzipping of DNA-based attachments. In this case, longer hybridization domains (16 to 25 bases in length) can be designed. Additionally, multivalent attachment sites can be designed, comprised of multiple attachment stalks.

If rupture occurs at the biotin-streptavidin interface, alternate cover slip functionalization approaches (like thiol-gold) and alternate adhesion molecules (like digoxigenin and antidigoxigenin) can be used to increase rupture forces if devices are too easily separated from the coverslip. Additionally, micropatterning of biotin-BSA using microcontact stamp printing can be used to allow for sparse bead decoration while providing multiple biotin-streptavidin attachments per bead.

Characterizing Sensor in Shear Flow Chambers.

Lifetime-based Fluorescence Lifetime Imaging FRET (FLIM-FRET) measurements can be performed on microbead-on-spring sensors bound to coverslips. Lifetime measurements of FRET efficiency can take upwards of about approximately 30 seconds, so immobilization can critical for this step. For shear stress studies, sensors can be exposed to shear stress ranging from about approximately 0.1 to 10 dynes/cm$^2$, a common range for both physiologic flow as well as flow in rivers in the United States. To apply known shear stress, a microfluidic shear chamber (Warner Instruments RC-30) can be used.

To characterize FRET efficiency of microbead-on-spring sensors in the across a range of shear stress levels, FRET efficiency of constructs inside the shear chamber can be calculated using FLIM-FRET as well as intensity-based FRET using the ImageJ Precision FRET module (a tool for removing spectral bleed-through or cross-talk for intensity-based FRET studies).FLIM-FRET characterization is least biased by photobleaching, so calibration curves can be developed to relate actual FRET with intensity-based FRET that can be performed using a Nikon Ti2-E microscope. Once calibration curves have been developed, future experiments can rely on intensity-based FRET, plate reader studies and even FACS measure device FRET.

For bead sizes 1 mm, 2 mm, 4 mm, and 8 mm, FRET efficiency versus shear stress can be characterized to determine sensitivity ranges for each microbead-on-spring construct. This calibration can allow for the creation of a range of sensors that are sensitive to desired ranges of shear stress.

Second, increasing levels of fluorophore decoration (e.g., 5, 10, 15, and 20 Cy3/Cy5 fluorophores per spring) can be tested to see if higher levels of decoration lead to tighter alignment between lifetime- and intensity-based measurements.

Cover slip-bound microbead-on-nanospring sensor constructs can provide a real-time readout of the dynamic wall shear stress (WSS) within microfluidic systems, with sensitivity to ultralow WSS increasing with increasing microbead sizes. Intensity-based studies can be biased by fluorophore bleaching, and calibration can be performed using FLIM of immobilized sensors so that the ultra-bright cumulative shear sensor design can be tuned to maximize sensitivity for fluorescent microbead-on-nanospring sensors. Higher density of decoration can increase signal-to-noise for intensity-based FRET. However, if small differences in FRET signal that are measurable with FLIM prove difficult to capture with standard laboratory tools like plate readers, quencher-fluorophore pairs in the aforementioned design rather than donor-acceptor pairs can be considered. In this case, fluorescence can be quenched as shear stress/damage accumulates. Additionally, due to autofluorescence of polystyrene beads, image subtraction routines can be implemented to run before sensor quantification. Dynabeads MyOne microbeads (ThermoFisher) have been shown to provide an extremely low level of autofluorescence, and can be investigated. Alternately, silicone microspheres with minimal autofluorescence can be used.

Hydrodynamic Shear Reporter

Underwater imaging of organisms that live at the bottom of the sea has driven advances in underwater microscopy as well as wide-field imaging of fluorescent organisms like coral. The benefit of wide field imaging is that low-cost, SLR cameras can be modified to remove their internal IR filters. This enables them to be used to capture the time-resolved fluorescence of a submerged system. A modified SLR can be used to measure the magnitude of the principal shear stresses across the surfaces of sensor-decorated test models.

To perform fluorescent imaging, a testbed can be built for imaging that includes a perfused tank system, a strobe for wavelength-specific activation, and an IR-modified digital camera. The basic concept involves wavelength-specific excitation via a strobe light, followed by barrier filtration to remove scattered light and allow the infrared fluorescence signal to pass through. An IR-modified Canon Mark II digital SLR camera (LifePixel Infrared Camera Conversions) can used to capture the resulting fluorescence signal.

For this first task, a sample can be activated using the barrier film-modified strobe for Cy3 excitation wavelength of 550 nm (NightSea filters). An external enhanced infrared barrier filter at 665 nm on the camera can be used to capture the emission of the Cy5 fluorophore resulting from FRET. Assuming uniform coverage with sensors, this testbed can allow for the measurement of the infrared signal above 665 nm and can provide a qualitative description of the variation in wall shear stress. The use of a second external barrier filter that only detects visible light to take the IR and visible range photos in rapid succession can also be investigated. Both images can be used to calculate a ratiometric signal of Cy5:Cy3.

A circulating water tank can be built using commercially-available fish tank, custom inserts and circulating pump. To create a uniform test course, custom acrylic inserts can be assembled inside the tank and sealed using silicone sealant. By varying the pump flow rates, different flow conditions can be generated that simulate marine currents and marine vessel speeds.

Imaging Fluorescent Sensor-Coated Surfaces

Once the testbed has been constructed and scale models have been decorated, imaging tests on models coated with control sensor constructs can be performed. These constructs can be built to permanently report high-FRET or low-FRET (regardless of fluid forces). These controls comprise of simple rectangular tiles decorated with lines of Cy3 and Cy5 that are 10 nm apart and 3 nm apart, for low- and high-FRET, respectively. It is likely that fluorescent images captured with models decorated with low-FRET controls will contain very little signal, whereas models decorated with the high-FRET control will contain strong fluorescent signal. Surface decoration density can be tuned to maximize the fluorescent signal without saturating the image.

The sensor decoration density determined in the control investigation and image nanoscale shear sensor constructs constructed can be utilized with the following sizes of microbeads: 1 to 8 microns in both dark and daylight conditions. For each type of construct, the fluid flow can be made to vary and fluorescent images depicting the distribution of wall shear stresses experienced by the test object can be captured. The result of this development can be a system that resembles a next-generation birefringence study, in which wide-field photography can capture and map critical information about the magnitude of surface shear stresses rather than principle tensile stresses.

If a substantial portion of the strobe's activation signal bleeds through the barrier filter, alternate fluorophore FRET pairs can be constructed. For example, Alexa488 can be used as the donor with Cy3 as the acceptor. This would conform to prior wide-field imaging approaches using a GFP-like fluorophore to test the camera system.

Fluorescent mm-Scale Beads for LiDAR.

Biomimetic shear sensing buoyant beads would offer a novel approach to noninvasive, low-cost sensing of fluidic disturbances. Dispersing mm-scale reporter beads in a body of water can create a floating sensor layer capable of providing a fluorescent signal for monitoring watercraft as well as wildlife. Therefore, theoretical compatibility and feasibility of a bead-based sensor with LiDAR light-activated fluorescence (LIF) can be achieved.

Modifying Sensors to Include DNA-Plate Element to Create all-DNA Sensors

The microbead-on-spring nanosensors can be tunable, but this tunability requires a tradeoff in minimum size, which sets a maximum density of sensor coverage and thus sensor system brightness. The microbead-on-spring sensor approach can be modified by replacing the microbead with a flat DNA origami plate element. These all-DNA fluorescent nanosensors can have overall dimensions less than about approximately 200 microns, and this reduction in size can allow more dense decoration of millimeter-scale spheres whose fluorescence can be characterized in static and disturbed flow.

Square lattice DNA origami can be designed and synthesized with the standard M13 scaffold to create plate elements for the sensors (see, e.g., FIG. 5 (c)). These two-part sensors can be annealed individually and then combined and gel purified using a freeze-and-squeeze gel extraction. Both AFM and TEM imaging can be performed to validate successful structure formation. It is likely that under flow, plate-on-spring sensors can reorient along with principle wall shear stress, and these flat plates can directly experience wall shear stress. Shear force can be equal to the product of shear stress and the area of the plates.

If the all-DNA sensors are unable to detect the low shear forces experienced by untethered buoyant spheres, DNA origami assembly techniques for creating ultralarge multi-scaffold systems to incrementally increase plate area until sensors can detect fluid disturbances can be utilized.

Example 6—Implementation of the Use of Sensor for Identifying Cardiac Wall Shear Stress (WSS) Signatures Nanoscale shear sensors can be introduced into embryonic zebrafish vasculature to map wall shear stress (WSS) throughout early development. An approach is provided that combines multiple advanced techniques including an integrated experimental design that utilizes mechanical design, DNA nanotechnology, coarse grained molecular dynamics simulation, microfluidics, endothelial cell culture, and high-speed light sheet microscopy studies of zebrafish. Nanoscale shear sensors can be designed, fabricated, and calibrated using computationally-designed microfluidic shear chambers. Nanoscale shear sensors are attached to the surfaces of endothelial cells. The nanoscale shear sensors can be used to map the WSS for cell cultures grown in shear flow microchambers. Attachment techniques are described herein that can decorate the vasculature of a system (e.g. zebrafish vasculature) for direct measurement and mapping of endothelial WSS throughout cardiogenesis and valvulogenesis. 4D WSS maps can be compared with wild type maps to identify disease-related alterations in WSS, which can be used for congenital heart disease models with valvular malformations.

Examples of synthesis methodology for producing nanoscale DNA origami shear sensors with tunable sensitivity and tunable fluorescent output are described previously. Computationally-designed microfluidic shear chambers and nanosensors can be used such that the efficiency of Förster resonance energy transfer (FRET) can be used as a quantitative measure of WSS. Nanosensors can be functionalized for attachment to specific binding sites on the membranes of endothelial cells that line a vasculature. Nanosensors can be attached to specific binding sites on the membranes of endothelial cells, the decoration will allow the measurement of spatial patterns of WSS experienced across cells cultured in shear flow chambers.

A method including decorating the endothelium with sensors and using light sheet microscopy to map the WSS in the ventricle and atrium during development of wild type (WT) and mutant models with valve defects can be implemented.

The direct measures of WSS and shear dose experienced by cells in vitro and in vivo, as described herein, can enable researchers to fluorescently track morphology and WSS throughout development in healthy and diseased hearts, and investigate how structural malformations of valves in the heart disrupt the shear signature and, vice versa, how disruptions in the shear signature correlate with altered formation of valves. The methods can enable high-framerate studies of flow-induced mechanical forces without a requirement for a priori structural information in any organ system in zebrafish, with opportunities for extension of this technique to larger animals using non-fluorescent detection strategies like MRI.

The methods provided herein can provide maps of WSS that can be useful for cardiologists planning surgical interventions in adults and children. WSS maps that can provide predictions for how WSS signatures can evolve with time, providing strong evidence that surgery is necessary or unnecessary for a given patient with a given initial WSS profile.

Nanoscale shear sensors can be used for directly measuring WSS and reporting a quantitative ratiometric fluorescence signal as output, which can involve theoretical modeling, computational simulation and experimental measurements of spring element stiffness, sensitivity and noise. The methods can include the development of calibration curves for nanosensors of varying spring stiffness using computationally-designed microfluidic channels. Protocols for attaching functionalized fluorescent nanosensors to cell membranes and glycocalyx of endothelial cells in vitro and in vivo can be developed. WSS in embryonic hearts can be directly measured using high-speed light sheet imaging. Four dimensional "maps" of WSS can be developed for wild type and disease models of valve-related congenital heart disease across multiple stages of embryonic development.

A nanoscale shear sensor can be produced that can attach to the endothelium at one point and therefore be able to rotate freely along the wall to self-orient to the flow. This design can enable direct measurement of WSS in the direction parallel to the fluid flow at the surface. One major benefit of this approach is that it is not necessary to control or track the orientation of the sensor. Mechanically, symmetrical design of a rod-based spring element allows for axial stretch as well as tunable mechanics (e.g., altering the tube section shape or tube length will alter the effect spring element stiffness). The methods can include in vivo decoration of the cell membrane and glycocalyx that enables sensing machinery in the glycocalyx. Mechanosensors can be introduced onto the cell membrane and glycocalyx, so that the WSS can be measured and investigated when the cells experience WSS.

Mechanical Nanosensor Design and Coarse Grain Simulation for Independent Tuning of Sensitivity and Signal Output.

This approach involves the development of a tunable nanospring connected to a flat plate. Shear force experienced at a given level of shear stress is proportional to plate area, so tuning plate area can increase the sensitivity of the device. Independently, the spring element stiffness and positioning of the fluorophores will dictate how much the FRET pairs move in response to the shear force acting on the plate. A major design contribution of this work is that the nanosprings are designed and optimized for maximum deformation of about approximately 4 nm under peak physiological stress that can result the separation change of resident FRET pairs from about approximately 3.5 nm (high-FRET) to 7.5 nm (low-FRET).

For modeling purposes, referring to FIG. 6 (c), the spring element can be divided into cantilever beam-like subsections. Such elements are shorter than their persistence length, and thus exhibit Euler beam-like behavior that can be modeled analytically. Referring to FIG. 6 (d), Coarse-grained molecular dynamics simulations that vary solution ionic condition and temperature can be performed using the open source tool oxDNA. With oxDNA a variety of element geometries can be estimated to computationally model their conformational changes and conformational distributions under load. This can allow for sensitivity optimization across the range of physiological WSS levels. The DNA origami approach also allows for tunable placement of FRET donor and acceptor to maximize the sensitivity of the FRET sensor while avoiding saturation. This approach demonstrates how macromolecular nanosensors can provide tunability and optimization necessary for high performance sensing applications.

Computationally-Designed Microfluidic Test Channels can be Used for Sensor Characterization and Calibration.

Microfluidic shear flow chambers with known shear profiles can be utilized for calibrating our nanosensors. These chambers can used to study shear stress and also to calculate shear dose, the integral of shear magnitude with time. Microfluidic chambers can be fabricated using soft lithography and then these chambers can be decorated with WSS sensors. Known shear stresses can be applied to determine calibration factors for the sensors. The device spring stiffness and plate area can also be iterated and tuned to generate sensors for specific shear regimes. In this way, accuracy and precision can be achieved in the WSS measurements, all without requiring a priori information about the enclosing geometries or flow velocity fields.

Decoration of endothelial cells can be performed using cells in culture. In preliminary data, endothelial cells were decorated with Alexa488 plus a binding strand of ssDNA. Origami tiles decorated with Cy5 were synthesized with and without complementary binding stalks for cell attachment.

Tiles with complementary stalks fluoresce brightly where little fluorescence is visible on tiles without complementary stalks.

Embedding WSS Sensors in Cell Membrane and Glycocalyx.

DNA origami decoration, e.g., attachment of functional moieties to pendant portions of staples, with lipophilic and amphiphilic molecules like porphyrins and cholesterols, respectively, can be used as molecules to anchor DNA in cell membranes. Additionally, functionalizing tethers with lectins can be used as molecules to anchor DNA in cell membranes, since lectins are typically used in visualizing vasculature as they bind readily to glycoproteins that make up the glycocalyx and in the basal membrane of endothelial cells. This opportunity to bind to the glycocalyx is particularly interesting, because cells themselves appear to sense shear using membrane-embedded proteins in the glycocalyx. Therefore the WSS measured at the glycocalyx can potentially be used to investigate what the cells of the vasculature "feel." Additionally, glycocalyx functionalization using a metabolic glycan labeling approach has shown to work in cell cultures and whole animal models. Each functionalization technique can be tested in vitro inside shear flow channels to mimic decoration of the vasculature in vivo.

4D Imaging of Developing Zebrafish Heart can be Achieved Using Light Sheet Microscopy.

The embryonic zebrafish is optically transparent for fluorescent microscopy. Light sheet microscopy can noninvasively image planes of fluorescently-labeled cardiac tissues and blood cells at high speed. Light sheet microscopy can be used to observe organogenesis with cell-level detail at up to about approximately 500 frames per second. In recent years it has become the powerhouse tool for developmental biology, and zebrafish studies of cardiogenesis provide an excellent example of the utility of this method. Optimal decoration strategies for embedding our WSS sensors can be determined within the vasculature of living embryonic zebrafish via light sheet microscopy. Due to the simplicity of this method, it is not necessary to capture full 3D structural information nor measure the 4D fluid velocity profile. For each measurement, the fluorescent readout will provide a ratiometric signal that simultaneously indicates the endothelial structure and the magnitude of the WSS.

Systematic Mapping of Time-Resolved Cardiac Shear Stress Maps for Both WT and Valve Disease Models of Zebrafish.

The vasculatures of wild type and embryonic valve disease zebrafish models can be decorated and conduct time-course surveys using light sheet microscopy can be conducted. Maps of WSS throughout development and at varying layers of the heart can be constructed, from the first heartbeat (72 h) until the embryos are too large and pigmented to easily visualize (up to 7 days post fertilization). The measurements do not require information about the vessel geometry or mechanics. Further, this approach requires neither assumptions about the flow profile nor measurements of flow velocity. The tremendous simplicity of direct WSS measurement can allow investigation of arbitrary, dynamic geometries of any scale, thereby vastly increasing the scope of flow environments that can be characterized (from capillaries to heart valves).

Example 7—Developing Robust Approaches for Surface Decoration of Polymers and Metals In a biophysics laboratory setting, molecular adhesives like biotin and steptavidin are useful for their high rupture strength and biocompatibility. However, the versatile functionalizations of DNA allow for numerous distinct approaches for attaching DNA nanotechnologies to binding surfaces. Utilizing expressed proteins like streptavidin or antibody-antigen pairs allows for strong, highly-specific binding, but their cost may not scale well as large quantities are required. Top candidate approaches for functionalizing can include acrylonitrile butadiene styrene (ABS) and polylactic acid (PLA), polydimethylsiloxane (PDMS) and gold.

Alternative protein-based functionalization techniques include $Ni^{2+}$-nitrilotriacetic acid (NTA) chelation, fluorescein-Anti-FSc antibody binding, Alkyne-Azide binding, and Aptamer-protein binding. Additionally, protein-free methods including thiol-metal binding are possible candidates for large area decoration with DNA origami.

For this task, centimeter-scale test objects in the shape of fish, boats and submarines can be created to investigate decoration strategies. Plastic models can be 3D printed in two materials: ABS and PLA. PDMS silicone models can be molded from 3D-printed cavities, and half of the PDMS models can be sputter coated with gold. Then decoration strategies can be investigated to determine efficient and high-density decoration approaches for reliably adhering DNA origami sensors to these surfaces Example 8—Decorating mm-Scale Beads with Nanosensors To create a dinoflagellate mimic, a biodegradable bead made of poly(D,L-lactide-co-glycolide) (Sigma) can be used. These beads are available in diameters ranging from a few microns up to 500 microns, and the largest beads can be used so as to maximize brightness of signal for an individual bead. These beads can first be visualized using our fluorescence microscopy as well as wide-field imaging to verify that autofluorescence is minimal and to demonstrate that any desired fluorescence is detectable and not susceptible to photobleaching under daylight conditions. Commercially-available PLGA beads are carboxyl decorated, which allows for covalent bonding with a range of protein functionalizations. For this system beads can be coated with streptavidin. Sensors can be assembled on beads, and epifluorescence microscopy can be used to quantify bead fluorescence. If bead autofluorescence are an issue, PDMS spheres can be synthesized, and the autofluorescence of PDMS has been shown to be minimal. For this approach, plasma treatment and subsequent silane-based functionalization can be used.

Example 9—Fluorescent LiDAR

Fluorescent LiDAR is well-established for applications monitoring the upper ocean and terrain, measuring leaf area distribution, and even for wide-area detection of nitroaromatic explosives. ND:YAG lasers typically used in bathymetric LiDAR utilize frequency doubled 1064 nm lasers to achieve 532 nm lasers. Given the peak absorbance of water occurs in the infrared region of about 970 nm, 103 shorter visible wavelengths like 532 nm can penetrate more deeply into water for LiDAR on mapping the bottom of the sea floor.

532 nm is also in the peak excitation range for the FRET donor, Cy3. Therefore, existing mobile and fixed LiDAR systems for bathymetric LiDAR can be utilized for exciting buoyant bead sensors floating near the surface. Typically, high gain photomultiplier tubes (PMTs) are used to capture the backscattered laser photons. Therefore, the only modification a commercial system needs is the application a bandpass filter to the PMT for detecting only the near infrared fluorescent signal. Beyond this LiDAR detection change, the structures must be shown to be bright enough for remote detection. In 2008, a typical 532 nm frequency-doubled LiDAR system delivered 0.3 J of pulse energy to a spot with a 0.2 m diameter at 500 m away. Using a conventional EMCCD, Finger et al. calculated that 200 Nile-red fluorescent microspheres (1 micron size from Molecular Probes) would need to be present for successful detection within a single LiDAR pulse (Finger I, Phillips S, Mobley E, Tucker R, Hess H. Absolute brightness of fluorescent microspheres. *Lab Chip.* 2009; 9(3):476-478. doi: 10.1039/b810219h). Therefore, Finger's method to compare the brightness of our sensors-on-sphere platform to Nile-red fluorescent microbeads can be used to determine the necessary surface concentration of buoyant beads needed. For brightness calculations, an iXON ELife EMCCD camera can be used, which has signal/noise (SNR) equal to one at 4 photons/pixel for a 1 MHz readout.

Signal-per-sphere is expected to far exceed that of a Nile-red microbead, so at maximum it is expected to need 200 spheres per 0.2 diameter surface area of water for detection. If the bead constructs are less bright than commercial Nile-red beads, fluorophore decoration density can be increased to increase surface decoration density. The full range of feasible bouyant bead sizes that smaller than the 500 micron-diameter spheres selected can be determined.

While the present invention is described with reference to several distinct embodiments, those skilled in the art may make modifications and alterations without departing from the scope and spirit. Accordingly, the above detailed description is intended to be illustrative rather than restrictive.

What is claimed is:

1. A micromechanical spring sensor, comprising:
a spring element comprising a nucleic acid and/or nucleic acid analog nanostructure beam pair comprising one or more single-stranded scaffold nucleic acids or nucleic acid analogs, and nucleic acids or nucleic acid analog staples, comprising:
a flexible first beam and a flexible second beam pinned together at two or more spaced-apart pinning locations on the beams and defining unpinned sections of the beams and beam pair between the pinning locations, the beam pair comprising two or more fluorescent donor moieties arranged in the unpinned section of the first beam and two or more quenching acceptor moieties that quench the signal of the donor and which are spatially aligned in the unpinned section of the second beam with a corresponding donor moiety on the first beam, defining a gap distance between the corresponding donor and acceptor moieties;
a first tether attached to the first beam at the unpinned section; and
a second tether attached to the second beam at the unpinned section;
wherein the unpinned section of the beams flex from a closed position with no tensional force applied to the tethers, defining a resting gap distance between the fluorescent donor moieties and the quenching acceptor moieties, to an open position with the application of a tensional force to the tethers where the beams flex apart to an open position with the first and second beam remaining pinned together at the pinning locations, defining a tensioned gap distance, wherein the resting gap distance between the fluorescent donor moieties and the quenching acceptor moieties is less than the tensioned gap distance between the fluorescent donor moieties and the quenching acceptor moieties for at least one pair of corresponding donor and acceptor moieties, such that the sensor produces a detectably different emission spectra when the beams are in the closed position as compared to when the beams are in the open position; and a drag element attached to a tether of one of the beam pairs.

2. The sensor of claim 1, wherein the nucleic acid and/or nucleic acid analog nanostructure is a folded, single-stranded nucleic acid, and wherein the first beam and the second beam are pinned together by pinning staples.

3. The sensor of claim 1, wherein the resting gap distance between the fluorescent donor moieties and the quenching acceptor moieties is less than a Förster critical distance for the donors and acceptors, and the tensioned gap distance between the fluorescent donor moieties and the quenching acceptor moieties is greater than the Förster critical distance for at least one pair of corresponding donor and acceptor moieties, such that the sensor produces a detectably different emission spectra when the beams are in the closed position as compared to when the beams are in the open position.

4. The sensor of claim 1, wherein at least two sets of the corresponding donor and acceptor moieties are arranged in the unpinned section such that different tensional forces applied to the tethers results in different tensioned gap distances for at least two of the corresponding donor and acceptor moieties, such that different positive tensions applied to the tethers produce different emission spectra.

5. The sensor of claim 4, wherein the at least two pairs of the corresponding donor and acceptor moieties are arranged in the unpinned section to produce a regular change in the emission of the sensor with a regular increase in tension applied to the tethers.

6. The sensor of claim 1, further comprising a ligand indirectly or directly attached to the first tether or the second tether.

7. The sensor of claim 1, further comprising biotin linked to the first tether or the second tether.

8. The sensor of claim 1, wherein the drag element is a nucleic acid and/or nucleic acid analog nanostructure.

9. The sensor of claim 1, wherein the drag element comprises a bead or particle.

10. The sensor of claim 1, wherein the drag element is a particle that renders the sensor buoyant.

11. The sensor of claim 1, wherein the drag element is attached to the spring element by a biotin/streptavidin linkage.

12. The sensor of claim 1, wherein the first tether or the second tether anchors the sensor to a surface of a substrate.

13. The sensor of claim 1, wherein the first tether or the second tether anchors the sensor to a cell or tissue.

14. The sensor of claim 13, wherein the cell or tissue is located in an organism.

15. The sensor of claim 13, wherein the cell or tissue is located in a microfluidic chamber.

16. The sensor of claim 1, wherein the fluorescent donor moieties and/or acceptor moieties are a fluorescent protein.

17. A method of measuring a force, comprising:
    exposing the sensor of claim 1 to an environment in which a force is to be measured;
    illuminating the sensor with electromagnetic radiation within the absorption spectrum of the donor: and;
    determining, by measuring emission from the sensor in the emission spectrum of the donor or acceptor, either if a force acts on the sensor in the environment sufficient to flex the beams of the sensor into an open position, and/or the extent of flexing of the beams of the sensor to quantify the force acting on the sensor in the environment.

18. The method of claim 17, wherein the sensor is calibrated to correlate the extent of flexing of the beams of the sensor with force acting on the sensor in an environment.

19. The method of claim 17, wherein the sensor is anchored by the first tether or the second tether to a cell or tissue.

20. The method of claim 19, comprising imaging the cell or tissue at a wavelength within the emission spectrum of the donor or acceptor to evaluate forces acting on the sensors.

* * * * *

SEQUENCE LISTING

```
<160> NUMBER OF SEQ ID NOS: 233

<210> SEQ ID NO 1
<211> LENGTH: 29
<212> TYPE: DNA
<213> ORGANISM: Artificial Sequence
<220> FEATURE:
<223> OTHER INFORMATION: DNA origami staple

<400> SEQUENCE: 1
gaacggaagc gaaaacgtgg cgagaaagg                                       29

<210> SEQ ID NO 2
<211> LENGTH: 34
<212> TYPE: DNA
<213> ORGANISM: Artificial Sequence
<220> FEATURE:
<223> OTHER INFORMATION: DNA origami staple

<400> SEQUENCE: 2
aatcatacag gcaaggcaaa gcttgcgtac cgag                                 34

<210> SEQ ID NO 3
<211> LENGTH: 41
<212> TYPE: DNA
<213> ORGANISM: Artificial Sequence
<220> FEATURE:
<223> OTHER INFORMATION: DNA origami staple

<400> SEQUENCE: 3
cactaaacat ttgtcacgtt aaaaaaggcc ggcgaggagc g                         41

<210> SEQ ID NO 4
<211> LENGTH: 41
<212> TYPE: DNA
<213> ORGANISM: Artificial Sequence
<220> FEATURE:
<223> OTHER INFORMATION: DNA origami staple

<400> SEQUENCE: 4
tatctattag actgaattgc ctttaatatt tagaggcaag t                         41

<210> SEQ ID NO 5
<211> LENGTH: 22
<212> TYPE: DNA
<213> ORGANISM: Artificial Sequence
<220> FEATURE:
<223> OTHER INFORMATION: DNA origami staple
```

<400> SEQUENCE: 5
tagttgcgga ctccgggcgc gt					22

<210> SEQ ID NO 6
<211> LENGTH: 21
<212> TYPE: DNA
<213> ORGANISM: Artificial Sequence
<220> FEATURE:
<223> OTHER INFORMATION: DNA origami staple

<400> SEQUENCE: 6
caaccatgag tccagttaaa t					21

<210> SEQ ID NO 7
<211> LENGTH: 21
<212> TYPE: DNA
<213> ORGANISM: Artificial Sequence
<220> FEATURE:
<223> OTHER INFORMATION: DNA origami staple

<400> SEQUENCE: 7
tgataaaaat tgcgcaactg t					21

<210> SEQ ID NO 8
<211> LENGTH: 21
<212> TYPE: DNA
<213> ORGANISM: Artificial Sequence
<220> FEATURE:
<223> OTHER INFORMATION: DNA origami staple

<400> SEQUENCE: 8
gcgacctatg agtgggtgcg g					21

<210> SEQ ID NO 9
<211> LENGTH: 21
<212> TYPE: DNA
<213> ORGANISM: Artificial Sequence
<220> FEATURE:
<223> OTHER INFORMATION: DNA origami staple

<400> SEQUENCE: 9
agccggagtg taaaacgcca g					21

<210> SEQ ID NO 10
<211> LENGTH: 21
<212> TYPE: DNA
<213> ORGANISM: Artificial Sequence
<220> FEATURE:
<223> OTHER INFORMATION: DNA origami staple

<400> SEQUENCE: 10
gtcaatccat acgaatgtgc t					21

<210> SEQ ID NO 11
<211> LENGTH: 21
<212> TYPE: DNA
<213> ORGANISM: Artificial Sequence
<220> FEATURE:
<223> OTHER INFORMATION: DNA origami staple

<400> SEQUENCE: 11
ctgaccatcc gctcttgggt a					21

<210> SEQ ID NO 12
<211> LENGTH: 41

<210> SEQ ID NO 12
<211> LENGTH: 41
<212> TYPE: DNA
<213> ORGANISM: Artificial Sequence
<220> FEATURE:
<223> OTHER INFORMATION: DNA origami staple

<400> SEQUENCE: 12
caatagaata tattgccttg cagatgagtt tcctccagtc a                            41

<210> SEQ ID NO 13
<211> LENGTH: 41
<212> TYPE: DNA
<213> ORGANISM: Artificial Sequence
<220> FEATURE:
<223> OTHER INFORMATION: DNA origami staple

<400> SEQUENCE: 13
gattaattgc ttcaataagt aggcgcattc gtaagacggc c                            41

<210> SEQ ID NO 14
<211> LENGTH: 32
<212> TYPE: DNA
<213> ORGANISM: Artificial Sequence
<220> FEATURE:
<223> OTHER INFORMATION: DNA origami staple

<400> SEQUENCE: 14
tctagaggat ccccggatgc ctgcaggtcg ac                                      32

<210> SEQ ID NO 15
<211> LENGTH: 21
<212> TYPE: DNA
<213> ORGANISM: Artificial Sequence
<220> FEATURE:
<223> OTHER INFORMATION: DNA origami staple

<400> SEQUENCE: 15
aagggaagat acgccagaat c                                                  21

<210> SEQ ID NO 16
<211> LENGTH: 21
<212> TYPE: DNA
<213> ORGANISM: Artificial Sequence
<220> FEATURE:
<223> OTHER INFORMATION: DNA origami staple

<400> SEQUENCE: 16
tcatggtcag tgattagaca g                                                  21

<210> SEQ ID NO 17
<211> LENGTH: 21
<212> TYPE: DNA
<213> ORGANISM: Artificial Sequence
<220> FEATURE:
<223> OTHER INFORMATION: DNA origami staple

<400> SEQUENCE: 17
ccattgagag tctaggaggc c                                                  21

<210> SEQ ID NO 18
<211> LENGTH: 21
<212> TYPE: DNA
<213> ORGANISM: Artificial Sequence
<220> FEATURE:
<223> OTHER INFORMATION: DNA origami staple

<400> SEQUENCE: 18

```
ccagaattaa ccggaatcag a                                              21

<210> SEQ ID NO 19
<211> LENGTH: 21
<212> TYPE: DNA
<213> ORGANISM: Artificial Sequence
<220> FEATURE:
<223> OTHER INFORMATION: DNA origami staple

<400> SEQUENCE: 19
tatcggcttt gattataacg t                                              21

<210> SEQ ID NO 20
<211> LENGTH: 22
<212> TYPE: DNA
<213> ORGANISM: Artificial Sequence
<220> FEATURE:
<223> OTHER INFORMATION: DNA origami staple

<400> SEQUENCE: 20
aacatcactt gcgcatggtt gc                                             22

<210> SEQ ID NO 21
<211> LENGTH: 21
<212> TYPE: DNA
<213> ORGANISM: Artificial Sequence
<220> FEATURE:
<223> OTHER INFORMATION: DNA origami staple

<400> SEQUENCE: 21
attcataaaa cgaaatattt t                                              21

<210> SEQ ID NO 22
<211> LENGTH: 21
<212> TYPE: DNA
<213> ORGANISM: Artificial Sequence
<220> FEATURE:
<223> OTHER INFORMATION: DNA origami staple

<400> SEQUENCE: 22
tactgccaaa aataatattt a                                              21

<210> SEQ ID NO 23
<211> LENGTH: 21
<212> TYPE: DNA
<213> ORGANISM: Artificial Sequence
<220> FEATURE:
<223> OTHER INFORMATION: DNA origami staple

<400> SEQUENCE: 23
tttagagact attaacagga a                                              21

<210> SEQ ID NO 24
<211> LENGTH: 21
<212> TYPE: DNA
<213> ORGANISM: Artificial Sequence
<220> FEATURE:
<223> OTHER INFORMATION: DNA origami staple

<400> SEQUENCE: 24
agagggagcg gatgataatc a                                              21

<210> SEQ ID NO 25
<211> LENGTH: 21
<212> TYPE: DNA
<213> ORGANISM: Artificial Sequence
```

```
<220> FEATURE:
<223> OTHER INFORMATION: DNA origami staple

<400> SEQUENCE: 25
ttttgctaag aggtcaatca t                                             21

<210> SEQ ID NO 26
<211> LENGTH: 21
<212> TYPE: DNA
<213> ORGANISM: Artificial Sequence
<220> FEATURE:
<223> OTHER INFORMATION: DNA origami staple

<400> SEQUENCE: 26
aaaacctcaa ataggtaatc g                                             21

<210> SEQ ID NO 27
<211> LENGTH: 21
<212> TYPE: DNA
<213> ORGANISM: Artificial Sequence
<220> FEATURE:
<223> OTHER INFORMATION: DNA origami staple

<400> SEQUENCE: 27
ctcgttgagc ttccaaacaa g                                             21

<210> SEQ ID NO 28
<211> LENGTH: 21
<212> TYPE: DNA
<213> ORGANISM: Artificial Sequence
<220> FEATURE:
<223> OTHER INFORMATION: DNA origami staple

<400> SEQUENCE: 28
aagagccgga agctcattgc c                                             21

<210> SEQ ID NO 29
<211> LENGTH: 21
<212> TYPE: DNA
<213> ORGANISM: Artificial Sequence
<220> FEATURE:
<223> OTHER INFORMATION: DNA origami staple

<400> SEQUENCE: 29
taatgcattg ctcgagaggg t                                             21

<210> SEQ ID NO 30
<211> LENGTH: 21
<212> TYPE: DNA
<213> ORGANISM: Artificial Sequence
<220> FEATURE:
<223> OTHER INFORMATION: DNA origami staple

<400> SEQUENCE: 30
tttaggtcat tttctagctg a                                             21

<210> SEQ ID NO 31
<211> LENGTH: 21
<212> TYPE: DNA
<213> ORGANISM: Artificial Sequence
<220> FEATURE:
<223> OTHER INFORMATION: DNA origami staple

<400> SEQUENCE: 31
agaaagagct taatcaatat g                                             21
```

```
<210> SEQ ID NO 32
<211> LENGTH: 21
<212> TYPE: DNA
<213> ORGANISM: Artificial Sequence
<220> FEATURE:
<223> OTHER INFORMATION: DNA origami staple

<400> SEQUENCE: 32
cggaacgctg tagccggaga c                                      21

<210> SEQ ID NO 33
<211> LENGTH: 21
<212> TYPE: DNA
<213> ORGANISM: Artificial Sequence
<220> FEATURE:
<223> OTHER INFORMATION: DNA origami staple

<400> SEQUENCE: 33
tacgttaata tgcgattcaa a                                      21

<210> SEQ ID NO 34
<211> LENGTH: 21
<212> TYPE: DNA
<213> ORGANISM: Artificial Sequence
<220> FEATURE:
<223> OTHER INFORMATION: DNA origami staple

<400> SEQUENCE: 34
aggacggtct ggacctgagt a                                      21

<210> SEQ ID NO 35
<211> LENGTH: 21
<212> TYPE: DNA
<213> ORGANISM: Artificial Sequence
<220> FEATURE:
<223> OTHER INFORMATION: DNA origami staple

<400> SEQUENCE: 35
aactggtaac agttcatata t                                      21

<210> SEQ ID NO 36
<211> LENGTH: 21
<212> TYPE: DNA
<213> ORGANISM: Artificial Sequence
<220> FEATURE:
<223> OTHER INFORMATION: DNA origami staple

<400> SEQUENCE: 36
attaccgcga acgggataaa a                                      21

<210> SEQ ID NO 37
<211> LENGTH: 21
<212> TYPE: DNA
<213> ORGANISM: Artificial Sequence
<220> FEATURE:
<223> OTHER INFORMATION: DNA origami staple

<400> SEQUENCE: 37
tttcaagacc attgaagcct t                                      21

<210> SEQ ID NO 38
<211> LENGTH: 21
<212> TYPE: DNA
<213> ORGANISM: Artificial Sequence
<220> FEATURE:
<223> OTHER INFORMATION: DNA origami staple
```

```
<400> SEQUENCE: 38
attgggaatg gtccctgta a                                              21

<210> SEQ ID NO 39
<211> LENGTH: 21
<212> TYPE: DNA
<213> ORGANISM: Artificial Sequence
<220> FEATURE:
<223> OTHER INFORMATION: DNA origami staple

<400> SEQUENCE: 39 aaacaccctat attgttgtac c                                            21

<210> SEQ ID NO 40
<211> LENGTH: 21
<212> TYPE: DNA
<213> ORGANISM: Artificial Sequence
<220> FEATURE:
<223> OTHER INFORMATION: DNA origami staple

<400> SEQUENCE: 40
aataaggagc tgatcagagc a                                             21

<210> SEQ ID NO 41
<211> LENGTH: 21
<212> TYPE: DNA
<213> ORGANISM: Artificial Sequence
<220> FEATURE:
<223> OTHER INFORMATION: DNA origami staple

<400> SEQUENCE: 41
aacaaattct actgcaaaat t                                             21

<210> SEQ ID NO 42
<211> LENGTH: 21
<212> TYPE: DNA
<213> ORGANISM: Artificial Sequence
<220> FEATURE:
<223> OTHER INFORMATION: DNA origami staple

<400> SEQUENCE: 42
ggcgctaagg gattggccac c                                             21

<210> SEQ ID NO 43
<211> LENGTH: 42
<212> TYPE: DNA
<213> ORGANISM: Artificial Sequence
<220> FEATURE:
<223> OTHER INFORMATION: DNA origami staple

<400> SEQUENCE: 43
agcttgcgaa ccctgcgcgt aaccaccact cgttattgta gc                      42

<210> SEQ ID NO 44
<211> LENGTH: 42
<212> TYPE: DNA
<213> ORGANISM: Artificial Sequence
<220> FEATURE:
<223> OTHER INFORMATION: DNA origami staple

<400> SEQUENCE: 44
tcttaaaaaa aacccgcgct taatgcgcga gcacgtagta at                      42

<210> SEQ ID NO 45
```

```
<211> LENGTH: 42
<212> TYPE: DNA
<213> ORGANISM: Artificial Sequence
<220> FEATURE:
<223> OTHER INFORMATION: DNA origami staple

<400> SEQUENCE: 45
cgatatatgt tgttaccaat aggaacgcat aagcacaggt ct                            42

<210> SEQ ID NO 46
<211> LENGTH: 21
<212> TYPE: DNA
<213> ORGANISM: Artificial Sequence
<220> FEATURE:
<223> OTHER INFORMATION: DNA origami staple

<400> SEQUENCE: 46
acgccagtaa atcgttcatt t                                                  21

<210> SEQ ID NO 47
<211> LENGTH: 21
<212> TYPE: DNA
<213> ORGANISM: Artificial Sequence
<220> FEATURE:
<223> OTHER INFORMATION: DNA origami staple

<400> SEQUENCE: 47
cgacgtttaa agccaaaggt g                                                  21

<210> SEQ ID NO 48
<211> LENGTH: 21
<212> TYPE: DNA
<213> ORGANISM: Artificial Sequence
<220> FEATURE:
<223> OTHER INFORMATION: DNA origami staple

<400> SEQUENCE: 48
agtgccaaga attaaatagt a                                                  21

<210> SEQ ID NO 49
<211> LENGTH: 31
<212> TYPE: DNA
<213> ORGANISM: Artificial Sequence
<220> FEATURE:
<223> OTHER INFORMATION: DNA origami staple

<400> SEQUENCE: 49
acaagaaccg gatattcatt aacatccaat a                                       31

<210> SEQ ID NO 50
<211> LENGTH: 31
<212> TYPE: DNA
<213> ORGANISM: Artificial Sequence
<220> FEATURE:
<223> OTHER INFORMATION: DNA origami staple

<400> SEQUENCE: 50
ctgagaagtg tttttataaa aatacctaca t                                       31

<210> SEQ ID NO 51
<211> LENGTH: 42
<212> TYPE: DNA
<213> ORGANISM: Artificial Sequence
<220> FEATURE:
<223> OTHER INFORMATION: DNA origami staple

<400> SEQUENCE: 51
```
gattaagggc gctgcttgac ggggaaagct ccaaaaaaac gc                              42

<210> SEQ ID NO 52
<211> LENGTH: 42
<212> TYPE: DNA
<213> ORGANISM: Artificial Sequence
<220> FEATURE:
<223> OTHER INFORMATION: DNA origami staple

<400> SEQUENCE: 52
gcgggatcac gctaaaggga gcccccgtgt atcgaccgcc ag                              42

<210> SEQ ID NO 53
<211> LENGTH: 42
<212> TYPE: DNA
<213> ORGANISM: Artificial Sequence
<220> FEATURE:
<223> OTHER INFORMATION: DNA origami staple

<400> SEQUENCE: 53
gctttccacc cgcgtctatc aaaatcgttt cgagggtaat at                              42

<210> SEQ ID NO 54
<211> LENGTH: 42
<212> TYPE: DNA
<213> ORGANISM: Artificial Sequence
<220> FEATURE:
<223> OTHER INFORMATION: DNA origami staple

<400> SEQUENCE: 54
tttgaccgct acaaacgtca aagggcgcag cttgactcaa ac                              42

<210> SEQ ID NO 55
<211> LENGTH: 42
<212> TYPE: DNA
<213> ORGANISM: Artificial Sequence
<220> FEATURE:
<223> OTHER INFORMATION: DNA origami staple

<400> SEQUENCE: 55
acattaaatt tttctattaa agaacgtgcc gacaccctca aa                              42

<210> SEQ ID NO 56
<211> LENGTH: 42
<212> TYPE: DNA
<213> ORGANISM: Artificial Sequence
<220> FEATURE:
<223> OTHER INFORMATION: DNA origami staple

<400> SEQUENCE: 56
aattgttttt ttaccagttt ggaacaacgc ccactcataa at                              42

<210> SEQ ID NO 57
<211> LENGTH: 42
<212> TYPE: DNA
<213> ORGANISM: Artificial Sequence
<220> FEATURE:
<223> OTHER INFORMATION: DNA origami staple

<400> SEQUENCE: 57
gattgtcatc aaagagatag ggttgagttc ggtcgcgtcc aa                              42

<210> SEQ ID NO 58
<211> LENGTH: 42
<212> TYPE: DNA

```
<213> ORGANISM: Artificial Sequence
<220> FEATURE:
<223> OTHER INFORMATION: DNA origami staple

<400> SEQUENCE: 58
gaaaagggcc ttctataaat caaaagagga gttagtaaaa tg                              42

<210> SEQ ID NO 59
<211> LENGTH: 42
<212> TYPE: DNA
<213> ORGANISM: Artificial Sequence
<220> FEATURE:
<223> OTHER INFORMATION: DNA origami staple

<400> SEQUENCE: 59
atgtaccatc aactccgaaa tcggcaaggg atcggttttg cc                              42

<210> SEQ ID NO 60
<211> LENGTH: 42
<212> TYPE: DNA
<213> ORGANISM: Artificial Sequence
<220> FEATURE:
<223> OTHER INFORMATION: DNA origami staple

<400> SEQUENCE: 60
taaaacagta acaaaaatcc tgtttgagaa agaccgagag gc                              42

<210> SEQ ID NO 61
<211> LENGTH: 42
<212> TYPE: DNA
<213> ORGANISM: Artificial Sequence
<220> FEATURE:
<223> OTHER INFORMATION: DNA origami staple

<400> SEQUENCE: 61
agaatcccgt ggggctggtt tgccccaggt agcacgacga ta                              42

<210> SEQ ID NO 62
<211> LENGTH: 42
<212> TYPE: DNA
<213> ORGANISM: Artificial Sequence
<220> FEATURE:
<223> OTHER INFORMATION: DNA origami staple

<400> SEQUENCE: 62
tgagagtgac cgtgagttgc agcaagcttt gaggtcataa cc                              42

<210> SEQ ID NO 63
<211> LENGTH: 42
<212> TYPE: DNA
<213> ORGANISM: Artificial Sequence
<220> FEATURE:
<223> OTHER INFORMATION: DNA origami staple

<400> SEQUENCE: 63
aaaggccgtt ggtcttcacc gcctggccat gagggcata gt                               42

<210> SEQ ID NO 64
<211> LENGTH: 42
<212> TYPE: DNA
<213> ORGANISM: Artificial Sequence
<220> FEATURE:
<223> OTHER INFORMATION: DNA origami staple

<400> SEQUENCE: 64
agctatcgta accgacgggc aacagctcgg gtaataacgc ca                              42
```

<210> SEQ ID NO 65
<211> LENGTH: 42
<212> TYPE: DNA
<213> ORGANISM: Artificial Sequence
<220> FEATURE:
<223> OTHER INFORMATION: DNA origami staple

<400> SEQUENCE: 65
taaattttga gggggttttt cttttcacta cgaacattca ac                              42

<210> SEQ ID NO 66
<211> LENGTH: 42
<212> TYPE: DNA
<213> ORGANISM: Artificial Sequence
<220> FEATURE:
<223> OTHER INFORMATION: DNA origami staple

<400> SEQUENCE: 66
atattccggc ctcttgcgta ttgggcgacg aaagagttga ga                              42

<210> SEQ ID NO 67
<211> LENGTH: 42
<212> TYPE: DNA
<213> ORGANISM: Artificial Sequence
<220> FEATURE:
<223> OTHER INFORMATION: DNA origami staple

<400> SEQUENCE: 67
agtcaaccag ccacaacgcg cggggagact aaaattacag gt                              42

<210> SEQ ID NO 68
<211> LENGTH: 42
<212> TYPE: DNA
<213> ORGANISM: Artificial Sequence
<220> FEATURE:
<223> OTHER INFORMATION: DNA origami staple

<400> SEQUENCE: 68
agggtgcttc tggcagctgc attaatgccc cagccgaact aa                              42

<210> SEQ ID NO 69
<211> LENGTH: 42
<212> TYPE: DNA
<213> ORGANISM: Artificial Sequence
<220> FEATURE:
<223> OTHER INFORMATION: DNA origami staple

<400> SEQUENCE: 69
atgtgtcaaa gcgcagtcgg gaaacctcga aacagaaaaa tc                              42

<210> SEQ ID NO 70
<211> LENGTH: 42
<212> TYPE: DNA
<213> ORGANISM: Artificial Sequence
<220> FEATURE:
<223> OTHER INFORMATION: DNA origami staple

<400> SEQUENCE: 70
tttaaaggct gcgttgcgct cactgccttt gtattaccag tc                              42

<210> SEQ ID NO 71
<211> LENGTH: 42
<212> TYPE: DNA
<213> ORGANISM: Artificial Sequence
<220> FEATURE:

```
<223> OTHER INFORMATION: DNA origami staple

<400> SEQUENCE: 71
atttttggcg atcagctaac tcacattttg tgtcatttta ag          42

<210> SEQ ID NO 72
<211> LENGTH: 42
<212> TYPE: DNA
<213> ORGANISM: Artificial Sequence
<220> FEATURE:
<223> OTHER INFORMATION: DNA origami staple

<400> SEQUENCE: 72
tatttccgct attgcctggg gtgcctagct ccatcattgt ga          42

<210> SEQ ID NO 73
<211> LENGTH: 42
<212> TYPE: DNA
<213> ORGANISM: Artificial Sequence
<220> FEATURE:
<223> OTHER INFORMATION: DNA origami staple

<400> SEQUENCE: 73
tactttaagg ggggccggaa gcataaaacg aggctggttt aa          42

<210> SEQ ID NO 74
<211> LENGTH: 42
<212> TYPE: DNA
<213> ORGANISM: Artificial Sequence
<220> FEATURE:
<223> OTHER INFORMATION: DNA origami staple

<400> SEQUENCE: 74
aaaaacgatt aagacaattc cacacaaata agggagtagt aa          42

<210> SEQ ID NO 75
<211> LENGTH: 42
<212> TYPE: DNA
<213> ORGANISM: Artificial Sequence
<220> FEATURE:
<223> OTHER INFORMATION: DNA origami staple

<400> SEQUENCE: 75
taaagcggtt ttcgtgtgaa attgttaact ttgactgacg ag          42

<210> SEQ ID NO 76
<211> LENGTH: 42
<212> TYPE: DNA
<213> ORGANISM: Artificial Sequence
<220> FEATURE:
<223> OTHER INFORMATION: DNA origami staple

<400> SEQUENCE: 76
aagcaagtaa aactcatggt catagctacg gtgtattcag tg          42

<210> SEQ ID NO 77
<211> LENGTH: 21
<212> TYPE: DNA
<213> ORGANISM: Artificial Sequence
<220> FEATURE:
<223> OTHER INFORMATION: DNA origami staple

<400> SEQUENCE: 77
ctcgaatagg ctgatcaacg t                                 21
```

```
<210> SEQ ID NO 78
<211> LENGTH: 42
<212> TYPE: DNA
<213> ORGANISM: Artificial Sequence
<220> FEATURE:
<223> OTHER INFORMATION: DNA origami staple

<400> SEQUENCE: 78
gtagcgggct aaacgtccat cacgcaaaca atattgttta tc                    42

<210> SEQ ID NO 79
<211> LENGTH: 21
<212> TYPE: DNA
<213> ORGANISM: Artificial Sequence
<220> FEATURE:
<223> OTHER INFORMATION: DNA origami staple

<400> SEQUENCE: 79
aatacttcct tgctgtgaat t                                           21

<210> SEQ ID NO 80
<211> LENGTH: 20
<212> TYPE: DNA
<213> ORGANISM: Artificial Sequence
<220> FEATURE:
<223> OTHER INFORMATION: DNA origami staple

<400> SEQUENCE: 80
tctgagtaga agaataccga                                             20

<210> SEQ ID NO 81
<211> LENGTH: 41
<212> TYPE: DNA
<213> ORGANISM: Artificial Sequence
<220> FEATURE:
<223> OTHER INFORMATION: DNA origami staple

<400> SEQUENCE: 81
gttaaaattc gcttttaaac agttcagtga atccatgaca a                     41

<210> SEQ ID NO 82
<211> LENGTH: 42
<212> TYPE: DNA
<213> ORGANISM: Artificial Sequence
<220> FEATURE:
<223> OTHER INFORMATION: DNA origami staple

<400> SEQUENCE: 82
cagctcaaaa cgttgaatga ccataaatgg aatcggcata ac                    42

<210> SEQ ID NO 83
<211> LENGTH: 21
<212> TYPE: DNA
<213> ORGANISM: Artificial Sequence
<220> FEATURE:
<223> OTHER INFORMATION: DNA origami staple

<400> SEQUENCE: 83
ttaccctctg gatagctgag g                                           21

<210> SEQ ID NO 84
<211> LENGTH: 42
<212> TYPE: DNA
<213> ORGANISM: Artificial Sequence
<220> FEATURE:
<223> OTHER INFORMATION: DNA origami staple
```

<400> SEQUENCE: 84
cgcgtctccc caaatagtc agaagcaagg taataaaggc cg         42

<210> SEQ ID NO 85
<211> LENGTH: 42
<212> TYPE: DNA
<213> ORGANISM: Artificial Sequence
<220> FEATURE:
<223> OTHER INFORMATION: DNA origami staple

<400> SEQUENCE: 85
cagctttccc ggtttgcatc aaaaagataa aagaatcacc ct         42

<210> SEQ ID NO 86
<211> LENGTH: 42
<212> TYPE: DNA
<213> ORGANISM: Artificial Sequence
<220> FEATURE:
<223> OTHER INFORMATION: DNA origami staple

<400> SEQUENCE: 86
gtgagcgtag catgaagccc gaaagactaa aatagagcat cg         42

<210> SEQ ID NO 87
<211> LENGTH: 42
<212> TYPE: DNA
<213> ORGANISM: Artificial Sequence
<220> FEATURE:
<223> OTHER INFORMATION: DNA origami staple

<400> SEQUENCE: 87
ggattctgat gaactcgcgt tttaattcta ccagaacggc ta         42

<210> SEQ ID NO 88
<211> LENGTH: 42
<212> TYPE: DNA
<213> ORGANISM: Artificial Sequence
<220> FEATURE:
<223> OTHER INFORMATION: DNA origami staple

<400> SEQUENCE: 88
ggcggattct ggagaaagcg aaccagacaa cactaactaa ag         42

<210> SEQ ID NO 89
<211> LENGTH: 42
<212> TYPE: DNA
<213> ORGANISM: Artificial Sequence
<220> FEATURE:
<223> OTHER INFORMATION: DNA origami staple

<400> SEQUENCE: 89
taggtcatat caggaaactc caacaggtat tacgaaagtt tc         42

<210> SEQ ID NO 90
<211> LENGTH: 42
<212> TYPE: DNA
<213> ORGANISM: Artificial Sequence
<220> FEATURE:
<223> OTHER INFORMATION: DNA origami staple

<400> SEQUENCE: 90
ggcgcatttt tgagagagag tacctttaag atacaaatac gt         42

<210> SEQ ID NO 91
<211> LENGTH: 42

```
<212> TYPE: DNA
<213> ORGANISM: Artificial Sequence
<220> FEATURE:
<223> OTHER INFORMATION: DNA origami staple

<400> SEQUENCE: 91
tgccagtaat gccgcttttg ataagaggaa taccaggcac ca                              42

<210> SEQ ID NO 92
<211> LENGTH: 42
<212> TYPE: DNA
<213> ORGANISM: Artificial Sequence
<220> FEATURE:
<223> OTHER INFORMATION: DNA origami staple

<400> SEQUENCE: 92
acagtataac cgtttgcgga tggcttagat tcatcaggca aa                              42

<210> SEQ ID NO 93
<211> LENGTH: 42
<212> TYPE: DNA
<213> ORGANISM: Artificial Sequence
<220> FEATURE:
<223> OTHER INFORMATION: DNA origami staple

<400> SEQUENCE: 93
tcgcactatc accattgctg aatataataa cattcactc at                               42

<210> SEQ ID NO 94
<211> LENGTH: 42
<212> TYPE: DNA
<213> ORGANISM: Artificial Sequence
<220> FEATURE:
<223> OTHER INFORMATION: DNA origami staple

<400> SEQUENCE: 94
ggcaccgaga aaggctcaac atgttttaaa taaaagatta ta                              42

<210> SEQ ID NO 95
<211> LENGTH: 42
<212> TYPE: DNA
<213> ORGANISM: Artificial Sequence
<220> FEATURE:
<223> OTHER INFORMATION: DNA origami staple

<400> SEQUENCE: 95
aaccaggagg taaaaactaa agtacggttt gggaaaagta ca                              42

<210> SEQ ID NO 96
<211> LENGTH: 42
<212> TYPE: DNA
<213> ORGANISM: Artificial Sequence
<220> FEATURE:
<223> OTHER INFORMATION: DNA origami staple

<400> SEQUENCE: 96
ccattcatgc aatgagtttc attccatact cattacatcg cc                              42

<210> SEQ ID NO 97
<211> LENGTH: 42
<212> TYPE: DNA
<213> ORGANISM: Artificial Sequence
<220> FEATURE:
<223> OTHER INFORMATION: DNA origami staple

<400> SEQUENCE: 97
```
tgggaagaga acccctgattc ccaattctttt atgcggaaat cc    42

<210> SEQ ID NO 98
<211> LENGTH: 42
<212> TYPE: DNA
<213> ORGANISM: Artificial Sequence
<220> FEATURE:
<223> OTHER INFORMATION: DNA origami staple

<400> SEQUENCE: 98
gcctcttaac gcaaagtaga tttagtttct ttaatgttac tt    42

<210> SEQ ID NO 99
<211> LENGTH: 42
<212> TYPE: DNA
<213> ORGANISM: Artificial Sequence
<220> FEATURE:
<223> OTHER INFORMATION: DNA origami staple

<400> SEQUENCE: 99
ctggcgatgc gggaagatac atttcgcact tgagagcaga cg    42

<210> SEQ ID NO 100
<211> LENGTH: 42
<212> TYPE: DNA
<213> ORGANISM: Artificial Sequence
<220> FEATURE:
<223> OTHER INFORMATION: DNA origami staple

<400> SEQUENCE: 100
gcaaggcatt atgaaataac ctgtttagca gaacgaaccg aa    42

<210> SEQ ID NO 101
<211> LENGTH: 38
<212> TYPE: DNA
<213> ORGANISM: Artificial Sequence
<220> FEATURE:
<223> OTHER INFORMATION: DNA origami staple

<400> SEQUENCE: 101
acatggcttt tgatgatact tcatcaagag taatcttg    38

<210> SEQ ID NO 102
<211> LENGTH: 24
<212> TYPE: DNA
<213> ORGANISM: Artificial Sequence
<220> FEATURE:
<223> OTHER INFORMATION: DNA origami staple

<400> SEQUENCE: 102
tttgacctcc aagaaaatgc tcaa    24

<210> SEQ ID NO 103
<211> LENGTH: 20
<212> TYPE: DNA
<213> ORGANISM: Artificial Sequence
<220> FEATURE:
<223> OTHER INFORMATION: DNA origami staple

<400> SEQUENCE: 103
ttgaaaacaa ctcaatagaa    20

<210> SEQ ID NO 104
<211> LENGTH: 21
<212> TYPE: DNA
<213> ORGANISM: Artificial Sequence

```
<220> FEATURE:
<223> OTHER INFORMATION: DNA origami staple

<400> SEQUENCE: 104
tggtcaggcc cgaacaacag t                                              21

<210> SEQ ID NO 105
<211> LENGTH: 20
<212> TYPE: DNA
<213> ORGANISM: Artificial Sequence
<220> FEATURE:
<223> OTHER INFORMATION: DNA origami staple

<400> SEQUENCE: 105
tcaaacaaag tttgggattt                                                20

<210> SEQ ID NO 106
<211> LENGTH: 20
<212> TYPE: DNA
<213> ORGANISM: Artificial Sequence
<220> FEATURE:
<223> OTHER INFORMATION: DNA origami staple

<400> SEQUENCE: 106
taattctttt gcgtagtaaa                                                20

<210> SEQ ID NO 107
<211> LENGTH: 42
<212> TYPE: DNA
<213> ORGANISM: Artificial Sequence
<220> FEATURE:
<223> OTHER INFORMATION: DNA origami staple

<400> SEQUENCE: 107
aaagacattt atcaagaata taaagtaccc agaagttttg tc                       42

<210> SEQ ID NO 108
<211> LENGTH: 42
<212> TYPE: DNA
<213> ORGANISM: Artificial Sequence
<220> FEATURE:
<223> OTHER INFORMATION: DNA origami staple

<400> SEQUENCE: 108
ttcatatctg aacacatttt cgagccagtc atattagtta gc                       42

<210> SEQ ID NO 109
<211> LENGTH: 42
<212> TYPE: DNA
<213> ORGANISM: Artificial Sequence
<220> FEATURE:
<223> OTHER INFORMATION: DNA origami staple

<400> SEQUENCE: 109
tttgtcacca tcctaacatg taatttagga tggcacattc ca                       42

<210> SEQ ID NO 110
<211> LENGTH: 42
<212> TYPE: DNA
<213> ORGANISM: Artificial Sequence
<220> FEATURE:
<223> OTHER INFORMATION: DNA origami staple

<400> SEQUENCE: 110
gacaccatag aaacatcgcc atatttaatc ctgattacaa ac                       42
```

<210> SEQ ID NO 111
<211> LENGTH: 42
<212> TYPE: DNA
<213> ORGANISM: Artificial Sequence
<220> FEATURE:
<223> OTHER INFORMATION: DNA origami staple

<400> SEQUENCE: 111
aacatatctg tcttaacagt agggcttatt ctgaaaacac tg                    42

<210> SEQ ID NO 112
<211> LENGTH: 42
<212> TYPE: DNA
<213> ORGANISM: Artificial Sequence
<220> FEATURE:
<223> OTHER INFORMATION: DNA origami staple

<400> SEQUENCE: 112
aaatacaaga acggaccagt ataaagccga acctacaata gg                    42

<210> SEQ ID NO 113
<211> LENGTH: 42
<212> TYPE: DNA
<213> ORGANISM: Artificial Sequence
<220> FEATURE:
<223> OTHER INFORMATION: DNA origami staple

<400> SEQUENCE: 113
cagtatgacc gcacatatgc gttatacatt tgcaccattt tc                    42

<210> SEQ ID NO 114
<211> LENGTH: 42
<212> TYPE: DNA
<213> ORGANISM: Artificial Sequence
<220> FEATURE:
<223> OTHER INFORMATION: DNA origami staple

<400> SEQUENCE: 114
tgattaacaa gccgagaaaa agcctgttaa gaaatcaccc tc                    42

<210> SEQ ID NO 115
<211> LENGTH: 42
<212> TYPE: DNA
<213> ORGANISM: Artificial Sequence
<220> FEATURE:
<223> OTHER INFORMATION: DNA origami staple

<400> SEQUENCE: 115
gaataccgta ggaaaacacc ggaatcatgg tttaaaaccg cc                    42

<210> SEQ ID NO 116
<211> LENGTH: 42
<212> TYPE: DNA
<213> ORGANISM: Artificial Sequence
<220> FEATURE:
<223> OTHER INFORMATION: DNA origami staple

<400> SEQUENCE: 116
cgaggaaaat agcaataagg cgttaaatac agtaagttta gt                    42

<210> SEQ ID NO 117
<211> LENGTH: 42
<212> TYPE: DNA
<213> ORGANISM: Artificial Sequence
<220> FEATURE:
<223> OTHER INFORMATION: DNA origami staple

```
<400> SEQUENCE: 117
acaaagtaga aggcgaaata ccgaccgttc gggaggtgta tc                              42

<210> SEQ ID NO 118
<211> LENGTH: 42
<212> TYPE: DNA
<213> ORGANISM: Artificial Sequence
<220> FEATURE:
<223> OTHER INFORMATION: DNA origami staple

<400> SEQUENCE: 118
gaaaagtaag aacgctgacc taaatttatc gcctgtataa gt                              42

<210> SEQ ID NO 119
<211> LENGTH: 42
<212> TYPE: DNA
<213> ORGANISM: Artificial Sequence
<220> FEATURE:
<223> OTHER INFORMATION: DNA origami staple

<400> SEQUENCE: 119
tcttaccgaa cctctatttt agttaattca agttaaagtg cc                              42

<210> SEQ ID NO 120
<211> LENGTH: 20
<212> TYPE: DNA
<213> ORGANISM: Artificial Sequence
<220> FEATURE:
<223> OTHER INFORMATION: DNA origami staple

<400> SEQUENCE: 120
acttttggcg aattttgctc                                                       20

<210> SEQ ID NO 121
<211> LENGTH: 20
<212> TYPE: DNA
<213> ORGANISM: Artificial Sequence
<220> FEATURE:
<223> OTHER INFORMATION: DNA origami staple

<400> SEQUENCE: 121
caagacacct gagaaggatt                                                       20

<210> SEQ ID NO 122
<211> LENGTH: 20
<212> TYPE: DNA
<213> ORGANISM: Artificial Sequence
<220> FEATURE:
<223> OTHER INFORMATION: DNA origami staple

<400> SEQUENCE: 122
atgctggaaa caagaggctg                                                       20

<210> SEQ ID NO 123
<211> LENGTH: 20
<212> TYPE: DNA
<213> ORGANISM: Artificial Sequence
<220> FEATURE:
<223> OTHER INFORMATION: DNA origami staple

<400> SEQUENCE: 123
gggttaaaat taatctgaaa                                                       20

<210> SEQ ID NO 124
```

<210> SEQ ID NO 124
<211> LENGTH: 20
<212> TYPE: DNA
<213> ORGANISM: Artificial Sequence
<220> FEATURE:
<223> OTHER INFORMATION: DNA origami staple

<400> SEQUENCE: 124
ttttaattca tttgcctatt                                              20

<210> SEQ ID NO 125
<211> LENGTH: 42
<212> TYPE: DNA
<213> ORGANISM: Artificial Sequence
<220> FEATURE:
<223> OTHER INFORMATION: DNA origami staple

<400> SEQUENCE: 125
ggagaatagt tacaatcaaa atcataggaa tggaatataa ac                     42

<210> SEQ ID NO 126
<211> LENGTH: 31
<212> TYPE: DNA
<213> ORGANISM: Artificial Sequence
<220> FEATURE:
<223> OTHER INFORMATION: DNA origami staple

<400> SEQUENCE: 126
aaaatgaaaa taccgttcca gtaagcgtca t                                 31

<210> SEQ ID NO 127
<211> LENGTH: 31
<212> TYPE: DNA
<213> ORGANISM: Artificial Sequence
<220> FEATURE:
<223> OTHER INFORMATION: DNA origami staple

<400> SEQUENCE: 127
tcgtctgaaa tgaataccga acgaaccacc a                                 31

<210> SEQ ID NO 128
<211> LENGTH: 42
<212> TYPE: DNA
<213> ORGANISM: Artificial Sequence
<220> FEATURE:
<223> OTHER INFORMATION: DNA origami staple

<400> SEQUENCE: 128
gagtaaacaa caggaaggag cgaataatgc agattcccta aa                     42

<210> SEQ ID NO 129
<211> LENGTH: 42
<212> TYPE: DNA
<213> ORGANISM: Artificial Sequence
<220> FEATURE:
<223> OTHER INFORMATION: DNA origami staple

<400> SEQUENCE: 129
ggggcgcgct tgccaagagg aagtaacaaa ataaattaga cg                     42

<210> SEQ ID NO 130
<211> LENGTH: 42
<212> TYPE: DNA
<213> ORGANISM: Artificial Sequence
<220> FEATURE:
<223> OTHER INFORMATION: DNA origami staple

<400> SEQUENCE: 130
gcatcaagct gctcacagac ctttaacgag aatggacata aa    42

<210> SEQ ID NO 131
<211> LENGTH: 42
<212> TYPE: DNA
<213> ORGANISM: Artificial Sequence
<220> FEATURE:
<223> OTHER INFORMATION: DNA origami staple

<400> SEQUENCE: 131
gtagcattac ccaagctgac caggagtgga atttagcagc ct    42

<210> SEQ ID NO 132
<211> LENGTH: 30
<212> TYPE: DNA
<213> ORGANISM: Artificial Sequence
<220> FEATURE:
<223> OTHER INFORMATION: DNA origami staple

<400> SEQUENCE: 132
gccgtcaata gataatcaac taaacagagg    30

<210> SEQ ID NO 133
<211> LENGTH: 21
<212> TYPE: DNA
<213> ORGANISM: Artificial Sequence
<220> FEATURE:
<223> OTHER INFORMATION: DNA origami staple

<400> SEQUENCE: 133
agaagtaaaa tatcttaaca c    21

<210> SEQ ID NO 134
<211> LENGTH: 21
<212> TYPE: DNA
<213> ORGANISM: Artificial Sequence
<220> FEATURE:
<223> OTHER INFORMATION: DNA origami staple

<400> SEQUENCE: 134
caattcggga attgccacgc t    21

<210> SEQ ID NO 135
<211> LENGTH: 21
<212> TYPE: DNA
<213> ORGANISM: Artificial Sequence
<220> FEATURE:
<223> OTHER INFORMATION: DNA origami staple

<400> SEQUENCE: 135
atcctttttg gcaaaatgaa a    21

<210> SEQ ID NO 136
<211> LENGTH: 21
<212> TYPE: DNA
<213> ORGANISM: Artificial Sequence
<220> FEATURE:
<223> OTHER INFORMATION: DNA origami staple

<400> SEQUENCE: 136
aattttacct caatccttgc t    21

<210> SEQ ID NO 137
<211> LENGTH: 42
<212> TYPE: DNA

<213> ORGANISM: Artificial Sequence
<220> FEATURE:
<223> OTHER INFORMATION: DNA origami staple

<400> SEQUENCE: 137
tgaatttatt cattgggaag gtaaatataa gacaataaac aa          42

<210> SEQ ID NO 138
<211> LENGTH: 21
<212> TYPE: DNA
<213> ORGANISM: Artificial Sequence
<220> FEATURE:
<223> OTHER INFORMATION: DNA origami staple

<400> SEQUENCE: 138
gaaaccacga caaagcagaa c          21

<210> SEQ ID NO 139
<211> LENGTH: 21
<212> TYPE: DNA
<213> ORGANISM: Artificial Sequence
<220> FEATURE:
<223> OTHER INFORMATION: DNA origami staple

<400> SEQUENCE: 139
attatcataa taagacaata g          21

<210> SEQ ID NO 140
<211> LENGTH: 21
<212> TYPE: DNA
<213> ORGANISM: Artificial Sequence
<220> FEATURE:
<223> OTHER INFORMATION: DNA origami staple

<400> SEQUENCE: 140
atcagatgca gaggagaaaa a          21

<210> SEQ ID NO 141
<211> LENGTH: 21
<212> TYPE: DNA
<213> ORGANISM: Artificial Sequence
<220> FEATURE:
<223> OTHER INFORMATION: DNA origami staple

<400> SEQUENCE: 141
aatataacaa cgccaattta c          21

<210> SEQ ID NO 142
<211> LENGTH: 21
<212> TYPE: DNA
<213> ORGANISM: Artificial Sequence
<220> FEATURE:
<223> OTHER INFORMATION: DNA origami staple

<400> SEQUENCE: 142
attatacatt gagacaatca a          21

<210> SEQ ID NO 143
<211> LENGTH: 21
<212> TYPE: DNA
<213> ORGANISM: Artificial Sequence
<220> FEATURE:
<223> OTHER INFORMATION: DNA origami staple

<400> SEQUENCE: 143
agggttaaac gctctcctta t          21

<210> SEQ ID NO 144
<211> LENGTH: 21
<212> TYPE: DNA
<213> ORGANISM: Artificial Sequence
<220> FEATURE:
<223> OTHER INFORMATION: DNA origami staple

<400> SEQUENCE: 144
aaaattaaat tcttgtatta a                                              21

<210> SEQ ID NO 145
<211> LENGTH: 21
<212> TYPE: DNA
<213> ORGANISM: Artificial Sequence
<220> FEATURE:
<223> OTHER INFORMATION: DNA origami staple

<400> SEQUENCE: 145
attttcaaat tactttttta t                                              21

<210> SEQ ID NO 146
<211> LENGTH: 21
<212> TYPE: DNA
<213> ORGANISM: Artificial Sequence
<220> FEATURE:
<223> OTHER INFORMATION: DNA origami staple

<400> SEQUENCE: 146
tgaatataag aatatcatta c                                              21

<210> SEQ ID NO 147
<211> LENGTH: 21
<212> TYPE: DNA
<213> ORGANISM: Artificial Sequence
<220> FEATURE:
<223> OTHER INFORMATION: DNA origami staple

<400> SEQUENCE: 147
ttttacagtg ataaagcaaa t                                              21

<210> SEQ ID NO 148
<211> LENGTH: 21
<212> TYPE: DNA
<213> ORGANISM: Artificial Sequence
<220> FEATURE:
<223> OTHER INFORMATION: DNA origami staple

<400> SEQUENCE: 148
aacggatatg gtttttatcc g                                              21

<210> SEQ ID NO 149
<211> LENGTH: 21
<212> TYPE: DNA
<213> ORGANISM: Artificial Sequence
<220> FEATURE:
<223> OTHER INFORMATION: DNA origami staple

<400> SEQUENCE: 149
tgaatactca tcttcgaggc g                                              21

<210> SEQ ID NO 150
<211> LENGTH: 21
<212> TYPE: DNA
<213> ORGANISM: Artificial Sequence
<220> FEATURE:

<223> OTHER INFORMATION: DNA origami staple

<400> SEQUENCE: 150
gcgcagatca aataccgact t                                     21

<210> SEQ ID NO 151
<211> LENGTH: 21
<212> TYPE: DNA
<213> ORGANISM: Artificial Sequence
<220> FEATURE:
<223> OTHER INFORMATION: DNA origami staple

<400> SEQUENCE: 151
ttcaattaaa gaacagcctt a                                     21

<210> SEQ ID NO 152
<211> LENGTH: 21
<212> TYPE: DNA
<213> ORGANISM: Artificial Sequence
<220> FEATURE:
<223> OTHER INFORMATION: DNA origami staple

<400> SEQUENCE: 152
agatgatatg caaagctatt t                                     21

<210> SEQ ID NO 153
<211> LENGTH: 21
<212> TYPE: DNA
<213> ORGANISM: Artificial Sequence
<220> FEATURE:
<223> OTHER INFORMATION: DNA origami staple

<400> SEQUENCE: 153
gaaaacatat aactatttta t                                     21

<210> SEQ ID NO 154
<211> LENGTH: 21
<212> TYPE: DNA
<213> ORGANISM: Artificial Sequence
<220> FEATURE:
<223> OTHER INFORMATION: DNA origami staple

<400> SEQUENCE: 154
taacaatcct ccggacgcta a                                     21

<210> SEQ ID NO 155
<211> LENGTH: 21
<212> TYPE: DNA
<213> ORGANISM: Artificial Sequence
<220> FEATURE:
<223> OTHER INFORMATION: DNA origami staple

<400> SEQUENCE: 155 cttttttct gagagagcct a                                      21

<210> SEQ ID NO 156
<211> LENGTH: 21
<212> TYPE: DNA
<213> ORGANISM: Artificial Sequence
<220> FEATURE:
<223> OTHER INFORMATION: DNA origami staple

<400> SEQUENCE: 156
ataaatctga atttaaataa a                                     21

```
<210> SEQ ID NO 157
<211> LENGTH: 21
<212> TYPE: DNA
<213> ORGANISM: Artificial Sequence
<220> FEATURE:
<223> OTHER INFORMATION: DNA origami staple

<400> SEQUENCE: 157
aataaccgac gctgatccca a                                              21

<210> SEQ ID NO 158
<211> LENGTH: 33
<212> TYPE: DNA
<213> ORGANISM: Artificial Sequence
<220> FEATURE:
<223> OTHER INFORMATION: DNA origami staple

<400> SEQUENCE: 158
cgtcgctcat agcggatttt ttgtttaacg tca                                 33

<210> SEQ ID NO 159
<211> LENGTH: 21
<212> TYPE: DNA
<213> ORGANISM: Artificial Sequence
<220> FEATURE:
<223> OTHER INFORMATION: DNA origami staple

<400> SEQUENCE: 159
gcagaagata aatagattag a                                              21

<210> SEQ ID NO 160
<211> LENGTH: 22
<212> TYPE: DNA
<213> ORGANISM: Artificial Sequence
<220> FEATURE:
<223> OTHER INFORMATION: DNA origami staple

<400> SEQUENCE: 160
acatcgcgtc agtatttagg ag                                             22

<210> SEQ ID NO 161
<211> LENGTH: 43
<212> TYPE: DNA
<213> ORGANISM: Artificial Sequence
<220> FEATURE:
<223> OTHER INFORMATION: DNA origami staple

<400> SEQUENCE: 161
aggaacacca gtaactttaa tgcgcgaaaa cagtgaggaa ggt                      43

<210> SEQ ID NO 162
<211> LENGTH: 43
<212> TYPE: DNA
<213> ORGANISM: Artificial Sequence
<220> FEATURE:
<223> OTHER INFORMATION: DNA origami staple

<400> SEQUENCE: 162
ttcagcgtgg ccaatatttt tgaatggcag cagcaatcaa cag                      43

<210> SEQ ID NO 163
<211> LENGTH: 42
<212> TYPE: DNA
<213> ORGANISM: Artificial Sequence
<220> FEATURE:
<223> OTHER INFORMATION: DNA origami staple
```

<400> SEQUENCE: 163
gaacctctga gcgtaagaat acgtggcaag catcacaata tc                            42

<210> SEQ ID NO 164
<211> LENGTH: 22
<212> TYPE: DNA
<213> ORGANISM: Artificial Sequence
<220> FEATURE:
<223> OTHER INFORMATION: DNA origami staple

<400> SEQUENCE: 164
attatcatgt ccagacgaca ta                                                  22

<210> SEQ ID NO 165
<211> LENGTH: 43
<212> TYPE: DNA
<213> ORGANISM: Artificial Sequence
<220> FEATURE:
<223> OTHER INFORMATION: DNA origami staple

<400> SEQUENCE: 165
gtctttcacc gtcagacatt caaccgatag ctaataggta aag                           43

<210> SEQ ID NO 166
<211> LENGTH: 43
<212> TYPE: DNA
<213> ORGANISM: Artificial Sequence
<220> FEATURE:
<223> OTHER INFORMATION: DNA origami staple

<400> SEQUENCE: 166
aggattaaga gccagcaaga aacaatgagt tttgagcgag aaa                           43

<210> SEQ ID NO 167
<211> LENGTH: 43
<212> TYPE: DNA
<213> ORGANISM: Artificial Sequence
<220> FEATURE:
<223> OTHER INFORMATION: DNA origami staple

<400> SEQUENCE: 167
agactccgcc accagagtta agcccaatat tagtttccaa tcg                           43

<210> SEQ ID NO 168
<211> LENGTH: 43
<212> TYPE: DNA
<213> ORGANISM: Artificial Sequence
<220> FEATURE:
<223> OTHER INFORMATION: DNA origami staple

<400> SEQUENCE: 168
catgaaagcc gccggagaga taacccacag ctacaatatg taa                           43

<210> SEQ ID NO 169
<211> LENGTH: 43
<212> TYPE: DNA
<213> ORGANISM: Artificial Sequence
<220> FEATURE:
<223> OTHER INFORMATION: DNA origami staple

<400> SEQUENCE: 169
tcggaacagg ttgaggtaat tgagcgctct taccacttag gtt                           43

<210> SEQ ID NO 170
<211> LENGTH: 43

<212> TYPE: DNA
<213> ORGANISM: Artificial Sequence
<220> FEATURE:
<223> OTHER INFORMATION: DNA origami staple

<400> SEQUENCE: 170
agttaatttg gcctacaccc tgaacaaact ttccagacta cct       43

<210> SEQ ID NO 171
<211> LENGTH: 22
<212> TYPE: DNA
<213> ORGANISM: Artificial Sequence
<220> FEATURE:
<223> OTHER INFORMATION: DNA origami staple

<400> SEQUENCE: 171
aacagggatt atttagaaga gt       22

<210> SEQ ID NO 172
<211> LENGTH: 22
<212> TYPE: DNA
<213> ORGANISM: Artificial Sequence
<220> FEATURE:
<223> OTHER INFORMATION: DNA origami staple

<400> SEQUENCE: 172
ttacagaaag aaacatagct ta       22

<210> SEQ ID NO 173
<211> LENGTH: 42
<212> TYPE: DNA
<213> ORGANISM: Artificial Sequence
<220> FEATURE:
<223> OTHER INFORMATION: DNA origami staple

<400> SEQUENCE: 173
tgaggcgcat taaagattat ttacattgaa tttttaggat tt       42

<210> SEQ ID NO 174
<211> LENGTH: 42
<212> TYPE: DNA
<213> ORGANISM: Artificial Sequence
<220> FEATURE:
<223> OTHER INFORMATION: DNA origami staple

<400> SEQUENCE: 174
cgcctgcctg atagcaccag tcacacgaac taaagttaca aa       42

<210> SEQ ID NO 175
<211> LENGTH: 42
<212> TYPE: DNA
<213> ORGANISM: Artificial Sequence
<220> FEATURE:
<223> OTHER INFORMATION: DNA origami staple

<400> SEQUENCE: 175
gagagcctat tagttaaaag ggacattcga gtgaggtatt aa       42

<210> SEQ ID NO 176
<211> LENGTH: 42
<212> TYPE: DNA
<213> ORGANISM: Artificial Sequence
<220> FEATURE:
<223> OTHER INFORMATION: DNA origami staple

<400> SEQUENCE: 176
aatctaacag acaacagaga tagaacccca actttcgtta tt                              42

<210> SEQ ID NO 177
<211> LENGTH: 42
<212> TYPE: DNA
<213> ORGANISM: Artificial Sequence
<220> FEATURE:
<223> OTHER INFORMATION: DNA origami staple

<400> SEQUENCE: 177
tgctaaattc tgacctgaaa cggaaatttc tgtatgagta ac                              42

<210> SEQ ID NO 178
<211> LENGTH: 42
<212> TYPE: DNA
<213> ORGANISM: Artificial Sequence
<220> FEATURE:
<223> OTHER INFORMATION: DNA origami staple

<400> SEQUENCE: 178
catgttctga gggaaaaggt gaattatcca gacgtgaaca aa                              42

<210> SEQ ID NO 179
<211> LENGTH: 42
<212> TYPE: DNA
<213> ORGANISM: Artificial Sequence
<220> FEATURE:
<223> OTHER INFORMATION: DNA origami staple

<400> SEQUENCE: 179
gcgcctgaaa gggcccgact tgagccattc taaaggagcg ga                              42

<210> SEQ ID NO 180
<211> LENGTH: 42
<212> TYPE: DNA
<213> ORGANISM: Artificial Sequence
<220> FEATURE:
<223> OTHER INFORMATION: DNA origami staple

<400> SEQUENCE: 180
ataagtcggt ttacttagag ccagcaaacc ctcatcctga tt                              42

<210> SEQ ID NO 181
<211> LENGTH: 42
<212> TYPE: DNA
<213> ORGANISM: Artificial Sequence
<220> FEATURE:
<223> OTHER INFORMATION: DNA origami staple

<400> SEQUENCE: 181
taatatccaa tcaagtagca ccattacccc tgtagattca tc                              42

<210> SEQ ID NO 182
<211> LENGTH: 42
<212> TYPE: DNA
<213> ORGANISM: Artificial Sequence
<220> FEATURE:
<223> OTHER INFORMATION: DNA origami staple

<400> SEQUENCE: 182
gagcatgcgg aataaggccg gaaacgtctc accagtgttt gg                              42

<210> SEQ ID NO 183
<211> LENGTH: 42
<212> TYPE: DNA
<213> ORGANISM: Artificial Sequence
<220> FEATURE:
<223> OTHER INFORMATION: DNA origami staple

<400> SEQUENCE: 183
taatcggaaa agaaaaacca tcgatagcgt accgttaatg ga         42

<210> SEQ ID NO 184
<211> LENGTH: 42
<212> TYPE: DNA
<213> ORGANISM: Artificial Sequence
<220> FEATURE:
<223> OTHER INFORMATION: DNA origami staple

<400> SEQUENCE: 184
cattccatac ataataatca gtagcgacgc aagccccata tc         42

<210> SEQ ID NO 185
<211> LENGTH: 42
<212> TYPE: DNA
<213> ORGANISM: Artificial Sequence
<220> FEATURE:
<223> OTHER INFORMATION: DNA origami staple

<400> SEQUENCE: 185
accaagttta gcaaagtttg cctttagccc accctgtaaa ac         42

<210> SEQ ID NO 186
<211> LENGTH: 42
<212> TYPE: DNA
<213> ORGANISM: Artificial Sequence
<220> FEATURE:
<223> OTHER INFORMATION: DNA origami staple

<400> SEQUENCE: 186
gaacaaggac tccttgtagc gcgttttcga accgctgcgt ag         42

<210> SEQ ID NO 187
<211> LENGTH: 42
<212> TYPE: DNA
<213> ORGANISM: Artificial Sequence
<220> FEATURE:
<223> OTHER INFORMATION: DNA origami staple

<400> SEQUENCE: 187
tttcatccaa aagattttcg gtcatagccc ctcagcgtca ga         42

<210> SEQ ID NO 188
<211> LENGTH: 42
<212> TYPE: DNA
<213> ORGANISM: Artificial Sequence
<220> FEATURE:
<223> OTHER INFORMATION: DNA origami staple

<400> SEQUENCE: 188
cgcgcccacg caatttagcg tttgccattc aggagcagta cc         42

<210> SEQ ID NO 189
<211> LENGTH: 42
<212> TYPE: DNA
<213> ORGANISM: Artificial Sequence
<220> FEATURE:
<223> OTHER INFORMATION: DNA origami staple

<400> SEQUENCE: 189
cagatattac cagataatca aaatcaccgg aatagaaaca at         42

```
<210> SEQ ID NO 190
<211> LENGTH: 42
<212> TYPE: DNA
<213> ORGANISM: Artificial Sequence
<220> FEATURE:
<223> OTHER INFORMATION: DNA origami staple

<400> SEQUENCE: 190
gtattctaag cagagagcca ccaccggagg gttgaattgc tt                              42

<210> SEQ ID NO 191
<211> LENGTH: 42
<212> TYPE: DNA
<213> ORGANISM: Artificial Sequence
<220> FEATURE:
<223> OTHER INFORMATION: DNA origami staple

<400> SEQUENCE: 191
ttttagcgaa gcccccctca gagccgccgg cggatcaaaa tc                              42

<210> SEQ ID NO 192
<211> LENGTH: 42
<212> TYPE: DNA
<213> ORGANISM: Artificial Sequence
<220> FEATURE:
<223> OTHER INFORMATION: DNA origami staple

<400> SEQUENCE: 192
gcgggagaat agcagaaccg ccaccctcgc ggggttattc at                              42

<210> SEQ ID NO 193
<211> LENGTH: 42
<212> TYPE: DNA
<213> ORGANISM: Artificial Sequence
<220> FEATURE:
<223> OTHER INFORMATION: DNA origami staple

<400> SEQUENCE: 193
aatcaagaat aagaccaccc tcagagcctc aagagcaaaa ga                              42

<210> SEQ ID NO 194
<211> LENGTH: 42
<212> TYPE: DNA
<213> ORGANISM: Artificial Sequence
<220> FEATURE:
<223> OTHER INFORMATION: DNA origami staple

<400> SEQUENCE: 194
tgcacccaag aattgaacca ccaccagagt attaaacatc aa                              42

<210> SEQ ID NO 195
<211> LENGTH: 42
<212> TYPE: DNA
<213> ORGANISM: Artificial Sequence
<220> FEATURE:
<223> OTHER INFORMATION: DNA origami staple

<400> SEQUENCE: 195
cctgaataat atcaccagca ttgacaggct attatttaca tt                              42

<210> SEQ ID NO 196
<211> LENGTH: 42
<212> TYPE: DNA
<213> ORGANISM: Artificial Sequence
<220> FEATURE:
<223> OTHER INFORMATION: DNA origami staple
```

<400> SEQUENCE: 196
cgagcgtgtc agagggcagg tcagacgagc ccctgaatt ac                          42

<210> SEQ ID NO 197
<211> LENGTH: 42
<212> TYPE: DNA
<213> ORGANISM: Artificial Sequence
<220> FEATURE:
<223> OTHER INFORMATION: DNA origami staple

<400> SEQUENCE: 197
atttgcctaa ctgatgatat tcacaaacgt gcccgacagt ac                         42

<210> SEQ ID NO 198
<211> LENGTH: 42
<212> TYPE: DNA
<213> ORGANISM: Artificial Sequence
<220> FEATURE:
<223> OTHER INFORMATION: DNA origami staple

<400> SEQUENCE: 198
cagccataag cgcatcctca ttaaagccgg gtcaggtgag tg                         42

<210> SEQ ID NO 199
<211> LENGTH: 42
<212> TYPE: DNA
<213> ORGANISM: Artificial Sequence
<220> FEATURE:
<223> OTHER INFORMATION: DNA origami staple

<400> SEQUENCE: 199
tccaaatgag aataaaagcg cagtctctta ctggttgtaa at                         42

<210> SEQ ID NO 200
<211> LENGTH: 32
<212> TYPE: DNA
<213> ORGANISM: Artificial Sequence
<220> FEATURE:
<223> OTHER INFORMATION: DNA origami staple

<400> SEQUENCE: 200
ttagaatcct tgaaaaatta attaattttc cc                                    32

<210> SEQ ID NO 201
<211> LENGTH: 43
<212> TYPE: DNA
<213> ORGANISM: Artificial Sequence
<220> FEATURE:
<223> OTHER INFORMATION: DNA origami staple

<400> SEQUENCE: 201
gagagcagac ctggaactcg ttcttgcaga tagcccaata att                        43

<210> SEQ ID NO 202
<211> LENGTH: 43
<212> TYPE: DNA
<213> ORGANISM: Artificial Sequence
<220> FEATURE:
<223> OTHER INFORMATION: DNA origami staple

<400> SEQUENCE: 202
gagagcagac ctggaactcg ttcttttgca atccctctgt agc                        43

<210> SEQ ID NO 203

```
<211> LENGTH: 43
<212> TYPE: DNA
<213> ORGANISM: Artificial Sequence
<220> FEATURE:
<223> OTHER INFORMATION: DNA origami staple

<400> SEQUENCE: 203
gagagcagac ctggaactcg ttcagcagct ggtggtatta aat          43

<210> SEQ ID NO 204
<211> LENGTH: 43
<212> TYPE: DNA
<213> ORGANISM: Artificial Sequence
<220> FEATURE:
<223> OTHER INFORMATION: DNA origami staple

<400> SEQUENCE: 204
gagagcagac ctggaactcg ttgaacgagg caggcgaccc gtc          43

<210> SEQ ID NO 205
<211> LENGTH: 43
<212> TYPE: DNA
<213> ORGANISM: Artificial Sequence
<220> FEATURE:
<223> OTHER INFORMATION: DNA origami staple

<400> SEQUENCE: 205
gagagcagac ctggaactcg ttcagaggcg gtccacaaca aac          43

<210> SEQ ID NO 206
<211> LENGTH: 43
<212> TYPE: DNA
<213> ORGANISM: Artificial Sequence
<220> FEATURE:
<223> OTHER INFORMATION: DNA origami staple

<400> SEQUENCE: 206
gagagcagac ctggaactcg ttactttttc ctgagaaatg gga          43

<210> SEQ ID NO 207
<211> LENGTH: 43
<212> TYPE: DNA
<213> ORGANISM: Artificial Sequence
<220> FEATURE:
<223> OTHER INFORMATION: DNA origami staple

<400> SEQUENCE: 207
gagagcagac ctggaactcg ttcattaaag attgccgtag atg          43

<210> SEQ ID NO 208
<211> LENGTH: 43
<212> TYPE: DNA
<213> ORGANISM: Artificial Sequence
<220> FEATURE:
<223> OTHER INFORMATION: DNA origami staple

<400> SEQUENCE: 208
gagagcagac ctggaactcg ttaatgccac cagtgagtgc atc          43

<210> SEQ ID NO 209
<211> LENGTH: 43
<212> TYPE: DNA
<213> ORGANISM: Artificial Sequence
<220> FEATURE:
<223> OTHER INFORMATION: DNA origami staple

<400> SEQUENCE: 209
```

```
gagagcagac ctggaactcg ttacctaaac cagggtgacg acg          43

<210> SEQ ID NO 210
<211> LENGTH: 43
<212> TYPE: DNA
<213> ORGANISM: Artificial Sequence
<220> FEATURE:
<223> OTHER INFORMATION: DNA origami staple

<400> SEQUENCE: 210
gagagcagac ctggaactcg ttagaataca ggcggtagga aga          43

<210> SEQ ID NO 211
<211> LENGTH: 43
<212> TYPE: DNA
<213> ORGANISM: Artificial Sequence
<220> FEATURE:
<223> OTHER INFORMATION: DNA origami staple

<400> SEQUENCE: 211
gagagcagac ctggaactcg ttctttgaca atcggcgctt tcc          43

<210> SEQ ID NO 212
<211> LENGTH: 43
<212> TYPE: DNA
<213> ORGANISM: Artificial Sequence
<220> FEATURE:
<223> OTHER INFORMATION: DNA origami staple

<400> SEQUENCE: 212
gagagcagac ctggaactcg ttccaagcgg tcgtgctgcc gga          43

<210> SEQ ID NO 213
<211> LENGTH: 43
<212> TYPE: DNA
<213> ORGANISM: Artificial Sequence
<220> FEATURE:
<223> OTHER INFORMATION: DNA origami staple

<400> SEQUENCE: 213
gagagcagac ctggaactcg ttacggagac gctttcccat tcg          43

<210> SEQ ID NO 214
<211> LENGTH: 43
<212> TYPE: DNA
<213> ORGANISM: Artificial Sequence
<220> FEATURE:
<223> OTHER INFORMATION: DNA origami staple

<400> SEQUENCE: 214
gtctcgtcgt ctaccgcaat ttgtaacgat tgggaacagc gcc          43

<210> SEQ ID NO 215
<211> LENGTH: 43
<212> TYPE: DNA
<213> ORGANISM: Artificial Sequence
<220> FEATURE:
<223> OTHER INFORMATION: DNA origami staple

<400> SEQUENCE: 215
gtctcgtcgt ctaccgcaat ttcagacaga tcaccataga aaa          43

<210> SEQ ID NO 216
<211> LENGTH: 43
<212> TYPE: DNA
```

<213> ORGANISM: Artificial Sequence
<220> FEATURE:
<223> OTHER INFORMATION: DNA origami staple

<400> SEQUENCE: 216
gtctcgtcgt ctaccgcaat tttacaacga ttagcaagtt tat     43

<210> SEQ ID NO 217
<211> LENGTH: 43
<212> TYPE: DNA
<213> ORGANISM: Artificial Sequence
<220> FEATURE:
<223> OTHER INFORMATION: DNA origami staple

<400> SEQUENCE: 217
gtctcgtcgt ctaccgcaat ttagtttcga ccaatgacgc aaa     43

<210> SEQ ID NO 218
<211> LENGTH: 43
<212> TYPE: DNA
<213> ORGANISM: Artificial Sequence
<220> FEATURE:
<223> OTHER INFORMATION: DNA origami staple

<400> SEQUENCE: 218
gtctcgtcgt ctaccgcaat ttaacccata gcaccgaggt ggc     43

<210> SEQ ID NO 219
<211> LENGTH: 43
<212> TYPE: DNA
<213> ORGANISM: Artificial Sequence
<220> FEATURE:
<223> OTHER INFORMATION: DNA origami staple

<400> SEQUENCE: 219
gtctcgtcgt ctaccgcaat ttagggataa gaatcaacgt aga     43

<210> SEQ ID NO 220
<211> LENGTH: 43
<212> TYPE: DNA
<213> ORGANISM: Artificial Sequence
<220> FEATURE:
<223> OTHER INFORMATION: DNA origami staple

<400> SEQUENCE: 220
gtctcgtcgt ctaccgcaat ttagagccag tcagactatt acg     43

<210> SEQ ID NO 221
<211> LENGTH: 43
<212> TYPE: DNA
<213> ORGANISM: Artificial Sequence
<220> FEATURE:
<223> OTHER INFORMATION: DNA origami staple

<400> SEQUENCE: 221
gtctcgtcgt ctaccgcaat ttaccctcaa tcggcaactg gca     43

<210> SEQ ID NO 222
<211> LENGTH: 43
<212> TYPE: DNA
<213> ORGANISM: Artificial Sequence
<220> FEATURE:
<223> OTHER INFORMATION: DNA origami staple

<400> SEQUENCE: 222
gtctcgtcgt ctaccgcaat ttaccgccac cccttaaata acg     43

<210> SEQ ID NO 223
<211> LENGTH: 43
<212> TYPE: DNA
<213> ORGANISM: Artificial Sequence
<220> FEATURE:
<223> OTHER INFORMATION: DNA origami staple

<400> SEQUENCE: 223
gtctcgtcgt ctaccgcaat ttaccgtacc ttttcaagga aac        43

<210> SEQ ID NO 224
<211> LENGTH: 43
<212> TYPE: DNA
<213> ORGANISM: Artificial Sequence
<220> FEATURE:
<223> OTHER INFORMATION: DNA origami staple

<400> SEQUENCE: 224
gtctcgtcgt ctaccgcaat ttatagcccg gaaccatagc cga        43

<210> SEQ ID NO 225
<211> LENGTH: 43
<212> TYPE: DNA
<213> ORGANISM: Artificial Sequence
<220> FEATURE:
<223> OTHER INFORMATION: DNA origami staple

<400> SEQUENCE: 225
gtctcgtcgt ctaccgcaat ttgtcgagaa ccgccttttt taa        43

<210> SEQ ID NO 226
<211> LENGTH: 43
<212> TYPE: DNA
<213> ORGANISM: Artificial Sequence
<220> FEATURE:
<223> OTHER INFORMATION: DNA origami staple

<400> SEQUENCE: 226
gtctcgtcgt ctaccgcaat ttagtaccaa ccctcaatag cta        43

<210> SEQ ID NO 227
<211> LENGTH: 43
<212> TYPE: DNA
<213> ORGANISM: Artificial Sequence
<220> FEATURE:
<223> OTHER INFORMATION: DNA origami staple

<400> SEQUENCE: 227
aaaggacagg attagatcta cttgtcctta cacagaggct tga        43

<210> SEQ ID NO 228
<211> LENGTH: 43
<212> TYPE: DNA
<213> ORGANISM: Artificial Sequence
<220> FEATURE:
<223> OTHER INFORMATION: DNA origami staple

<400> SEQUENCE: 228
agaaatatag tatctcatcg attccgaatg gcatctgaca gtt        43

<210> SEQ ID NO 229
<211> LENGTH: 20
<212> TYPE: DNA
<213> ORGANISM: Artificial Sequence
<220> FEATURE:

<223> OTHER INFORMATION: Cy5 fluorophore tagged DNA origami staple

<400> SEQUENCE: 229
cgagttccag gtctgctctc                                                   20

<210> SEQ ID NO 230
<211> LENGTH: 20
<212> TYPE: DNA
<213> ORGANISM: Artificial Sequence
<220> FEATURE:
<223> OTHER INFORMATION: Cy3 fluorophore tagged DNA origami staple

<400> SEQUENCE: 230
attgcggtag acgacgagac                                                   20

<210> SEQ ID NO 231
<211> LENGTH: 20
<212> TYPE: DNA
<213> ORGANISM: Artificial Sequence
<220> FEATURE:
<223> OTHER INFORMATION: Biotinylated DNA origami staple

<400> SEQUENCE: 231
tcaagcctct gtgtaaggac                                                   20

<210> SEQ ID NO 232
<211> LENGTH: 20
<212> TYPE: DNA
<213> ORGANISM: Artificial Sequence
<220> FEATURE:
<223> OTHER INFORMATION: Biotinylated DNA origami staple

<400> SEQUENCE: 232
aactgtcaga tgccattcgg                                                   20

<210> SEQ ID NO 233
<211> LENGTH: 7249
<212> TYPE: DNA
<213> ORGANISM: Bacteriophage M13mp18

<400> SEQUENCE: 233
aatgctacta ctattagtag aattgatgcc accttttcag ctcgcgcccc aaatgaaaat      60
atagctaaac aggttattga ccatttgcga aatgtatcta atggtcaaac taatctact     120 cgttcgcaga attgggaatc aactgttata tggaatgaaa cttccagaca ccgtacttta    180
gttgcatatt taaacatgt tgagctacag cattatattc agcaattaag ctctaagcca     240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag    360
tctttcgggc ttcctcttaa tcttttgat gcaatccgct ttgcttctga ctataatagt     420
cagggtaaag acctgatttt tgatttatgg tcattctcgt tttctgaact gtttaaagca    480
tttgaggggg attcaatgaa tatttatgac gattccgcag tattggacgc tatccagtct   540
aaacatttta ctattacccc ctctggcaaa acttcttttg caaaagcctc tcgctatttt    600 ggttttatc gtcgtctggt aaacgagggt tatgatagtg ttgctcttac tatgcctcgt    660
aattcctttt ggcgttatgt atctgcatta gttgaatgtg gtattcctaa atctcaactg   720
atgaatcttt ctacctgtaa taatgttgtt ccgttagttc gttttattaa cgtagatttt   780
tcttcccaac gtcctgactg gtataatgag ccagttctta aaatcgcata aggtaattca    840
caatgattaa agttgaaatt aaaccatctc aagcccaatt tactactcgt tctggtgttt    900

```
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttcccct atgattgacc   1080
gtctgcgcct cgttccggct aagtaacatg agcaggtcg cggatttcga cacaatttat    1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctccttt  ggagcctttt    1560 ttttggagat tttcaacgtg aaaaaattat tattcgcaat tcctttagtt gttccttct    1620 attctcactc cgctgaaact gttgaaagtt gtttagcaaa atcccataca gaaaattcat   1680
ttactaacgt ctggaaagac gacaaaaactt tagatcgtta cgctaactat gagggctgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcagggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgagggag cggttccgg tggtggctct ggttccggtg    2400
attttgatta tgaaaagatg gcaaacgcta ataagggggc tatgaccgaa aatgccgatg   2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttgg cgctggtaaa ccatatgaat tttctattga ttgtgacaaa ataaacttat   2760
tccgtggtgt ctttgcgttt cttttatatg ttgccacctt tatgtatgta ttttctacgt   2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcattttgac gttaaacaa aaaatcgttt cttatttgga    3180
ttgggataaa taatatggct gtttattttg taactggcaa attaggctct ggaaagacgc   3240
```

```
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840 ccggtgttta ttcttatttta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta atgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatattttt agataaccct cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttaatgg cgatgtttta    4980 gggctatcag ttcgcgcatt aaagactaat agccattcaa aaatattgtc tgtgccacgt    5040
attcttacgc tttcaggtca gaagggttct atctctgttg gccagaatgt ccctttttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
```

```
ggggctccct ttagggttcc gatttagtgc tttacggcac ctcgacccca aaaaacttga    5700
tttgggtgat ggttcacgta gtgggccatc gccctgatag acggttttc gccctttgac     5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360
atccccctttc cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac tgtcgtcgtc ccctcaaact    6540
ggcagatgca cggttacgat gcgcccatct acaccaacgt gacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa tgcgaatttt aacaaaatat taacgtttac    6780
aatttaaata tttgcttata caatcttcct gttttgggg cttttctgat tatcaaccgg     6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct caccctttg aatctttacc tacacattac tcaggcattg catttaaaat     7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200
gcttaattttt gctaattctt tgccttgcct gtatgattta ttggatgtt                7249
```